US008765744B2

(12) United States Patent
Himmelsbach

(10) Patent No.: US 8,765,744 B2
(45) Date of Patent: Jul. 1, 2014

(54) AZASPIROHEXANONES

(75) Inventor: Frank Himmelsbach, Mittlebiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 151 days.

(21) Appl. No.: 13/166,895

(22) Filed: Jun. 23, 2011

(65) Prior Publication Data

US 2012/0190675 A1 Jul. 26, 2012

(30) Foreign Application Priority Data

Jun. 25, 2010 (EP) .................................. 10167325
Jun. 30, 2010 (EP) .................................. 10167958

(51) Int. Cl.
*C07D 413/08* (2006.01)
*A61K 31/537* (2006.01)

(52) U.S. Cl.
USPC .......... 514/228.8; 514/274; 514/275; 544/70; 544/230; 544/231; 546/16; 546/17

(58) Field of Classification Search
USPC .................. 544/70, 230, 231; 546/16, 17; 514/228.8, 274, 278
See application file for complete search history.

(56) References Cited

U.S. PATENT DOCUMENTS

| | | | |
|---|---|---|---|
| 3,341,538 A | 9/1967 | Block et al. | |
| 3,378,587 A | 4/1968 | Reinhardt | |
| 3,681,349 A | 8/1972 | Schwan et al. | |
| 3,703,529 A | 11/1972 | Cavalla et al. | |
| 3,919,047 A | 11/1975 | Vidic et al. | |
| 4,009,171 A | 2/1977 | Albertson | |
| 4,043,927 A | 8/1977 | Duling et al. | |
| 4,108,857 A | 8/1978 | Albertson | |
| 4,136,145 A | 1/1979 | Fuchs et al. | |
| 4,136,162 A | 1/1979 | Fuchs et al. | |
| 4,268,673 A | 5/1981 | Akkerman et al. | |
| 5,089,506 A | 2/1992 | Gray et al. | |
| 5,098,916 A | 3/1992 | Gray et al. | |
| 5,215,992 A | 6/1993 | Gray et al. | |
| 5,393,735 A | 2/1995 | Lange et al. | |
| 5,410,081 A | 4/1995 | Kunde et al. | |
| 5,432,175 A | 7/1995 | Piwinski et al. | |
| 5,480,899 A | 1/1996 | Yano et al. | |
| 5,502,027 A | 3/1996 | Lange et al. | |
| 5,631,209 A | 5/1997 | Lange et al. | |
| 5,776,959 A | 7/1998 | Covey et al. | |
| 5,780,466 A | 7/1998 | Emonds-Alt et al. | |
| 5,811,422 A | 9/1998 | Lam et al. | |
| 5,856,273 A | 1/1999 | Kay et al. | |
| 5,866,702 A | 2/1999 | Mackman et al. | |
| 5,936,124 A | 8/1999 | Hilborn et al. | |
| 5,981,436 A | 11/1999 | Drewes et al. | |
| 6,066,666 A | 5/2000 | Covey et al. | |
| 6,159,990 A | 12/2000 | Lagu et al. | |
| 6,242,637 B1 | 6/2001 | Emonds-Alt et al. | |
| 6,251,897 B1 | 6/2001 | Ina et al. | |
| 6,368,816 B2 | 4/2002 | Walker et al. | |
| 6,559,163 B2 | 5/2003 | Cai et al. | |
| 6,620,815 B1 | 9/2003 | Lagu et al. | |
| 6,635,630 B2 | 10/2003 | Shih et al. | |
| 6,638,935 B2 | 10/2003 | Emig et al. | |
| 6,653,315 B2 | 11/2003 | Tulshian et al. | |
| 6,706,722 B2 | 3/2004 | Emig et al. | |
| 6,794,390 B2 | 9/2004 | Lum et al. | |
| 6,838,253 B2 | 1/2005 | Walker et al. | |
| 6,841,671 B2 | 1/2005 | Noe et al. | |
| 6,890,926 B2 | 5/2005 | Emig et al. | |
| 6,900,201 B2 | 5/2005 | Noe et al. | |
| 6,916,807 B2 | 7/2005 | Freeman-Cook et al. | |
| 6,936,615 B2 | 8/2005 | Emig et al. | |
| 6,946,487 B2 | 9/2005 | Walker et al. | |
| 7,026,310 B2 | 4/2006 | Emig et al. | |
| 7,056,912 B2 | 6/2006 | Emig et al. | |

(Continued)

FOREIGN PATENT DOCUMENTS

| DE | 1801556 A1 | 5/1970 |
|---|---|---|
| DE | 19918725 A1 | 10/2000 |

(Continued)

OTHER PUBLICATIONS

Stewart et al., 11beta-hydroxysteroid Dehydrogenase, Vitamins and Hormones—Advances in Research and Applications, vol. 57, pp. 249-324, 1999.*
Abstract in English for DE10034623, Publication Date Jan. 31, 2002.
Aluri, B.R. et al., "Bulky n-Substituted 1,3-Benzazaphospholes: Access via Pd-Catalyzed C—N and C—P Cross Coupling, Lithiation, and Conversion to Novel P=C PtBu2 Hybrid Ligands". Inorganic Chemistry, 2008, 47, p. 6900-6912.
Aluri, B.R. et al., "Sterically and Polarity-Controlled Reactions of tBuLi with P=CH—NR Heterocycles: Novel Heterocyclic P-and P,O-Ligands and Preliminary Tests in Transition-Metal Catalysis", Chem. Eur. Journal, vol. 14, 2008, p. 4328-4335.

(Continued)

*Primary Examiner* — Deepak Rao
(74) *Attorney, Agent, or Firm* — Michael P. Morris; David L. Kershner

(57) ABSTRACT

The present invention relates to compounds defined by formula I

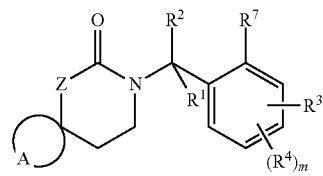

wherein the variables $R^1$, $R^2$, $R^3$, $R^4$, $R^7$, A, Z and m are as defined herein. The compounds of formula (I) are inhibitors of 11-beta-hydroxysteroid dehydrogenase 1 (11beta-HSD1) and thus are suitable for treatment and prevention of diseases which can be influenced by inhibition of this enzyme, such as metabolic diseases, in particular diabetes type 2, obesity, and dyslipidemia.

11 Claims, No Drawings

(56) References Cited

U.S. PATENT DOCUMENTS

| | | |
|---|---|---|
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | | |
|---|---|---|---|
| DE | 19929348 | A1 | 12/2000 |
| DE | 10034623 | A1 | 1/2002 |
| EP | 0415642 | A1 | 3/1991 |
| EP | 0454444 | A1 | 10/1991 |
| EP | 0471591 | A2 | 2/1992 |
| EP | 0640594 | A1 | 3/1995 |
| EP | 0645387 | A1 | 3/1995 |
| EP | 0928789 | A1 | 7/1999 |
| EP | 1156049 | A1 | 11/2001 |
| EP | 1270724 | A2 | 1/2003 |
| EP | 1801098 | A1 | 6/2007 |
| EP | 1852425 | A1 | 11/2007 |
| EP | 1864971 | A1 | 12/2007 |
| EP | 1935420 | A1 | 6/2008 |
| GB | 1077711 | A | 8/1967 |
| JP | 6092945 | | 4/1994 |
| JP | 7157681 | | 6/1995 |
| JP | 09151179 | | 6/1997 |
| JP | 2002179572 | A | 6/2002 |
| JP | 2003096058 | A | 4/2003 |
| JP | 2003300884 | A | 10/2003 |
| JP | 2005206503 | A | 8/2005 |
| JP | 2005239670 | A | 9/2005 |
| JP | 2005272321 | A | 10/2005 |
| JP | 2007140188 | A | 6/2007 |
| JP | 2007254409 | A | 10/2007 |
| JP | 2009110842 | A | 5/2009 |
| JP | 2011519374 | A | 7/2011 |
| WO | 9207838 | A1 | 5/1992 |
| WO | 9307128 | A1 | 4/1993 |
| WO | 9313103 | A1 | 7/1993 |
| WO | 9531440 | A1 | 11/1995 |
| WO | 9614297 | A1 | 5/1996 |
| WO | 9623787 | A1 | 8/1996 |
| WO | 9637494 | A1 | 11/1996 |
| WO | 9707789 | A1 | 3/1997 |
| WO | 9736605 | A1 | 10/1997 |
| WO | 9822462 | A1 | 5/1998 |
| WO | 9857940 | A1 | 12/1998 |
| WO | 9905125 | A1 | 2/1999 |
| WO | 9906395 | A1 | 2/1999 |
| WO | 0009107 | A2 | 2/2000 |
| WO | 0100595 | A1 | 1/2001 |
| WO | 0113917 | A1 | 3/2001 |
| WO | 0144200 | A2 | 6/2001 |
| WO | 0155063 | A1 | 8/2001 |
| WO | 0206244 | A1 | 1/2002 |
| WO | 0206277 | A1 | 1/2002 |
| WO | 0222572 | A2 | 3/2002 |
| WO | 03043988 | A1 | 5/2003 |
| WO | 03057673 | A1 | 7/2003 |
| WO | 03093261 | A1 | 11/2003 |
| WO | 03097608 | A2 | 11/2003 |
| WO | 2004004722 | A1 | 1/2004 |

(56) References Cited

FOREIGN PATENT DOCUMENTS

| | | |
|---|---|---|
| WO | 2004009559 A2 | 1/2004 |
| WO | 2004014859 A2 | 2/2004 |
| WO | 2004046137 A1 | 6/2004 |
| WO | 2004056745 A2 | 7/2004 |
| WO | 2004089896 A1 | 10/2004 |
| WO | 2004094375 A2 | 11/2004 |
| WO | 2005000845 A2 | 1/2005 |
| WO | 2005086700 A2 | 9/2005 |
| WO | 2005108361 A1 | 11/2005 |
| WO | WO 2005/108360 * | 11/2005 |
| WO | 2005113525 A1 | 12/2005 |
| WO | 2005116002 A2 | 12/2005 |
| WO | 2006002349 A1 | 1/2006 |
| WO | 2006003494 A2 | 1/2006 |
| WO | 2006014357 A1 | 2/2006 |
| WO | 2006017443 A2 | 2/2006 |
| WO | 2006024627 A2 | 3/2006 |
| WO | 2006024628 A1 | 3/2006 |
| WO | 2006031715 A2 | 3/2006 |
| WO | 2006040329 A1 | 4/2006 |
| WO | 2006044174 A2 | 4/2006 |
| WO | 2006049952 A1 | 5/2006 |
| WO | 2006066924 A2 | 6/2006 |
| WO | 2006066948 A1 | 6/2006 |
| WO | 2006090792 A1 | 8/2006 |
| WO | 2006104280 A1 | 10/2006 |
| WO | 2006109056 A1 | 10/2006 |
| WO | 2007008529 A2 | 1/2007 |
| WO | 2007022371 A2 | 2/2007 |
| WO | 2007048595 A1 | 5/2007 |
| WO | 2007051810 A2 | 5/2007 |
| WO | 2007061661 A2 | 5/2007 |
| WO | 2007068330 A1 | 6/2007 |
| WO | 2007076055 A2 | 7/2007 |
| WO | 2007079186 A2 | 7/2007 |
| WO | 2007081569 A1 | 7/2007 |
| WO | 2007081570 A2 | 7/2007 |
| WO | 2007081571 A2 | 7/2007 |
| WO | 2007084314 A2 | 7/2007 |
| WO | 2007101270 A1 | 9/2007 |
| WO | 2007103719 A2 | 9/2007 |
| WO | 2007109456 A2 | 9/2007 |
| WO | 2007118185 A2 | 10/2007 |
| WO | 2007123853 A2 | 11/2007 |
| WO | 2007124254 A2 | 11/2007 |
| WO | 2007124329 A1 | 11/2007 |
| WO | 2007124337 A1 | 11/2007 |
| WO | 2007127693 A1 | 11/2007 |
| WO | 2007127763 A2 | 11/2007 |
| WO | 2008000951 A2 | 1/2008 |
| WO | 2008024497 A2 | 2/2008 |
| WO | 2008031227 A1 | 3/2008 |
| WO | 2008036715 A1 | 3/2008 |
| WO | 2008046578 A2 | 4/2008 |
| WO | 2008046758 A2 | 4/2008 |
| WO | 2008059948 A1 | 5/2008 |
| WO | 2008106128 A2 | 9/2008 |
| WO | 2008118332 A2 | 10/2008 |
| WO | 2009017664 A2 | 2/2009 |
| WO | 2009017671 A1 | 2/2009 |
| WO | 2009020140 A1 | 2/2009 |
| WO | 2009061498 A1 | 5/2009 |
| WO | 2009063061 A2 | 5/2009 |
| WO | 2009075835 A1 | 6/2009 |
| WO | 2009088997 A1 | 7/2009 |
| WO | 2009094169 A1 | 7/2009 |
| WO | 2009100872 A1 | 8/2009 |
| WO | 2009102428 A2 | 8/2009 |
| WO | 2009102460 A2 | 8/2009 |
| WO | 2009107664 A1 | 9/2009 |
| WO | 2009108332 A1 | 9/2009 |
| WO | 2009117109 A1 | 9/2009 |
| WO | 2009131669 A2 | 10/2009 |
| WO | 2009134384 A1 | 11/2009 |
| WO | 2009134387 A1 | 11/2009 |
| WO | 2009134392 A1 | 11/2009 |
| WO | 2009134400 A1 | 11/2009 |
| WO | 2009138386 A2 | 11/2009 |
| WO | 2010010149 A1 | 1/2010 |
| WO | 2010010150 A1 | 1/2010 |
| WO | 2010010157 A2 | 1/2010 |
| WO | 2010010174 A1 | 1/2010 |
| WO | 2010011314 A1 | 1/2010 |
| WO | 2010023161 A1 | 3/2010 |
| WO | 2010046445 A2 | 4/2010 |
| WO | 2010089303 A1 | 8/2010 |
| WO | 2010091067 A2 | 8/2010 |
| WO | 2010104830 A1 | 9/2010 |
| WO | 2010127237 A2 | 11/2010 |
| WO | 2010139673 A1 | 12/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011056737 A1 | 5/2011 |
| WO | 2011057054 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

ChemAbstract—Accession #: 1969:68280. Maillard, J. et al., "Spiroheterocyclic cycloalkane compounds II. Synthesis of 6-substituted-tetrahydro-2H-1, 3-oxazine-2-ones." Chima Therapeutica, 3(5), 1968, pp. 321-324.

ChemAbstract—Accession #: 1978:563520. Slyusarenko, E.I., et al., Syntheses based on thionylamides. IV. 2-alkoxy-5,6-dihydro-1,3-oxazines. Zhurnal Organicheskoi Chimii, 14(5), 1979, p. 1093.

ChemAbstract—Accession #: 1983:595067. Saitkulova, F.G. et al., "Syntheses involving bromozinc alcholates of carboxylic acid esters". Khimiya Elementoorganicheskikh Soedinii, vol. 1982, 1982, pp. 22-26.

ChemAbstract—Accession #: 1983:89280. Lapkin, I.I. et al., "Synthesis of 1,3-oxazine-2,4-diones." Zhurnal Organicheskoi Khimii, vol. 18, No. 11, 1982, p. 2468.

ChemAbstract—Accession No. 2007:1110441 Abstract, Chemical Abstract Service, Columbus, Ohio, Fukushima, H. et al., "Preparation of imidazolidinone derivatives as 11.beta.-HSD1 inhibitors". JP2007254409 (Taisho Pharmaceutical Co. Ltd., Japan, Oct. 4, 2007. (Attached is a machine translation of the ChemAbstract and a Derwent World Patents Index file record).

ChemAbstract: CAS: 150:214405, Accession #: 2009:140024. Claremon, D.A., et al., Preparation of 1,3-oxazinan-2-one dervatives as inhibitors of 11-beta-hydroxysteroid dehydrogenase type1. 2009.

Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.

Evans, B.E. et al., "Orally active, nonpeptide osytocin antagonists". Journal of Medicinal Chemistry, American Chem. Soc., Vo. 35, No. 21, Oct. 15, 1992, p. 3919-3927.

Fandrick, D.R. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.

Goubet, F. et al., "Conversion of a Thiohydantoin to the Corresponding Hydantoin via a Ring-Opening/Ring Closure Mechanism". Tetrahedron Letters, Elsevier, Amsterdam, vol. 37. No. 43, Oct. 21, 1996. p. 7727-7730.

Harno, E. et al., "Will treating diabetes with 11-beta-HSD1 inhibitors affect the HPA axis?" Trends in Endocrinology and Metabolism, Elsevier Science Publishing, NY, NY, USm, vol. 21, No. 10, Oct. 1, 2010, pp. 619-627.

International Search Report and Written Opinion for PCT/EP2009/059496 mailed Nov. 17, 2009.

International Search Report and Written Opinion for PCT/EP2011/060386 mailed Sep. 16, 2011.

Kashima, C. et al., "Preparation of N-Aryl-2,4-diaminopentanes by the Ring Opening Reaction of 1-Aryl-3,4,5,6-tetradydro-2-(1H)pyrimidinones". Journal of Heterocyclic Chemistry, vol. 18, 1981, p. 1595-1596.

(56) References Cited

OTHER PUBLICATIONS

Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.

Muehlstadt, M. et al., "Cyclisation reactions of beta,gamma-unsaturated derivatives of carbonis acid. IX" Journal Fuer Praktische Chemi, vol. 328, 1986, p. 163-172.

Rosenstock, J. et al., "The 11-beta-hydroxysteroid Dehydrogenase Type 1 inhibitor INCB13739 Improves Hyperglycemia in Patients with Type 2 Diabetes Inadequately Controlled by Metformin Monotherapy." Diabetes Care, vol. 33, No. 7, Jul. 2010, pp. 1516-1522.

Schoellkopf, U. et al., "Umsetzungen Alphametallierter Isocyanide Mit Eigigen 1,3-Dipolen" English: "Reactions of alpha-metalated osicyanidews with some 1,3-dipoles", Liebigs Annalen Der Chemie, Verlag Chemi, GmbH, Weinheim, DE, vol. 4, Jan. 1, 1980, p. 600-610.

Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.

Shibata, I. et al., "Cycloaddition of Oxetanes with Heterocumulenes Catalyzed by Organotin Iodine-Lewis Base Complex". Journal of Heterocyclic Chemistry, vol. 24, 1987, p. 361-363.

Tadayyon M. et al., "Insulin sensitisation in the treatment of Type 2 diabetes." Expert Opinion on Investigational Drugs, Ashley Publications, Ltd., London, GB, vol. 12, n. 3, Mar. 1, 2003, pp. 307-324.

Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.

Tamaru, Y. et al., "Urea as the Most Reactive and Versatile Nitrogen Nucleophile for the Palladium (2+)-Catalyzed Cyclization of Unsaturated Amines," J. Am. Chem. Soc., 1988, 110, 3994-4002.

Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.

Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.

Worthy, A.D. et al., "Regioselective Hydroformylation of Sulfonamides using a Scaffolding Ligand". Organic Letters, 2009, vol. 11, No. 13—p. 2764-2767.

* cited by examiner

AZASPIROHEXANONES

FIELD OF THE INVENTION

The present invention relates to azaspirohexanones and their use as inhibitors of 11-beta-hydroxysteroid dehydrogenase 1 (11beta-HSD1), to pharmaceutical compositions containing said compounds as well as their use for the treatment of metabolic disorders like metabolic syndrome, diabetes, obesity, and dyslipidemia. In addition, the invention relates to processes for preparing a pharmaceutical composition as well as a compound according to the invention.

BACKGROUND OF THE INVENTION

In the literature, compounds which have an inhibitory effect on the enzyme 11-beta-hydroxysteroid dehydrogenase 1 (11beta-HSD1) are proposed for the treatment of the metabolic syndrome, in particular diabetes type 2, obesity, and dyslipidemia. For example WO 09/102,460 discloses inhibitors of 11-beta-hydroxysteroid dehydrogenase 1 and their use in the treatment of such diseases.

SUMMARY OF THE INVENTION

It has now been found that compounds of the present invention according to general formula I are effective inhibitors of 11-beta-hydroxysteroid dehydrogenase 1.

A further aspect of the present invention is to provide new pharmaceutical compositions which are suitable for the prevention and/or treatment of metabolic disorders.

A further aspect of the invention relates to the physiologically acceptable salts of the compounds of general formula I according to this invention with inorganic or organic acids.

In a further aspect this invention relates to pharmaceutical compositions, containing at least one compound of general formula I or a physiologically acceptable salt according to the invention, optionally together with one or more inert carriers and/or diluents.

In a further aspect this invention relates to the compounds according to general formula I or the physiologically acceptable salts thereof for treatment or prevention of diseases or conditions which can be influenced by inhibiting the enzyme 11-beta-hydroxysteroid dehydrogenase 1, such as metabolic disorders.

In a further aspect this invention relates to the use of at least one compound according to general formula I or a physiologically acceptable salt thereof for preparing a pharmaceutical composition which is suitable for the treatment or prevention of diseases or conditions which can be influenced by inhibiting the enzyme 11-beta-hydroxysteroid dehydrogenase 1, such as metabolic disorders.

Other aims of the present invention will become apparent to the skilled man directly from the foregoing and following remarks.

DETAILED DESCRIPTION OF THE INVENTION

In a first aspect the present invention relates to compounds of general formula I

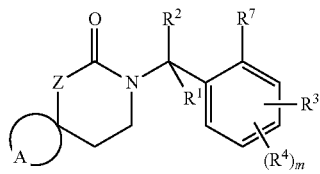

I wherein
R$^1$ is selected from the group R$^{1a}$ consisting of
 H, C$_{1-6}$-alkyl-, C$_{3-6}$-cycloalkyl-, C$_{2-6}$-alkenyl- and C$_{2-6}$-alkynyl-,
  wherein one —CH$_2$— group of the above mentioned C$_{1-6}$-alkyl-group or C$_{3-6}$-cycloalkyl-group is optionally replaced by —O—, and
  wherein above mentioned C$_{1-6}$-alkyl-, C$_{2-6}$-alkenyl-, C$_{2-6}$-alkynyl- and C$_{3-6}$-cycloalkyl-groups may optionally be substituted with one to three F;
R$^2$ is selected from the group R$^{2a}$ consisting of
 H and C$_{1-4}$-alkyl-,
  wherein above mentioned C$_{1-4}$-alkyl-group may optionally be substituted with one to three F, or,
 R$^{1a}$ and R$^{2a}$ form together a C$_{2-6}$-alkylene bridge,
  wherein, in case the before mentioned alkylene group contains more than 2-CH$_2$— groups, one —CH$_2$— group may optionally be replaced by —O—;
R$^3$ is selected from the group R$^{3a}$ consisting of

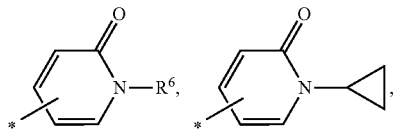

H, F, phenyl, naphthyl, pyrrolyl, furanyl, thienyl, tetrazolyl, pyridyl, indolyl, benzofuranyl, benzothiophenyl, quinolinyl, isoquinolinyl,
 wherein in the pyrrolyl, furanyl, thienyl, and pyridyl group 1 or 2 CH groups optionally may be replaced by N, and
 wherein in the indolyl, benzofuranyl, benzothiophenyl, quinolinyl, and isoquinolinyl group 1 to 3 CH groups optionally may be replaced by N, and
 wherein all above-mentioned groups may optionally be substituted with one or two R$^{10}$ which may be identical or different;
R$^4$ is selected independently of each other from the group R$^{4a}$ consisting of
 H, halogen, C$_{1-6}$-alkyl-, C$_{3-6}$-cycloalkyl-, HO—, C$_{1-4}$-alkyl-O—, HO—O$_{2-4}$-alkyl-O—, H$_3$CO—C$_{2-4}$-alkyl-O—, NC—C$_{1-4}$-alkyl-O—, C$_{3-6}$-cycloalkyl-O—, tetrahydrofuranyl, tetrahydrofuranyl-O—, tetrahydropyranyl-, tetrahydropyranyl-O—, NC—, HOOC—, C$_{1-4}$-alkyl-OC(O)—, (R$^6$)$_2$N—C(O)—, C$_{1-4}$-alkyl-S—, C$_{1-4}$-alkyl-S(O)— and C$_{1-4}$-alkyl-S(O)$_2$—,
  wherein above mentioned C$_{1-6}$-alkyl-, C$_{1-4}$-alkyl-O— and C$_{3-6}$-cycloalkyl-groups may optionally be substituted with one to three F, and
  wherein above mentioned C$_{1-6}$-alkyl- and C$_{3-6}$-cycloalkyl-groups may optionally be monosubstituted with HO—, H$_3$CO—, NC—, HOOC—, C$_{1-4}$-alkyl-OC(O)—, (R$^6$)$_2$N—C(O)—, C$_{1-4}$-alkyl-S—, C$_{1-4}$-alkyl-S(O)— or C$_{1-4}$-alkyl-S(O)$_2$—, and
  wherein two of the aforementioned groups R$^{4a}$, provided that they are attached to adjacent carbon atoms of the phenyl ring in formula I may form together a C$_{3-6}$-alkylene bridge,
   wherein one or two —CH$_2$-groups of the aforementioned C$_{3-5}$-alkylene bridge may optionally be replaced by any of the groups selected form —N(R$^N$)—, —O—, and —C(O)—, and
  which may optionally be substituted with one or two groups independently selected from F and H$_3$C—, and wherein two of the aforementioned groups $R^{4a}$, provided that they are attached to adjacent carbon atoms of the phenyl ring in formula I may form together with the carbon atoms to which they are attached a benzo, pyrido, pyrimido, pyrazino, pyridazino, pyrazolo, imidazo, triazolo, oxazolo, thiazolo, isoxazolo, or isothiazolo ring, wherein each of the aforementioned benzo, pyrido, pyrimido, pyrazino, pyridazino, pyrazolo, imidazo, triazolo, oxazolo, thiazolo, isoxazolo, or isothiazolo rings may optionally be substituted with one or two substituents independently from each other selected from halogen, $C_{1-4}$-alkyl-, $FH_2C$—, $F_2HC$—, $F_3C$—, $H_2N$—, $C_{1-4}$-alkyl-NH—, $(C_{1-4}$-alkyl$)_2$N—, HO—, $C_{1-4}$-alkyl-O—, $FH_2CO$—, $F_2HCO$—, $F_3CO$— and NC—;

A is selected from the group $A^a$ consisting of

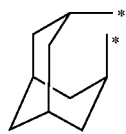

and —$(CH_2)_{4-6}$—, wherein one —$CH_2$—$CH_2$— group may optionally be replaced by a —CH=CH— group, and wherein the above mentioned groups may optionally be substituted with one to four $R^5$;

$R^5$ is selected independently from each other from the group $R^{5a}$ consisting of halogen, NC—, $(R^6)_2$N—, HO—, O=, $C_{1-6}$-alkyl-, $C_{3-6}$-cycloalkyl-, $C_{2-6}$-alkenyl-, $C_{2-6}$-alkynyl-, HOOC—, $C_{1-4}$-alkyl-OC(O)—, $(R^6)_2$N—C(O)—, $C_{1-4}$-alkyl-S—, $C_{1-4}$-alkyl-S(O)— and $C_{1-4}$-alkyl-S(O)$_2$—, wherein the $C_{1-6}$-alkyl- and $C_{3-6}$-cycloalkyl-, $C_{2-6}$-alkenyl and $O_{2-6}$-alkynyl-groups may optionally be substituted independently from each other by one to three F and/or one substituent selected from the group consisting of F, Cl, NC—, $(R^6)_2$N—, HO—, O=, $C_{1-4}$-alkyl-, HOOC—, $C_{1-4}$-alkyl-OC(O)—, $(R^6)_2$N—C(O)—, $C_{1-4}$-alkyl-S—, $C_{1-4}$-alkyl-S(O)— and $C_{1-4}$-alkyl-S(O)$_2$—, and wherein two of the aforementioned groups $R^{5a}$ may form together a —$(CH_2)_{4-6}$-alkylene bridge, wherein the aforementioned —$(CH_2)_{4-6}$-alkylene bridge may optionally be substituted with one or two groups selected independently from each other from the group consisting of F, $H_3C$—, HO—, and $H_3C$—O—, and wherein one or two —$CH_2$— groups of said $(CH_2)_{4-6}$-alkylene bridge may optionally be replaced by —O—;

$R^6$ is selected independently of each other from the group $R^{6a}$ consisting of H and $C_{1-4}$-alkyl-;

$R^7$ is selected from the group $R^{7a}$ consisting of

H, halogen, $C_{1-4}$-alkyl-, $F_3C$—, HO—, $C_{1-4}$-alkyl-O—, NC—, or the aforementioned group $R^{7a}$ may form together with $R^1$ a —$(CH_2)_{2-4}$-alkylene bridge, wherein the aforementioned —$(CH_2)_{2-4}$-alkylene bridge may optionally be substituted with one or two groups selected independently from each other from the group consisting of F, $H_3C$—, HO—, and $H_3C$—O—, and wherein one —$CH_2$— group may optionally be replaced by —O—;

$R^{10}$ is selected independently of each other from the group $R^{10a}$ consisting of halogen, $C_{1-4}$-alkyl-, $C_{3-6}$-cycloalkyl-, $FH_2C$, $F_2HC$—, $F_3C$—, NC—, $H_2N$—C(O)—, $C_{1-4}$-alkyl-NH—C(O)—, $(C_{1-4}$-alkyl$)_2$N—C(O)—, $HO_2O$—, $C_{1-4}$-alkyl-O—C(O)—, $O_2N$—, $H_2N$—, $C_{1-4}$-alkyl-NH—, $(C_{1-4}$-alkyl$)_2$N—, $H_3CO(O)NH$—, $H_3C$—S(O)$_2$—NH—, HO—, $C_{1-4}$-alkyl-O—, $FH_2CO$—, $F_2HC$—O—, $F_3C$—O—, $H_3C$—S—, $H_3C$—S(O)—, $H_3C$—S(O)$_2$—, wherein aforementioned $C_{1-4}$-alkyl- and $C_{3-6}$-cycloalkyl-groups may optionally be substituted with 1 or 2 groups selected independently from each other from the group consisting of F, $H_3C$—, $H_3C$—O—, NC—, $H_2N$—C(O)—, $C_{1-4}$-alkyl-NH—C(O)—, $(C_{1-4}$-alkyl$)_2$N—C(O)— and HO—;

Z is selected from the group $Z^a$ consisting of

—$CH_2$—, —N($R^6$)— and —O—;

$R^N$ is selected independently of each other from the group $R^{Na}$ consisting of H, $C_{1-6}$-alkyl-, $C_{3-6}$-cycloalkyl-, $C_{3-6}$-alkenyl-, $C_{3-6}$-alkynyl-, $C_{1-4}$-alkyl-C(O)—, $C_{3-6}$-cycloalkyl-C(O)—, $H_2N$—C(O)—, $C_{1-4}$-alkyl-NH—C(O)—, $(C_{1-4}$-alkyl$)_2$N—C(O)—, $C_{1-4}$-alkyl-O—C(O)—, $C_{1-4}$-alkyl-S(O)$_2$—, $C_{3-6}$-cycloalkyl-S(O)$_2$—, wherein the above mentioned $C_{1-6}$-alkyl-, $C_{3-6}$-alkenyl- and $C_{3-6}$-alkynyl-groups may optionally be mono- di- or trisubstituted with fluorine;

m denotes 0, 1, 2 or 3;

the tautomers thereof, the stereoisomers thereof, the mixtures thereof, and the salts thereof.

Unless otherwise stated, the groups, residues, and substituents, particularly $R^1$, $R^2$, $R^3$, $R^4$, $R^5$, $R^6$, $R^7$, $R^{10}$, $R^N$, A, Z and m are defined as above and hereinafter. If residues, substituents, or groups occur several times in a compound they may have the same or different meanings. Some preferred meanings of groups and substituents of the compounds according to the invention will be given hereinafter.

In a further embodiment of the present invention $R^1$ is selected from the group $R^{1b}$ consisting of H, $C_{1-4}$-alkyl-, $FH_2C$—$F_2HC$—, $F_3C$—, $H_3C$—O—$C_{1-2}$-alkyl- and $C_{3-6}$-cycloalkyl-.

In a further embodiment of the present invention $R^1$ is selected from the group $R^{1c}$ consisting of $C_{1-4}$-alkyl-, $HF_2C$—, $F_3C$— and $C_{3-4}$-cycloalkyl-.

In a further embodiment of the present invention $R^1$ is selected from the group $R^{1d}$ consisting of $H_3C$—, $H_3C$—$CH_2$— and cyclopropyl-.

In a further embodiment of the present invention $R^2$ is selected from the group $R^{2b}$ consisting of H and $H_3C$—.

In a further embodiment of the present invention $R^2$ is selected from the group $R^{2c}$ consisting of

H.

In a further embodiment of the present invention
R³ is selected from the group R^{3b} consisting of

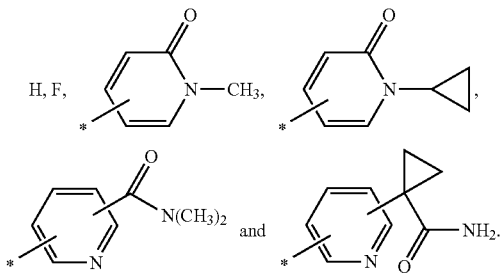

In a further embodiment of the present invention
R³ is selected from the group R^{3c} consisting of

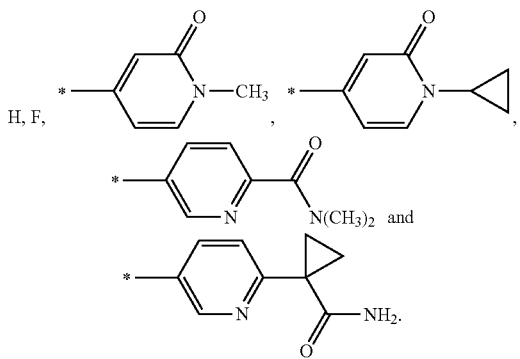

In a further embodiment of the present invention
R³ is selected from the group R^{3d} consisting of
H.

In a further embodiment of the present invention
R⁴ is selected independently of each other from the group R^{4b} consisting of
H, F, Cl, Br, $C_{1-4}$-alkyl-, $C_{3-5}$-cycloalkyl-, HO—, $C_{1-4}$-alkyl-O—, HO—$C_{2-4}$-alkyl-O—, $H_3CO$—$C_{2-4}$-alkyl-O—, NC—$C_{1-4}$-alkyl-O—, $C_{3-5}$-cycloalkyl-O—, tetrahydrofuranyl-O—, tetrahydropyranyl-O—, NC—, HOOC—, $C_{1-4}$-alkyl-OC(O)—, $(R^6)_2N$—C(O)—, $C_{1-3}$-alkyl-S—, $C_{1-3}$-alkyl-S(O)— and $C_{1-3}$-alkyl-S(O)_2—,
  wherein above mentioned $C_{1-4}$-alkyl- and $C_{1-4}$-alkyl-O-groups may optionally be substituted with one to three F, and
  wherein above mentioned $C_{1-4}$-alkyl- and $C_{3-5}$-cycloalkyl-groups may optionally be monosubstituted with HO—, $H_3CO$—, NC—, $(R^6)_2N$—C(O)—, or $C_{1-3}$-alkyl-S(O)_{2-3}
  and
  wherein two of the aforementioned groups R^{4b} provided that they are attached to adjacent carbon atoms of the phenyl ring in formula I may form together a $C_{3-5}$-alkylene bridge,
    wherein one or two —CH_2—groups of the aforementioned $C_{3-5}$-alkylene bridge may optionally be replaced by —O—, and
    which may optionally be substituted with one or two F,
  and
  wherein two of the aforementioned groups R^{4b}, provided that they are attached to adjacent carbon atoms of the phenyl ring in formula I may form together with the carbon atoms to which they are attached a benzo, pyrido, pyrimido, pyrazino, pyridazino, pyrazolo, imidazo, triazolo, oxazolo, thiazolo, isoxazolo or isothiazolo ring,
    wherein each of the aforementioned benzo, pyrido, pyrimido, pyrazino, pyridazino, pyrazolo, imidazo, triazolo, oxazolo, thiazolo, isoxazolo or isothiazolo rings may optionally be substituted with one or two substituents independently from each other selected from F, Cl, Br, $C_{1-4}$-alkyl-, $FH_2C$—, $F_2HC$—, $F_3C$—, HO—, $C_{1-4}$-alkyl-O—, $FH_2CO$—, $F_2HCO$—, $F_3CO$— and NC—.

In a further embodiment of the present invention
R⁴ is selected independently of each other from the group R^{4c} consisting of
H, F, Cl, Br, $C_{1-4}$-alkyl-, $C_{3-4}$-cycloalkyl-, $C_{1-4}$-alkyl-O—, HO—$C_{2-4}$-alkyl-O—, $H_3CO$—$C_{2-4}$-alkyl-O—, NC—$C_{1-4}$-alkyl-O—, $C_{3-5}$-cycloalkyl-O—, tetrahydrofuranyl-O—, tetrahydropyranyl-O—, NC—, $(R^6)_2N$—C(O)—,
  wherein above mentioned $C_{1-4}$-alkyl- and $C_{1-4}$-alkyl-O-groups may optionally be substituted with one to three F, and wherein above mentioned $C_{1-4}$-alkyl-groups may optionally be monosubstituted with HO—, $H_3CO$—, NC—, $(R^6)_2N$—C(O)—, and
  wherein two of the aforementioned groups R^{4c} provided that they are attached to adjacent carbon atoms of the phenyl ring in formula I may form together with these carbon atoms a benzo ring,
    wherein the aforementioned benzo ring may optionally be substituted with one substituent selected from F, Cl, $H_3C$—, $FH_2C$—, $F_2HC$—, $F_3C$—, $H_3CO$—, $FH_2CO$—, $F_2HCO$—, $F_3CO$— and NC—.

In a further embodiment of the present invention
R⁴ is selected independently of each other from the group R^{4d} consisting of
H, F, Cl, Br, $C_{1-4}$-alkyl-, cyclopropyl-, $F_2HC$—, $F_3C$—, $H_3CO$—, $F_2HCO$— or $F_3CO$—, and
wherein two of the aforementioned groups R^{4d} provided that they are attached to adjacent carbon atoms of the phenyl ring in formula I may form together with these carbon atoms a benzo ring.

In a further embodiment of the present invention
A is selected from the group A^b consisting of
—(CH_2)_{4-6}— and

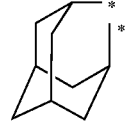

wherein the above mentioned groups may optionally be substituted with one or two R⁵.

In a further embodiment of the present invention
A is selected from the group A^c consisting of
—(CH_2)_{4-5}— and

wherein the above mentioned groups may optionally be substituted with one or two R⁵.

In a further embodiment of the present invention
A is selected from the group $A^d$ consisting of
—(CH$_2$)$_5$—
  wherein the above mentioned group may optionally be substituted with one or two $R^5$.

In a further embodiment of the present invention
$R^5$ is selected independently from each other from the group $R^{5b}$ consisting of
F, NC—, (R$^6$)$_2$N—, HO—, O=, $C_{1-6}$-alkyl-, HOOC—, $C_{1-4}$-alkyl-OC(O)—, (R$^6$)$_2$N—C(O)—, $C_{1-3}$-alkyl-S—, $C_{1-3}$-alkyl-S(O)— and $C_{1-3}$-alkyl-S(O)$_2$—,
  wherein above mentioned $C_{1-6}$-alkyl-group may optionally be substituted independently from each other by one or two substituents selected independently from each other from the group consisting of F, NC—, (R$^6$)$_2$N—, HO—, O=, $C_{1-4}$-alkyl-, HOOC—, $C_{1-4}$-alkyl-OC(O)—, (R$^6$)$_2$N—C(O)—, $C_{1-3}$-alkyl-S—, $C_{1-3}$-alkyl-S(O)— and $C_{1-3}$-alkyl-S(O)$_2$—, and in case wherein two of the aforementioned groups $R^{5b}$ are connected to the same carbon atom, they may form together a (CH$_2$)$_{4-6}$-alkylene bridge,
    wherein said (CH$_2$)$_{4-6}$-alkylene bridge may optionally be substituted with one or two groups selected independently from each other from the group consisting of H$_3$C—, HO—, and H$_3$C—O—, and
    wherein one or two —CH$_2$— groups of said (CH$_2$)$_{4-6}$-alkylene bridge may optionally be replaced by —O—.

In a further embodiment of the present invention
$R^5$ is selected independently from each other from the group $R^{5c}$ consisting of
NC—, HO—, O=, $C_{1-3}$-alkyl-, HOOC—, $C_{1-3}$-alkyl-OC(O)—, (R$^6$)$_2$N—C(O)—,
  wherein the $C_{1-3}$-alkyl-group may optionally be monosubstituted by a substituent selected from the group consisting of NC—, HO—, HOOC—, $C_{1-3}$-alkyl-OC(O)—, (R$^6$)$_2$N—C(O)—, and
  in case wherein two of the aforementioned groups $R^{5d}$ are connected to the same carbon atom, they may form together a —O(CH$_2$)$_{2-3}$O— bridge,
    wherein the aforementioned bridge may optionally be substituted with one or two H$_3$C-groups.

In a further embodiment of the present invention
$R^5$ is selected independently from each other from the group $R^{5d}$ consisting of
HO—, O=, H$_3$C—, H$_2$N—C(O)— and HO—CH$_2$—.

In a further embodiment of the present invention
$R^6$ is selected independently of each other from the group $R^{6b}$ consisting of
H$_3$C— and H.

In a further embodiment of the present invention
$R^6$ is selected independently of each other from the group $R^{6c}$ consisting of
H.

In a further embodiment of the present invention
$R^7$ is selected from the group $R^{7b}$ consisting of
H, F, Cl, Br, $C_{1-3}$-alkyl-, F$_3$C—, HO—, $C_{1-3}$-alkyl-O— and NC—,
or
the aforementioned group $R^{7b}$ may form together with $R^1$ a —(CH$_2$)$_{2-3}$-alkylene bridge.

In a further embodiment of the present invention
$R^7$ is selected from the group $R^{7c}$ consisting of
H, F, Cl, and H$_3$C—,
or
the aforementioned group $R^{7c}$ may form together with $R^1$ a —(CH$_2$)$_2$-alkylene bridge.

In a further embodiment of the present invention
$R^{10}$ is selected from the group $R^{10b}$ consisting of
H and F.

In a further embodiment of the present invention
$R^{10}$ is selected independently of each other from the group $R^{10b}$ consisting of
F, Cl, $C_{1-3}$-alkyl-, cyclopropyl-, F$_2$HC—, F$_3$C—, NC—, H$_2$N—C(O)—, $C_{1-3}$-alkyl-NH—C(O)—, ($C_{1-3}$-alkyl)$_2$N—C(O)—, HO—, $C_{1-3}$-alkyl-O—, F$_2$HC—O—, F$_3$C—O—.

In a further embodiment of the present invention
$R^{10}$ is selected independently of each other from the group $R^{10c}$ consisting of
F, Cl, H$_3$C—, F$_2$HC—, F$_3$C—, NC—, H$_2$N—C(O)—, H$_3$C—NH—C(O)—, (H$_3$C)$_2$N—C(O)—, HO—, H$_3$C—O, F$_2$HC—O—, F$_3$C—O—.

In a further embodiment of the present invention
Z is selected from the group $Z^b$ consisting of
—CH$_2$—, —NH—, and —O—.

In a further embodiment of the present invention
Z is selected from the group $Z^c$ consisting of
—NH— and —O—.

In a further embodiment of the present invention
Z is selected from the group $Z^d$ consisting of
—O—.

In a further embodiment of the present invention
$R^N$ is selected independently of each other from the group $R^{Nb}$ consisting of
H, $C_{1-4}$-alkyl-, $C_{3-5}$-cycloalkyl-, $C_{1-4}$-alkyl-C(O)—, $C_{3-6}$-cycloalkyl-C(O)—, $C_{1-4}$-alkyl-S(O)$_2$—, $C_{3-5}$-cycloalkyl-S(O)$_2$—.

In a further embodiment of the present invention
$R^N$ is selected independently of each other from the group $R^{Nc}$ consisting of
H, H$_3$C—, H$_3$C—C(O)—, H$_3$C—S(O)$_2$—.

In a further embodiment m is preferably 0, in another embodiment, m is preferably 1, in yet another embodiment m is preferably 2.

Each $R^{1x}$, $R^{2x}$, $R^{3x}$, $R^{4x}$, $R^{5x}$, $R^{6x}$, $R^{7x}$, $R^{Nx}$, $R^{10x}$, $A^x$, $Z^x$ and m represents a characterized, individual embodiment for the corresponding substituent as described above. Thus given the above definitions, preferred individual embodiments of the first aspect of the invention are fully characterized by the term ($R^{1x}$, $R^{2x}$, $R^{3x}$, $R^{4x}$, $R^{5x}$, $R^{6x}$, $R^{7x}$, $R^{Nx}$, $R^{10x}$, $A^x$, $Z^x$ and m), wherein for each index x an individual figure is given that ranges from "a" to the highest letter given above. Indices x and m vary independently from each other. All individual embodiments described by the term in parentheses with full permutation of the indices x and m, referring to the definitions above, shall be comprised by the present invention.

The following Table 1 shows, exemplarily and in the order of increasing preference from the first line to the last line, such embodiments E-1 to E-20 of the invention that are considered preferred. This means that embodiment E-20, represented by the entries in the last row of Table 1, is the most preferred embodiment.

TABLE 1

Preferred embodiments E-1 to E-20 of the invention

|  | $R^1$ | $R^2$ | $R^3$ | $R^4$ | $R^5$ | $R^6$ | $R^7$ | $R^N$ | $R^{10}$ | A | Z | m |
|---|---|---|---|---|---|---|---|---|---|---|---|---|
| E-1 | $R^{1b}$ | $R^{2b}$ | $R^{3a}$ | $R^{4a}$ | $R^{5b}$ | $R^{6a}$ | $R^{7a}$ | $R^{Nb}$ | $R^{10a}$ | $A^b$ | $Z^b$ | 0-3 |
| E-2 | $R^{1b}$ | $R^{2b}$ | $R^{3a}$ | $R^{4b}$ | $R^{5b}$ | $R^{6a}$ | $R^{7a}$ | —* | $R^{10b}$ | $A^b$ | $Z^b$ | 0-3 |

TABLE 1-continued

Preferred embodiments E-1 to E-20 of the invention

| | $R^1$ | $R^2$ | $R^3$ | $R^4$ | $R^5$ | $R^6$ | $R^7$ | $R^N$ | $R^{10}$ | A | Z | m |
|---|---|---|---|---|---|---|---|---|---|---|---|---|
| E-3 | $R^{1b}$ | $R^{2b}$ | $R^{3a}$ | $R^{4b}$ | $R^{5b}$ | $R^{6a}$ | $R^{7a}$ | —* | $R^{10c}$ | $A^b$ | $Z^b$ | 0-3 |
| E-4 | $R^{1b}$ | $R^{2b}$ | $R^{3b}$ | $R^{4b}$ | $R^{5b}$ | $R^{6a}$ | $R^{7a}$ | —* | —* | $A^b$ | $Z^b$ | 0-3 |
| E-5 | $R^{1b}$ | $R^{2c}$ | $R^{3b}$ | $R^{4b}$ | $R^{5b}$ | $R^{6a}$ | $R^{7a}$ | —* | —* | $A^c$ | $Z^c$ | 0-3 |
| E-6 | $R^{1b}$ | $R^{2c}$ | $R^{3c}$ | $R^{4c}$ | $R^{5c}$ | $R^{6b}$ | $R^{7c}$ | —* | —* | $A^c$ | $Z^c$ | 0-3 |
| E-7 | $R^{1b}$ | $R^{2c}$ | $R^{3c}$ | $R^{4c}$ | $R^{5c}$ | $R^{6b}$ | $R^{7c}$ | —* | —* | $A^c$ | $Z^c$ | 0-3 |
| E-8 | $R^{1c}$ | $R^{2c}$ | $R^{3c}$ | $R^{4c}$ | $R^{5c}$ | $R^{6b}$ | $R^{7c}$ | —* | —* | $A^c$ | $Z^c$ | 0-3 |
| E-9 | $R^{1c}$ | $R^{2c}$ | $R^{3d}$ | $R^{4c}$ | $R^{5c}$ | $R^{6b}$ | $R^{7c}$ | —* | —* | $A^c$ | $Z^c$ | 0-3 |
| E-10 | $R^{1c}$ | $R^{2c}$ | $R^{3d}$ | $R^{4c}$ | $R^{5c}$ | $R^{6b}$ | $R^{7c}$ | —* | —* | $A^c$ | $Z^d$ | 0-3 |
| E-11 | $R^{1c}$ | $R^{2c}$ | $R^{3d}$ | $R^{4c}$ | $R^{5c}$ | $R^{6b}$ | $R^{7c}$ | —* | —* | $A^d$ | $Z^d$ | 0-3 |
| E-12 | $R^{1d}$ | $R^{2c}$ | $R^{3d}$ | $R^{4c}$ | $R^{5c}$ | $R^{6b}$ | $R^{7c}$ | —* | —* | $A^d$ | $Z^d$ | 0-3 |
| E-13 | $R^{1d}$ | $R^{2c}$ | $R^{3d}$ | $R^{4c}$ | $R^{5d}$ | $R^{6b}$ | $R^{7c}$ | —* | —* | $A^d$ | $Z^d$ | 0-3 |
| E-14 | $R^{1d}$ | $R^{2c}$ | $R^{3d}$ | $R^{4c}$ | $R^{5d}$ | $R^{6b}$ | $R^{7d}$ | —* | —* | $A^d$ | $Z^d$ | 0-3 |
| E-15 | $R^{1d}$ | $R^{2c}$ | $R^{3d}$ | $R^{4c}$ | $R^{5d}$ | $R^{6b}$ | $R^{7d}$ | —* | —* | $A^d$ | $Z^d$ | 0-2 |
| E-16 | $R^{1d}$ | $R^{2c}$ | $R^{3d}$ | $R^{4d}$ | $R^{5d}$ | —* | $R^{7d}$ | —* | —* | $A^d$ | $Z^d$ | 0-2 |
| E-17 | $R^{1d}$ | $R^{2c}$ | $R^{3d}$ | $R^{4d}$ | $R^{5d}$ | —* | $R^{7d}$ | —* | —* | $A^d$ | $Z^d$ | 3 |
| E-18 | $R^{1d}$ | $R^{2c}$ | $R^{3d}$ | $R^{4d}$ | $R^{5d}$ | —* | $R^{7d}$ | —* | —* | $A^d$ | $Z^d$ | 2 |
| E-19 | $R^{1d}$ | $R^{2c}$ | $R^{3d}$ | —* | $R^{5d}$ | —* | $R^{7d}$ | —* | —* | $A^d$ | $Z^d$ | 0 |
| E-20 | $R^{1d}$ | $R^{2c}$ | $R^{3d}$ | $R^{4d}$ | $R^{5d}$ | —* | $R^{7d}$ | —* | —* | $A^d$ | $Z^d$ | 1 |

—* means that the respective variable does not exist in the corresponding embodiment the tautomers thereof, the stereoisomers thereof, the mixtures thereof, and the salts thereof.

Accordingly, for example E-20 covers compounds of formula I,
wherein
$R^1$ is selected from the group $R^{1d}$ consisting of
    $H_3C$—, $H_3C$—$CH_2$— and cyclopropyl-,
$R^2$ is selected from the group $R^{2c}$ consisting of
    H,
$R^3$ is selected from the group $R^{3d}$ consisting of H,
$R^4$ is selected independently of each other from the group $R^{4d}$ consisting of
    H, F, Cl, Br, $C_{1-4}$-alkyl-, cyclopropyl-, $F_2HC$—, $F_3C$—, $H_3CO$—, $F_2HCO$— and $F_3CO$—, and
    wherein two of the aforementioned groups $R^{4d}$ provided that they are attached to adjacent carbon atoms of the phenyl ring in formula I may form together with these carbon atoms a benzo ring,
A is selected from the group $A^d$ consisting of
    —$(CH_2)_5$—
    wherein the above mentioned group may optionally be substituted with one or two $R^5$,
$R^5$ is selected from the group $R^{5d}$ consisting of
    HO—, O═, $H_3C$—, $H_2N$—C(O)— and HO—$CH_2$—,
$R^7$ is selected from the group $R^{7d}$ consisting of
    H and F,
Z is selected from the group $Z^d$ consisting of
    —O—,
and m=1,
the tautomers thereof, the stereoisomers thereof, the mixtures thereof, and the salts thereof.

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

An asterisk may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

The term halogen generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer from 2 to n, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. The term $C_{2-5}$-alkenyl includes for example the radicals $H_2C$=$CH$—, $H_2C$=$CH$—$CH_2$—, $H_3C$—$CH$=$CH$—, $H_2C$=$CH$—$CH_2$—$CH_2$—, $H_3C$—$CH$=$CH$—$CH_2$—, $H_3C$—$CH_2$—$CH$=$CH$—, $(H_3C)_2C$=$CH$—, $H_2C$=$CH$—$CH_2$—$CH_2$—$CH_2$—, $H_3C$—$CH$=$CH$—$CH_2$—$CH_2$—, $H_3C$—$CH_2$—$CH$=$CH$—$CH_2$—, $H_3C$—$CH_2$—$CH_2$—$CH$=$CH$—, $H_2C$=$CH$—$CH$=$CH$—$CH_2$— and $(H_3C)_2C$=$CH$—$CH_2$—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. The term $C_{2-5}$-alkinyl includes for example the radicals $HC$≡$C$—, $HC$≡$C$—$CH_2$—, $H_3C$—$C$≡$C$—, $HC$≡$C$—$CH_2$—$CH_2$—, $H_3C$—$C$≡$C$—$CH_2$—, $H_3C$—$CH_2$—$C$≡$C$—, $HC$≡$C$—$CH_2$—$CH_2$—$CH_2$—, $H_3C$—$C$≡$C$—$CH_2$—$CH_2$—, $H_3C$—$CH_2$—$C$≡$C$—$CH_2$—, $H_3C$—$CH_2$—$CH_2$—$C$≡$C$— and $(H_3C)_2CH$—$C$≡$C$—.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The compounds according to the invention may be obtained using methods of synthesis known in principle. Preferably, the compounds are obtained by the following methods according to the invention which are described in more detail hereinafter.

A general route to access the spirocyclic structure of the compounds of the invention is given in Scheme 1; $R^1$, $R^2$, $R^3$, $R^4$, $R^6$, $R^7$, A, Z, and m have the meanings as defined hereinbefore and hereinafter. Starting from the cyclic ketone or imine 1 compound 2 is prepared via addition of an allyl metal species to the carbon-heteroatom double bond; the metal species complementing the allyl group is e.g. Li, MgHal (Hal is Cl, Br, I), $CrCl_2$, ZnHal (Hal is Cl, Br, I), MnHal (Hal is Cl, Br, I), $InHal_2$ (Hal is Cl, Br, I), $SmI_2$, $CeCl_2$, $SiMe_3$, $SnBu_3$, SnCl, or $SnCl_3$. The allyl metal species may be prepared in a separate step before combining it with substrate 1 or in situ from the respective allyl halide and an elemental form of the metal or a reducing form of the metal halide, e.g. $SmI_2$ or $CrCl_2$. Depending on the reactivity of the allyl metal species, additives such as Lewis acid or base, e.g. $TiCl_4$ or n-$Bu_4NF$ for allyl-$SiMe_3$, to promote addition to the C=O/C=N group may be beneficial or even necessary. Most of the allyl metal species are best used in inert solvents, such as tetrahydrofuran, 1,2-dimethoxyethane, 1,4-dioxane, ether, toluene, benzene, hexanes, or mixtures thereof, though, for the less reactive ones solvents, such as N-methylpyrrolidinone, N,N-dimethylacetamide, N,N-dimethylformamide, acetonitrile, dichloromethane, or mixtures thereof or with the solvents listed before, may also be employed; protic solvents, such as water or alcohol, can be used as solvent or co-solvent for the reaction using allyl halide with elemental forms of zinc or indium in the presence of substrate 1. Alternatively, allyl addition can be accomplished with allyl alcohol combined with $SnCl_2$ and a palladium catalyst, e.g. $PdCl_2$(benzonitrile)$_2$. Allyl addition is preferably conducted with allylmagnesium halide in ether or tetrahydrofuran at −50 to 40° C. or by using allyl halide, zinc, and ammonium chloride in a mixture of water and tetrahydrofuran at 0 to 60° C. Compound 4 can be obtained either directly from compound 2 by ozonolysis or via compound 3 by oxidative cleavage of the glycol moiety. The former proceeding is preferably carried out with ozone in an inert solvent, e.g. dichloromethane, at low temperature, −80 to 0° C., to give the ozonide that is treated with a reducing agent, e.g. dimethyl sulfide or triphenylphosphine, to afford aldehyde 4. The latter process comprises two reaction steps that can be conducted separately or in one pot. Dihydroxylation of compound 2 to obtain compound 3 is preferably performed with catalytic amounts of $OsO_4$ or $K_2OsO_4$ and a co-oxidant, e.g. N-methyl-morpholine-N-oxide, hydrogen peroxide, or $K_3Fe(CN)_6$. Diol 3 is then cleaved using $NaIO_4$ in an aqueous solution or $Pb(O_2CCH_3)_4$ in an inert solvent at −10 to 60° C. Using $RuCl_3$, $OsO_4$, or $K_2OsO_4$ combined with an oxidizing agent, e.g. $NaIO_4$, allows to conduct both steps in one pot to give aldehyde 4 without isolating diol 3. Compound 5 is obtained from aldehyde 4 and an appropriate amine via reductive amination with e.g. $NaHB(O_2CCH_3)_3$, $NaH_3BCN$, or $NaBH_4$, optionally in the presence of an acid such as acetic acid (methods for the reductive amination of aldehydes are described in Baxter, E. W. and Reitz, A. B. "Organic Reactions" Volume 59, Ed. Overman, L. E., Wiley Interscience, 2002). Treatment of amine 5 with activated carbonic acid derivative 6, e.g. phosgene, diphosgene, triphosgene, carbonyl diimidazole, p-nitrophenyl chloroformate, $ClCO_2C_{1-4}$-alkyl, $ClCO_2CH_2Ph$, or $(C_{1-4}$-alkyl$OCO_2)_2CO$, in an inert solvent, such as tetrahydrofuran, 1,4-dioxane, $CH_2Cl_2$, toluene, or acetonitrile, preferably in the presence of a base, such as triethylamine, pyridine, or $NaHCO_3$, optionally in the presence of an additive such as 4-dimethylaminopyridine, at −10 to 120° C. provides target compound I'. Depending on the carbonic acid derivative 6 used, cyclization of the intermediate from amine 5 to compound I' may need more forcing conditions, e.g. NaH, KH, sodium amide, or butyl lithium in an inert solvent, e.g. toluene, ether, tetrahydrofuran, 1,4-dioxane, N,N-dimethylformamide, or N-methylpyrrolidinone, at −80 to 100° C.

Scheme 1. Strategy 1 to build the spirocyclic skeleton

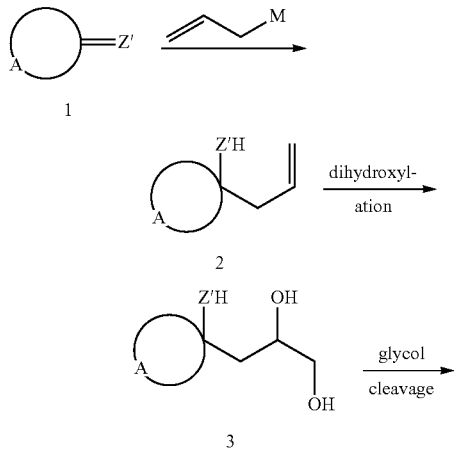

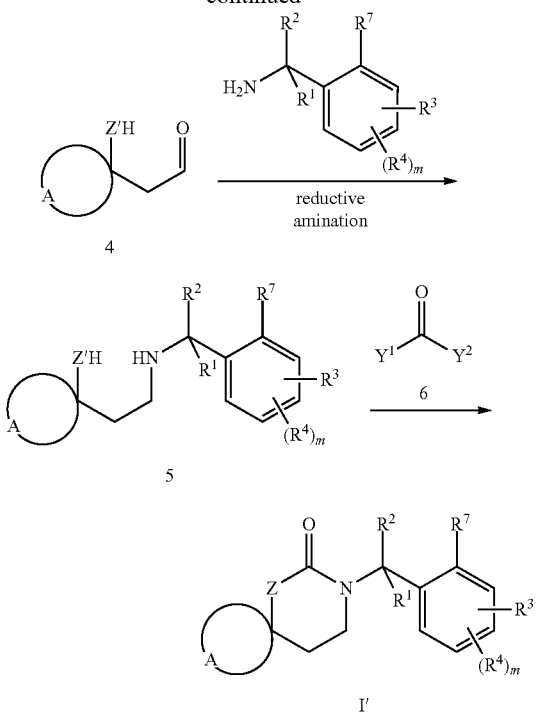

$Z' = O, NR^6$, NPG (PG = protecting group)
M = e.g. Li, MgHal, ZnHal, InHal$_2$ (Hal = Cl, Br, I)
$Y^1, Y^2 = Cl$, —$OCCl_3$, imidazol-1-yl, 4-$O_2N$—$C_6H_4$—O—

Another viable synthetic route to the spirocyclic scaffold is delineated in Scheme 2; $R^1$, $R^2$, $R^3$, $R^4$, $R^6$, $R^7$, Z, and m have the meanings as defined hereinbefore and hereinafter. Starting with compound 7 compound 9 is accessed through consecutive addition of two alkenylmetal compounds to the carboxy carbon in 7. Preferred alkenylmetal compounds are derived from Li, MgHal (Hal=Cl, Br, I), and $CeCl_2$, which are employed in inert solvent, e.g. tetrahydrofuran, 1,4-dioxane, 1,2-dimethoxyethane, ether, toluene, benzene, hexanes, or mixtures thereof, at −80 to 60° C. Depending on the reactivity of the carboxy carbon atom and the nature of the alkenylmetal compounds, the addition of alkenylmetals 8a and 8b are best conducted in one pot without isolating the intermediate, a ketone or an imine, or in two separate reaction steps. The replacement of the leaving group in compound 9 with amine 10 to provide compound 11 is preferably conducted in the presence of a base, e.g. triethylamine, diisopropyl-ethylamine, pyridine, $K_2CO_3$, KO$^t$Bu, or NaH, in a solvent, e.g. water, alcohol, dimethyl sulfoxide, N-methylpyrrolidinone, N,N-dimethylformamide, acetonitrile, tetrahydrofuran, 1,4-dioxane, toluene, or mixtures thereof, at −10 to 140° C. Compound 11 may also be obtained by reversing step 1 (7→9) and 2 (9→11) of Scheme 2. Ring-closing metathesis with the two olefinic moieties of amine 11 and a catalyst, preferably derived from Ru, e.g. Grubbs catalyst, Grubbs $2^{nd}$ generation catalyst, Hoveyda-Grubbs catalyst, or Hoveyda-Grubbs $2^{nd}$ generation catalyst, in dichloromethane, 1,2-dichloroethane, toluene, or benzene, at −20 to 120° C. affords olefin 12 (for ring-closing metathesis see e.g. Curr. Org. Chem. 2006, 10, 185-202 and references quoted therein). The concluding step of the strategy delineated in Scheme 2 equals the one in Scheme 1 and can be carried out analogously.

Scheme 2. Strategy 2 to build the spirocyclic skeleton

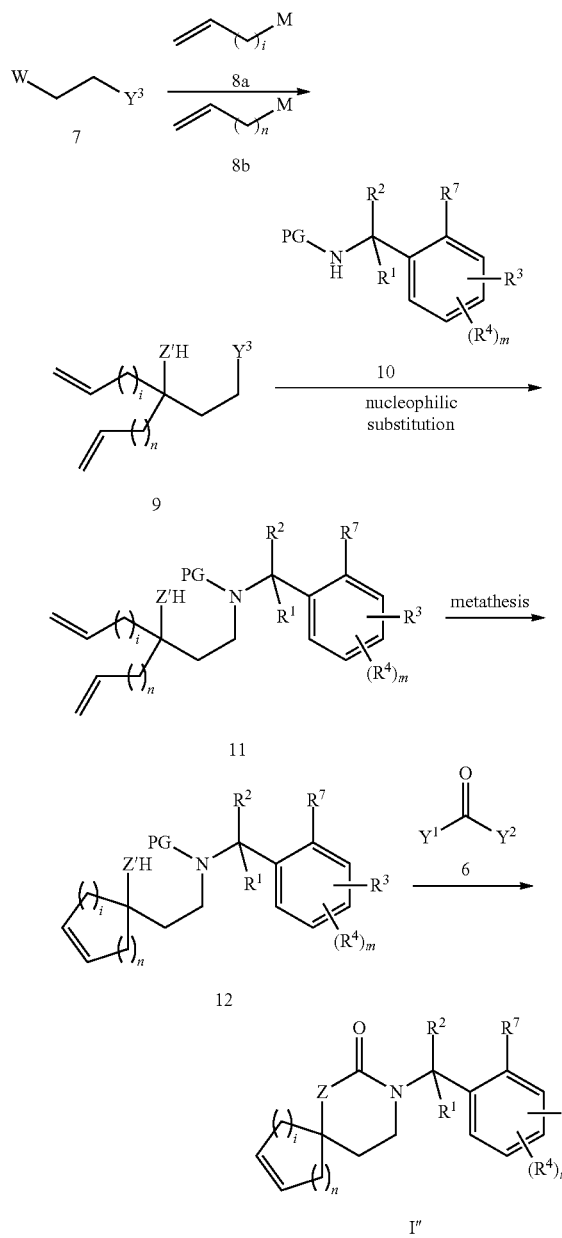

i, n = 0, 1, 2, 3, 4, 5
M = e.g. Li, MgCl, MgBr, MgI, CeCl$_2$
PG = protective group or H
Z' = O, NR$^6$, NPG' (PG' = protective group)
Y$^3$ = leaving group, e.g. Cl, Br, I, OSO$_2$Me, OSO$_2$Ph
W = e.g. CN, CO$_2$C$_{1-4}$-alkyl, COCl
Y$^1$, Y$^2$ = Cl, —OCCl$_3$, imidazol-1-yl, 4-O$_2$N—C$_6$H$_4$—O—

Scheme 3 outlines a general synthetic route to spirocyclic lactams of the present invention; A, R$^1$, R$^2$, R$^3$, R$^4$, R$^7$, and m have the meanings as defined hereinbefore and hereinafter. The sequence starts with the preparation of compound 14 from cyclic ketone 13. This reaction may be accomplished by addition of a malonic acid derivative, e.g. malodinitrile, malonic acid diester, malonic acid monoester, or a cyanoacetate, to the carbonyl group in 13 followed by elimination of water from the resulting intermediate (Knoevenagel condensation). The reaction is preferably carried out with ammonium acetate, piperidinium acetate, piperidine, triethylamine, diethylamine, or sodium ethylate, some of them optionally combined with acetic acid, in benzene, toluene, N,N-dimethylformamide, dimethyl sulfoxide, ethanol, or methanol, at 0 to 140° C. Alternatively, the transformation 13→14 may be achieved by a Wittig olefination or related reaction. Particularly suited reagents for this proceeding are cyanomethylphosphonic acid esters and alkoxycarbonylmethyl-phosphonic acid esters that are used in combination with a base, e.g. NaH, NaNH$_2$) or $^n$BuLi, in an inert solvent, e.g. hexanes, toluene, tetrahydrofuran, 1,2-dimethoxyethane, N-methylpyrrolidinone, N,N-dimethylformamide, or mixtures thereof, at −30 to 120° C. Addition of allyl to olefin 14 may be done using an allylmetal species, e.g. allyllithium, allylmagnesium halide, or allylzinc halide, optionally combined with a copper(I) salt, such as CuI, CuCN, or CuCN*2LiCl, in an inert solvent, such as tetrahydrofuran or ether, at −80 to 60° C. The synthetic effort to convert compound 15 to ester 16 depends on the groups EWG and EWG'. In case both groups are carboxy, carboxylic ester, and/or nitrile groups, they are hydrolyzed (for hydrolysis of nitrile and ester groups see the section hereinafter) to give the diacid derivative of 15 (EWG, EWG'=COOH) which cleaves off one carboxy group upon heating, optionally in the presence of acid. The resulting monoacid of compound 16 (R=H) can be converted to ester 16 as described hereinafter. Conversion of ester 16 to aldehyde 17 is related to the transformation described for compound 2 in Scheme 1 and may be realized analogously. The first step of the following transformation in Scheme 3, reductive amination of aldehyde 17, provides an aminoester that may cyclize spontaneously under the amination conditions or through the action of an added base or acid to give the spirocyclic compound I'''. The reductive amination may be carried out as described in Scheme 1.

Scheme 3. Strategy to build the spirocyclic lactam skeleton

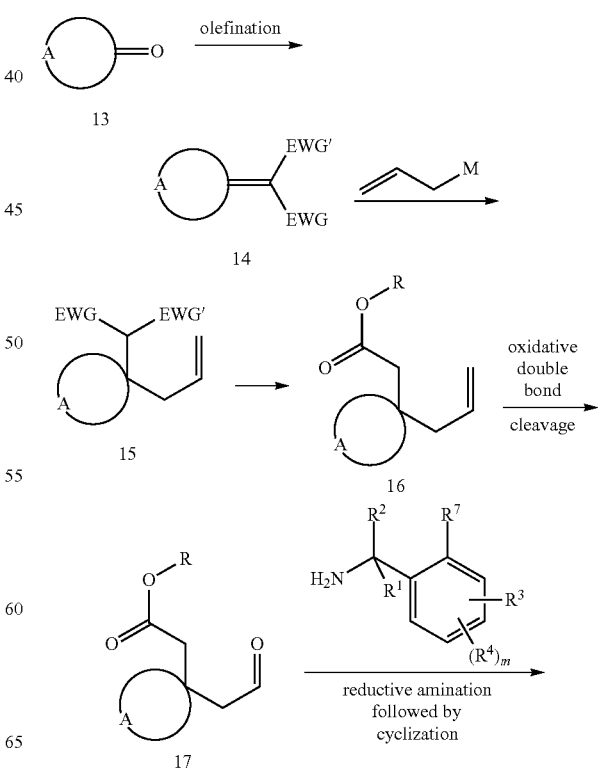

-continued

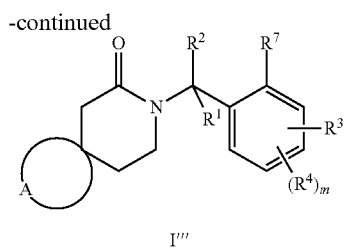

EWG = CN, C(═O)LG   EWG' = H, CN, C(═O)LG
LG = leaving group, e.g. Cl, OC$_{1-4}$-alkyl, OBn, OPh, imidazol-1-yl
R = C$_{1-4}$-alkyl, optionally substituted Bn
M = metal, e.g. Li, MgHal, Zn Hal, CeCl$_2$, ZnHal, complexes with Cu(I)
Hal = Cl, Br, I The synthetic routes presented may rely on the use of protecting groups. Suitable protecting groups for the respective functionalities and their removal are described hereinafter and may analogously be employed (see also: *Protecting Groups*, Philip J. Kocienski, 3$^{rd}$ edition, Georg Thieme Verlag, Stuttgart, 2004 and references quoted therein).

In the following a few feasible derivatizations of compounds of general formula I or precursors thereof, obtained as described above or another route described or indicated in the public literature, that bear certain functional groups to assemble other compounds of general formula I or precursors thereof are vicariously summarized. This compilation is by no means meant to be complete but is only supposed to give some possibilities by way of example.

If in the process of manufacture according to the invention a compound of general formula I or a precursor thereof is obtained which contains an amino, alkylamino, or imino group, this may be converted by acylation or sulfonylation into a corresponding acyl or sulfonyl compound of general formula I or a precursor thereof.

If a compound of general formula I or a precursor thereof is obtained which contains a hydroxy group, this may be converted by acylation or sulfonylation into a corresponding acyl or sulfonyl compound of general formula I or a precursor thereof.

If a compound of general formula I or a precursor thereof is obtained which contains a hydroxy group, this may be converted by alkylation into a corresponding ether of general formula I or a precursor thereof.

If a compound of general formula I or a precursor thereof is obtained which contains an amino, alkylamino, or imino group, this may be converted by alkylation or reductive alkylation into a corresponding alkyl compound of general formula I or a precursor thereof.

If a compound of general formula I or a precursor thereof is obtained which contains a nitro group, this may be converted by reduction into a corresponding amino compound.

If a compound of general formula I or a precursor thereof is obtained which contains an imino group, this may be converted by nitrosation and subsequent reduction into a corresponding N-amino-imino compound.

If a compound of general formula I or a precursor thereof is obtained which contains a C$_{1-4}$-alkyloxycarbonyl group, this may be converted by cleavage of the ester into the corresponding carboxy compound.

If a compound of general formula I or a precursor thereof is obtained which contains a carboxy group, this may be converted into a corresponding ester of general formula I or a precursor thereof.

If a compound of general formula I or a precursor thereof is obtained which contains a carboxy or ester group, this may be converted by reaction with an amine into a corresponding amide of general formula I or a precursor thereof.

If a compound of general formula I or a precursor thereof is obtained which contains an aromatic substructure, this may be derivatized with a chlorine, bromine, or iodine atom or a nitro, sulfonic acid, chlorosulfonyl, or acyl group by an electrophilic substitution reaction to a corresponding compound of general formula I or a precursor thereof.

If a compound of general formula I or a precursor thereof is obtained which contains an aromatic substructure derivatized with an amino group, this may be transformed into a corresponding cyano, fluoro, chloro, bromo, iodo, hydroxy, mercapto, or azido derivatized compound of general formula I or a precursor thereof by diazotization and subsequent replacement of the diazo group with cyanide, fluoride, chloride, bromide, iodide, hydroxide, alkyl or hydrogen sulfide, or azide, respectively.

If a compound of general formula I or a precursor thereof is obtained which contains an aromatic substructure bearing an amino group, this may be converted into a corresponding aryl derivatized aromatic compound of general formula I or a precursor thereof by diazotization of the amino group and subsequent replacement of the diazo group with an appropriate aryl nucleophile mediated by a suited transition metal species.

If a compound of general formula I or a precursor thereof is obtained which contains an aromatic substructure bearing a chlorine, bromine, or iodine atom, or a mesyloxy, tosyloxy, or trifluoromethylsulfonyloxy group, this may be converted into a corresponding aryl, alkenyl, alkynyl, or alkyl derivatized aromatic compound of general formula I or a precursor thereof by replacement of the respective group by aryl, alkenyl, alkynyl, or alkyl using a transition metal species mediated process.

If a compound of general formula I or a precursor thereof is obtained which contains an aromatic substructure bearing a chlorine, bromine, or iodine atom, or a mesyloxy, tosyloxy, or trifluoromethylsulfonyloxy group, this may be replaced with hydrogen to give a corresponding aromatic compound of general formula I or a precursor thereof.

If a compound of general formula I or a precursor thereof is obtained which contains two heteroatoms at adjacent carbon atoms that are amino and hydroxy, amino, or mercapto, these heteroatoms may be linked via a carboxy carbon atom to form a cyclic amidine, imino ester, or imino thioester substructure that may be part of an aromatic ring.

If a compound of general formula I or a precursor thereof is obtained which contains a cyano group, this may be converted by reduction into a corresponding aminoalkyl derivatized compound of general formula I or a precursor thereof.

If a compound of general formula I or a precursor thereof is obtained which contains a cyano group, this may be converted into a corresponding N-hydroxycarbamimidoyl group by treatment with hydroxylamine.

If a compound of general formula I is obtained which contains an N-hydroxycarbamimidoyl group, this may be converted to an oxadiazole derivatized compound of general formula I or a precursor thereof by treatment with a carboxylic or related group.

If a compound of general formula I or a precursor thereof is obtained which contains an aminocarbonyl group, this may be converted by dehydration into a corresponding cyano compound of general formula I or a precursor thereof.

If a compound of general formula I or a precursor thereof is obtained which contains a keto or aldehydic group, this may be converted by reduction into a corresponding hydroxy compound of general formula I or a precursor thereof.

If a compound of general formula I or a precursor thereof is obtained which contains a carboxylic acid or aminocarbonyl group, this may be converted by a rearrangement reaction into a corresponding amino derivatized compound of general formula I or a precursor thereof.

If a compound of general formula I or a precursor thereof is obtained which contains a keto or aldehyde group, this may be converted into an alkenyl derivatized compound of general formula I or a precursor thereof.

If a compound of general formula I or a precursor thereof is obtained which contains an olefinic C═C double or a C≡C triple bond, this may be reduced to give the corresponding saturated compound of general formula I or a precursor thereof.

If a compound of general formula I or a precursor thereof is obtained which contains a keto or aldehydic group, this may be converted into a corresponding tertiary or secondary hydroxy compound of general formula I or a precursor thereof.

If a compound of general formula I or a precursor thereof is obtained which contains a carboxylic ester group, this may be converted into a tertiary alcohol by the addition of two equivalents of an organo metal compound.

If a compound of general formula I or a precursor thereof is obtained which contains a primary or secondary hydroxy group, this may be converted by oxidation into a corresponding carbonyl compound of general formula I or a precursor thereof.

If a compound of general formula I or a precursor thereof is obtained which contains an olefinic bond, this may be converted into a corresponding hydroxy compound of general formula I or a precursor thereof by hydroboration followed by oxidation.

If a compound of general formula I or a precursor thereof is obtained which contains an olefinic bond, this may be converted by dihydroxylation into a corresponding 1,2-dihydroxy compound of general formula I or a precursor thereof.

If a compound of general formula I or a precursor thereof is obtained which contains an olefinic bond, this may be converted by ozonolysis into a corresponding carbonyl compound of general formula I or a precursor thereof.

If a compound of general formula I or a precursor thereof is obtained which contains an olefinic bond, this may be converted into a corresponding hydroxy compound of general formula I or a precursor thereof by epoxidation followed by oxirane opening with a hydride source.

If a compound of general formula I or a precursor thereof is obtained which contains an olefinic bond, this may be converted by Wacker oxidation into a corresponding carbonyl compound of general formula I or a precursor thereof.

If a compound of general formula I or a precursor thereof is obtained which contains an olefinic bond, this may be converted by hydrocyanation into a corresponding cyano compound of general formula I or a precursor thereof.

If a compound of general formula I or a precursor thereof is obtained which contains a cyano group, this may be converted by water addition into a corresponding aminocarbonyl or carboxy compound of general formula I or a precursor thereof.

The subsequent esterification is optionally carried out in a solvent, such as methylene chloride, N,N-dimethylformamide, benzene, toluene, chlorobenzene, tetrahydrofuran, 1,4-dioxane, or mixtures thereof or particularly advantageously in the corresponding alcohol, optionally in the presence of an acid, e.g. hydrochloric acid, or a dehydrating agent, e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-carbonyldiimidazole, N,N'-dicyclohexylcarbodiimide, triphenylphosphine combined with carbon tetrachloride, or combinations thereof, optionally in the presence of 4-dimethylaminopyridine and/or 1-hydroxybenzotriazole. The reactions are conducted between 0 and 150° C., preferably between 0 and 80° C.

The ester formation may also be carried out by reacting a compound which contains a carboxy group with a corresponding alkyl halide in the presence of a base.

The subsequent acylation or sulfonylation is optionally carried out in a solvent, such as methylene chloride, N,N-dimethylformamide, benzene, toluene, chlorobenzene, tetrahydrofuran, 1,4-dioxane, or mixtures thereof with a corresponding acyl or sulfonyl electrophile, optionally in the presence of a tertiary organic base, an inorganic base, or a dehydrating agent. Routinely used agents are e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-carbonyldiimidazole, triphenylphosphine combined with carbon tetrachloride, or combinations thereof that may be employed in the presence of 4-dimethylaminopyridine and/or 1-hydroxybenzotriazole at temperatures between 0 and 150° C., preferably between 0 and 80° C.

The subsequent alkylation is optionally carried out in methylene chloride, N,N-dimethylformamide, benzene, toluene, chlorobenzene, tetrahydrofuran, 1,4-dioxane, or mixtures thereof with an alkylating agent such as a corresponding halide or sulfonic acid ester, e.g. methyl iodide, ethyl bromide, dimethyl sulfate, or benzyl chloride, optionally in the presence of a tertiary organic base or an inorganic base at temperatures between 0 and 150° C., preferably between 0 and 100° C.

The subsequent reductive alkylation is carried out with a corresponding carbonyl compound, such as formaldehyde, acetaldehyde, propionaldehyde, acetone, or butyraldehyde, in the presence of a complex metal hydride, such as sodium borohydride, lithium borohydride, sodium triacetoxyborohydride, or sodium cyanoborohydride, conveniently at a pH value of 6-7 and ambient temperature, or using hydrogen in the presence of a transition metal catalyst, e.g. palladium on charcoal, at hydrogen pressures of 1 to 5 bar. Methylation may also be carried out in the presence of formic acid as reducing agent at elevated temperature, e.g. between 60 and 120° C.

The subsequent reduction of a nitro group is carried out, for example, with hydrogen and a catalyst such as palladium on carbon, platinum dioxide, or Raney nickel, or using other reducing agents such as tin(II) chloride, iron, or zinc optionally in the presence of an acid such as acetic acid.

The subsequent nitrosation of an imino group followed by reduction to obtain an N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-4}$-alkyloxycarbonyl group to obtain the carboxy group is carried out, for example, by hydrolysis with an acid such as hydrochloric acid or sulfuric acid or an alkali metal hydroxide such as lithium hydroxide, sodium hydroxide, or potassium hydroxide. The tert-butyl group is preferably removed by treatment with a strong acid, e.g. trifluoroacetic acid or hydrochloric acid, in an inert solvent such as dichloromethane, 1,4-dioxane, or ethyl acetate.

The subsequent amide formation is carried out by reacting a corresponding reactive carboxylic acid derivative with a corresponding amine in a solvent, such as methylene chloride, N,N-dimethylformamide, benzene, toluene, chlorobenzene, tetrahydrofuran, 1,4-dioxane, or mixtures thereof, or without an solvent in an excess of the amine, optionally in the presence of a tertiary organic base, an inorganic base, 4-dimethylaminopyridine, and/or 1-hydroxy-benzotriazole, at temperatures between 0 and 150° C., preferably between 0 and 80° C. Using the carboxylic acid may lead to the desired amide by in situ activation of the carboxy function with e.g. isobutyl chloroformate, thionyl chloride, oxalyl chloride, trimethylchlorosilane, phosphorus trichloride, phosphorus pentoxide, N,N'-carbonyldiimidazole, triphenylphosphine combined with carbon tetrachloride, 2-(1H-benzotriazol-1-yl)-1,1,3,3-tetramethyluronium tetrafluoroborate, N,N'-dicyclohexylcarbodiimide, or combinations thereof.

The subsequent introduction of a chlorine, bromine, or iodine atom into an aromatic substructure may be carried out by reacting the aromatic compound with an appropriate electrophile of the respective halogen atom. Suited chlorine and bromine electrophiles may be e.g. N-halosuccinimide, HOCl, HOBr, tert-BuOCl, tert-BuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, boron trifluoride hydrate, boron trifluoride etherate, or aluminum halide. Further useful combinations may be LiBr and ceric ammonium nitrate, KCl or KBr with Oxone®, or KBr and sodium perborate. Suited iodine electrophiles may be generated from iodine and an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles are optionally used without an additive or in the presence of an acid such as acetic acid, trifluoroacetic acid, or sulfuric acid or a Lewis acid such as boron trifluoride hydrate or copper salts. If a nitro group is to be introduced appropriate nitro electrophile sources may be, for instance, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $S(=O)_3$, $ClS(=O)_2OH$, or $ClS(=O)_2NMe_2$ combined with indium triflate. Reacting the aromatic compound with $ClS(=O)_2OH$ gives the corresponding chlorosulfonylated derivative that may be hydrolyzed to the sulfonic acid. Acylating the aromatic part is conducted using an acyl electrophile that may be generated from the respective acyl halide, e.g. chloride, or acyl anhydride and a Lewis acid such as aluminum halide, diethylaluminum halide, indium halide, iron(III) halide, tin(IV) halide, boron trifluoride, titanium(IV) halide, or a Brønsted acid, e.g. sulfuric acid or triflic acid. The formyl group is preferably introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, 1,2-dichloroethane, chlorobenzene, dichlorobenzene, ether, 1,4-dioxane, fluorinated hydrocarbons, hexanes, quinoline, and acetonitrile. Temperatures preferably applied range from 0 to 180° C.

The subsequent replacement of an amino group attached to an aromatic substructure is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkylnitrite, e.g. tert-butyl nitrite or iso-amyl nitrite. The diazotization is optionally carried out in methylene chloride, 1,2-dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane, or mixtures thereof at temperatures between −10 and 100° C. (diazotization of amino groups is detailed in, for example, Angew. Chem. Int. Ed. 1976, 15, 251). The subsequent displacement of the diazo group with a cyano group, chlorine, or bromine atom using copper cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10 and 120° C. in one of the solvents or mixtures mentioned above. The replacement of the diazo group with a fluorine atom may be achieved with a tetrafluoroborate salt or tetrafluoroboric acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced with hydroxy using water or an aqueous solvent mixture at temperatures between 0 and 180° C. The reaction usually works without further additives but the addition of copper oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. Synth. Commun. 2001, 31, 1857 and references quoted therein).

The subsequent replacement of an amino group which is attached to an aromatic substructure by an aryl group may be accomplished via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imdiazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. The diazo compound is preferably employed as its tetrafluoroborate salt optionally in water, N-methylpyrrolidinone, N,N-dimethylformamide, methylene chloride, benzene, toluene, tetrahydrofuran, ethyl acetate, alcohol, ether, 1,2-dimethoxyethane, 1,4-dioxane, or mixtures thereof at temperatures between 10 and 180° C., preferably between 20 and 140° C.

The subsequent replacement of a chlorine, bromine, or iodine atom or a mesyloxy, tosyloxy, or trifluoromethylsulfonyloxy group which are attached to an aromatic substructure with an aryl, alkenyl, alkynyl, or alkyl residue is preferably mediated by a transition metal species derived from palladium, nickel, copper, or iron. The active catalyst may be a complex of the transition metal with ligands such as phosphines, e.g. tri-tert-butylphosphine, tricyclohexylphosphine, 2-(substituted phenyl)phenyl-dicyclohexylphosphines, 2-(substituted phenyl)phenyl-di-tert-butylphosphines, 1,1'-bis(diphenylphosphino)ferrocene, triphenylphosphine, tri-tolylphosphine, or trifuryl-phosphine, phosphites, 1,3-disubstituted imdiazole carbenes, 1,3-disubstituted imidazolidine carbenes, dibenzylideneacetone, allyl, or nitriles, an elemental form of the transition metal such as palladium on carbon or nanoparticles of iron or palladium, or a salt such as fluoride, chloride, bromide, acetate, triflate, or trifluoroacetate. The replacement reaction is preferably conducted with a trifluoroborate, boronic acid, or boronic ester (Suzuki or Suzuki-type reaction), zinc halide (Negishi or Negishi-type reaction), stannane (Stille or Stille-type reaction), silane (Hiyama or Hiyama-type reaction), magnesium halide (Kumada or Kumada-type reaction) of the aryl, alkenyl, or alkyl residue to be introduced. The terminal alkyne is preferably used as such or as its zinc acetylide derivative. Depending on the nature of the electrophilic and nucleophilic reaction partners, additives such as halide salts, e.g. lithium chloride, potassium fluoride, tetrabutylammonium fluoride, hydroxide sources such as potassium hydroxide or potassium carbonate, silver salts such as silver oxide or triflate, and/or copper salts such as copper chloride or copper thiophene-2-carboxylate may be advantageous or even essential. Copper iodide is a preferred additive in the coupling with terminal alkynes (Sonogashira reaction). The coupling reactions are preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, though, depending on the nucleophile some of them are less or not suited at all. Preferred temperatures are in the range from −10 to 180° C.

The subsequent replacement of a chlorine, bromine, or iodine atom or a mesyloxy, tosyloxy, or trifluoromethylsulfonyloxy group which are attached to an aromatic substructure with a hydrogen atom is preferably mediated by a transition metal species derived from palladium, nickel, platinum, or rhodium. The active catalyst may be a complex of the transition metal with ligands, an elemental form, or a salt of the transition metal as mentioned above. Raney nickel and palladium on carbon are among the preferred catalyst species. Suited hydrogen sources may be hydrogen, preferably at pressures of 1 to 10 bar, silanes, e.g. trialkoxysilane or polymethylhydrosiloxane, boranes, hydrides, e.g. alkali metal borohydride, formic acid, or formates, e.g. ammonium formate. The reactions are preferably carried out in N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof at −10 to 180° C., more preferably at 20 to 140° C.

The subsequent cyclization starting from a compound bearing two heteroatoms at adjacent carbon atoms is optionally conducted with a carboxy equivalent such as nitrile, carboxylic chloride or fluoride, carboxylic acid, ketene, carboxylic ester, or carboxylic thioester. The overall transformation comprises two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium tert-butoxide. The use of dehydrating reagents such as anhydrides, e.g. acetic anhydride, orthoesters, e.g. trimethyl orthoformate, thionyl chloride, phosgene, diphosgene, triphosgene, phosphorous oxychloride, phosphorous pentachloride, dialkylcarbodiimides, combinations with phosphines, e.g. triphenylphosphine or trialkylphosphine with dialkyl azodicarboxylates, bromine, iodine, or 1,2-dihalo-ethanes, e.g. 1,2-dibromotetrafluoroethane, may be advantageous. The reactions are preferably carried out in inert solvents or mixtures such as methylene chloride, 1,2-dichloroethane, benzene, toluene, tetrahydrofuran, ether, or combinations thereof, though, cyclization in the presence of an acid or a base may also be conducted in water or an alcohol, e.g. methanol, ethanol, iso-propanol, or tert-butanol, or combinations with these solvents. The reactions are carried out at temperatures between 0 and 200° C., preferably between 20 and 140° C.

The subsequent reduction of a cyano group to obtain an aminomethyl group is preferably conducted with hydrogen in the presence of a transition metal species or with a hydride. Suited transition metals may be derived from palladium, nickel, platinum, rhodium, or ruthenium such as palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, N,N-dimethylformamide, or N-methylpyrrolidinone at hydrogen pressures between 1 and 10 bar and at temperatures between 0 and 160° C. Additives such as acids, e.g. hydrochloric acid, methanesulfonic acid, sulfuric acid, or acetic acid, may be beneficial for the reduction with transition metal catalysts. Among the preferred hydride sources are e.g. borohydrides, e.g. sodium borohydride, potassium tri-sec-butylborohydride, borane, or lithium triethylborohydride, and alanates, e.g. lithium aluminum hydride or diisobutylaluminum hydride. Some of these reagents are best used in combination with nickel chloride or cobalt chloride as sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic or aqueous solutions. Preferred reaction temperatures range from −80 to 160° C., more preferred from −40 to 80° C.

The subsequent formation of a N-hydroxycarbamimidoyl group from a cyano group may be carried out by the treatment of the cyano compound with hydroxylamine. The reaction is preferably conducted in aqueous or alcoholic solvents at temperatures between 0 and 140° C.

The subsequent formation of an oxadiazole from an N-hydroxycarbamimidoyl is conducted with a carboxy equivalent such as nitrile, carboxylic chloride or fluoride, carboxylic acid, ketene, carboxylic ester, or carboxylic thioester. The transformation is related to the formation of a ring starting from two heteroatoms at adjacent carbon atoms described above and may be carried out analogously.

The subsequent formation of a cyano group from an aminocarbonyl group is preferably conducted by using a dehydrating reagent such as anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenylphosphite, or triphenyl- or trialkylphosphine combined with tetrachloromethane, 1,2-dibromotetrafluoroethane, or bromine. The reactions are preferably carried out in dichloromethane, 1,2-dichloroethane, hexanes, ether, 1,4-dioxane, benzene, toluene, acetonitrile, mixtures thereof, or without a solvent at temperatures between 0 and 140° C. Additives such as amines, e.g. pyridine or triethylamine, or N,N-dimethylformamide may be beneficial.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydride, L-selectride, or lithium aluminum hydride. The reductions may be conducted in e.g. dichloromethane, 1,2-dichloroethane, hexanes, ether, 1,4-dioxane, tetrahydrofuran, N,N-dimethylformamide, N-methylpyrrolidone, benzene, toluene, alcohols, e.g. methanol, water, or mixtures thereof, though, not all reducing agents are compatible with all of these solvents. Preferred temperatures range from −80 to 140° C. depending on the reducing power of the reagent. Alternatively, hydrogen in the presence of a transition metal catalyst or using the Meerwein-Ponndorf-Verley reduction protocol or a variant thereof may afford the corresponding alcohol.

The subsequent conversion of a carboxy group into an amino group by rearrangement may be accomplished by heating an acyl azide resulting in the formation of an isocyanate (Curtius rearrangement). The isocyanate may be hydrolyzed to produce the free amine or converted into a urea or carbamate derivative by treatment with an amine or an alcohol, respectively. The acyl azide may be obtained by treating an appropriate acyl electrophile, e.g. acyl chloride, carboxylic anhydride, or carboxylic ester, with an azide source, such as e.g. sodium azide or trimethylsilyl azide, in a solvent such as 1,4-dioxane, 1,2-dimethoxyethane, acetonitrile, tetrahydrofuran, dichloromethane, 1,2-dichloroethane, N-methylpyrrolidinone, N,N-dimethylformamide, toluene, benzene, hexanes, or mixtures thereof; water or alcohols may be usable in certain cases as well. The reactions are routinely carried out between −10 and 120° C. Alternatively, the acyl electrophile may be generated in situ from the acid and then converted into the acyl azide: diphenylphosphoryl azide in the presence of a base, e.g. triethylamine or ethyldiisopropylamine, in a solvent such as acetonitrile, benzene, toluene, or an alcohol at elevated temperature has proven to be an effective reagent for this direct conversion. The direct conversion may also be achieved with hydrazoic acid and an acid catalyst such as sulfuric acid in e.g. chloroform at elevated temperatures (Schmidt reaction). Another method to accomplish this overall transformation is the Lossen rearrangement: starting from an acyl electrophile such as acyl chloride the corresponding suited hydroxamic acid derivative is formed that in turn rearranges to give the isocyanate and then the amine by heating and/or treatment with a base, e.g. sodium hydroxide (see e.g. *J. Org. Chem.* 1997, 62, 3858 and *Synthesis* 1990, 1143 and references quoted therein).

An unsubstituted carboxylic amide may be converted into an amine by the so-called Hoffmann rearrangement. Among the suited reagents for this transformation are NaOBr, bromine combined with sodium methoxide, N-bromosuccinimide and sodium methoxide, PhI(O(O=)CCF$_3$)$_2$, and PhI(OH)OTs (Ts is 4-methylphenylsulfonyl).

The subsequent conversion of an aldehydic or a keto functionality into an olefin may be accomplished by, for example, the so-called Wittig reaction and modifications thereof, Peterson olefination, and Julia reaction and modifications thereof. These reactions have large precedence in organic syntheses and are detailed in e.g. March's Advanced Organic Chemistry, Michael B. Smith and Jerry March, John Wiley & Sons Inc., 6. Ed., New Jersey, 2007 and references quoted therein.

The subsequent reduction of a C=C double or C≡C triple bond is preferably conducted with hydrogen in the presence of a transition metal species derived from palladium, nickel, platinum, ruthenium, or rhodium, preferably Raney nickel, palladium on charcoal, platinum oxide, and RhCl(PPh)$_3$. The reactions are preferably carried out in methylene chloride, N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof, at 0 to 180° C., more preferably at 20 to 140° C., and hydrogen pressures of 1 to 10 bar, preferably 1 to 5 bar.

The subsequent transformation of an aldehyde or a ketone to a secondary or tertiary alcohol is preferably accomplished by addition of a carbon nucleophile, e.g. alkyl, allyl, alkenyl, aryl, or alkynyl lithium, magnesium, or cerium compound, in tetrahydrofuran, ether, 1,4-dioxane, 1,2-dimethoxyethane, toluene, hexanes, or mixtures thereof, at −80 to 80° C.

The subsequent transformation of a carboxylic ester into a tertiary hydroxy group is preferably conducted with two or more equivalents of a carbon nucleophile, e.g. alkyl, allyl, alkenyl, aryl, or alkynyl lithium, magnesium, or cerium compound, in tetrahydrofuran, ether, 1,4-dioxane, 1,2-dimethoxyethane, toluene, hexanes, or mixtures thereof, at temperatures of −80 to 80° C.

The subsequent oxidation of a primary or secondary hydroxy compound may be achieved by using an oxidizing agent, such as dimethyl sulfoxide combined with e.g. oxalyl chloride, acetic anhydride, S(=O)$_3$*pyridine, or dicyclohexylcarbodiimide, pyridinium chlorochromate (PCC), pyridinium dichromate (PDC), Dess-Martin periodinane, manganese dioxide, 2,2,6,6-tetramethylpiperidine-N-oxide (TEMPO) optionally combined with a co-oxidant, or tetrapropylammonium perrhutenate (TPAP) combined with a co-oxidant such as N-methyl-morpholine-N-oxide, which are optionally used in the presence of a base, e.g. triethylamine, preferably in toluene, dichloromethane, or 1,2-dichloroethane, at −70 to 60° C. Alternatively, the transformation may be performed as an Oppenauer oxidation with e.g. Al(OtBu)$_3$ and acetone.

The subsequent hydroboration and oxidation of an olefinic bond is conducted with a borane, e.g. borane complexed with tetrahydrofuran, trimethylamine, or dimethyl sulfide, diethylborane, thexylborane, 9-borabicyclo[3.3.1]nonane, NaBH$_4$ combined with BF$_3$ or TiCl$_4$, or dichloroborane, preferably used in tetrahydrofuran at −20 to 60° C. The hydroboration product is subsequently treated with e.g. hydrogen peroxide and sodium hydroxide in an aqueous solution to replace the boron group in the intermediate with hydroxy.

The subsequent dihydroxylation of an olefinic bond is preferably conducted with osmium tetroxide or potassium osmate combined with a co-oxidant, e.g. N-methyl-morpholine-N-oxide or K$_3$Fe(CN)$_6$, preferably in water combined with tBuOH, tetrahydrofuran, and/or 1,4-dioxane, at −20 to 60° C.

The subsequent cleavage of an olefinic bond by ozonolysis is conducted with ozone, preferably in dichloromethane at −50 to −78° C. The intermediate obtained thereafter may be transformed into a carbonyl compound by treatment with e.g. dimethyl sulfide, zinc combined with acetic acid, hydrogen in the presence of palladium, or triphenylphosphine. Treatment of the intermediate with sodium borohydride or lithium aluminum hydride affords the corresponding hydroxy compound.

The subsequent epoxidation of an olefinic bond is preferably conducted with m-chloroperbenzoic acid (mCPBA), hydrogen peroxide combined with formic acid or acetic acid, or Oxone® combined with acetone or 1,1,1-trifluoroacetone, preferably in dichloromethane at −20 to 40° C. The oxirane ring can be opened with a hydride source, such as lithium aluminum hydride or lithium triethylborohydride, in an inert solvent, e.g. tetrahydrofuran, to furnish the hydroxy compound.

The subsequent Wacker oxidation of an olefinic bond is preferably conducted with $PdCl_2$ and CuCl or $CuCl_2$, in the presence of oxygen, in an aqueous solvent to provide the corresponding carbonyl compound.

The subsequent hydrocyanation of an olefinic bond can be conducted with 4-tolylsulfonyl cyanide in the presence of phenylsilane and a cobalt catalyst (see e.g. *Angew. Chem.* 2007, 119, 4603-6).

The subsequent formal addition of water to cyano groups to obtain the corresponding aminocarbonyl derivative can be done by treating an aqueous solution of the nitrile with a strong acid, e.g. sulfuric acid or hydrochloric acid, or base, e.g. NaOH or KOH, optionally at elevated temperature, preferably at 0 to 140° C. Extended heating, optionally under more forcing conditions, such as higher temperature or increased acid or base content, results in the formation of the corresponding carboxy derivative. Alternatively, the aminocarbonyl group may be obtained from the cyano group upon treatment with a transition metal, e.g. $PdCl_2$, in aqueous solution.

In the reactions described hereinbefore, any reactive group present, such as hydroxy, carbonyl, carboxy, amino, alkylamino, or imino, may be protected during the reaction by conventional protecting groups which are cleaved again after the reaction.

For example, a protecting group for a hydroxy group may be a trimethylsilyl, tert-butyldimethylsilyl, triisopropylsilyl, acetyl, pivaloyl, benzoyl, methyl, tert-butyl, allyl, trityl, benzyl, 4-methoxybenzyl, tetrahydropyranyl, methoxymethyl, ethoxymethyl, or 2-trimethylsilylethoxymethyl group, protecting groups for a carboxy group may be trimethylsilyl, methyl, ethyl, tert-butyl, allyl, benzyl, or tetrahydropyranyl, protecting groups for a ketone or aldehyde may be a ketal or acetal, respectively, e.g. derived from methanol, ethylene glycol, propane-1,3-diol, or propane-1,3-dithiol, protecting groups for an amino, alkylamino, or imino group may be methyl, formyl, acetyl, trifluoroacetyl, ethoxycarbonyl, tert-butoxycarbonyl, benzyloxycarbonyl, benzyl, 4-methoxybenzyl, or 2,4-dimethoxybenzyl and for the amino group additionally phthalyl and tetrachlorophthalyl, and protecting groups for a terminal alkyne may be trimethylsilyl, triisopropylsilyl, tert-butyldimethylsilyl, or 2-hydroxy-prop-2-yl.

Any acyl protecting group may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or in the presence of an alkali metal base such as lithium hydroxide, sodium hydroxide, or potassium hydroxide at temperatures between 0 and 120° C., preferably between 10 and 100° C. The transformation may be conducted aprotically with e.g. iodotrimethylsilane in dichloromethane or 1,2-dichlorethane at −70 to 60° C. Trifluoroacetyl is also cleaved by treating with an acid such as hydrochloric acid optionally in a solvent such as acetic acid at temperatures between 50 and 120° C. or by treating with aqueous sodium hydroxide solution optionally in an additional solvent such as tetrahydrofuran or methanol at temperatures between 0 and 80° C.

Any acetal or ketal protecting group used may be cleaved, for example, hydrolytically in an aqueous solvent, e.g. water, isopropanol/water, acetic acid/water, tetrahydro-furan/water, or 1,4-dioxane/water, in the presence of an acid such as acetic acid, trifluoroacetic acid, hydrochloric acid, or sulfuric acid at temperatures between 0 and 120° C., preferably between 10 and 100° C. Iodotrimethylsilane in dichloromethane is a variant to achieve this transformation aprotically.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide. Acids such as e.g. hydrochloric acid, trifluoroacetic acid, or acetic acid may also be suitable. The cleavage usually takes place at comparatively low temperatures, e.g. between −60 and 60° C. Silyl groups other than trimethylsilyl are preferentially cleaved in the presence of an acid, e.g. trifluoroacetic acid, hydrochloric acid, or sulfuric acid, at temperatures between 0 and 100° C. A particularly suited cleaving method for silyl groups is based on the use of fluoride salts, e.g. tetrabutylammonium fluoride, hydrogen fluoride, or potassium fluoride, in organic solvents, such as for example diethyl ether, tetrahydrofuran, 1,4-dioxane, 1,2-dimethoxyethane, toluene, benzene, 1,2-dichloroethane, or dichloromethane at temperatures between −20 and 100° C.

A benzyl, methoxybenzyl, or benzyloxycarbonyl group is advantageously cleaved hydrogenolytically, e.g. with hydrogen in the presence of a catalyst such as palladium on carbon or palladium hydroxide, in a solvent such as methanol, ethanol, ethyl acetate, acetic acid or mixtures thereof optionally in the presence of an acid such as hydrochloric acid at temperatures between 0 and 100° C., preferably between 20 and 60° C., and at hydrogen pressures of 1 to 10 bar, preferably 3 to 5 bar. Trimethylsilyl iodide, boron trichloride, or boron trifluoride in the presence of a scavenger such as anisol, thioanisol, or pentamethylbenzene may also be used with benzylether derivatives. An electron-rich benzyl residue such as methoxybenzyl may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tert-butyl or tert-butyloxycarbonyl group is preferably cleaved by treating with an acid such as trifluoroacetic acid, sulfuric acid, or hydrochloric acid or by treating with iodotrimethylsilane optionally using a solvent such as methylene chloride, 1,4-dioxane, methanol, isopropanol, water, or diethylether.

A methyl group at an tertiary amine may be cleaved by the treatment with 1-chloro-ethyl chloroformate or vinyl chloroformate. Hydrobromic acid and boron tribromide are particularly suited for the cleavage of methylethers.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. For example, such salts include acetates, ascorbates, benzenesulfonates (besylates), benzoates, bicarbonates, bitartrates, bromides/hydrobromides, Ca-edetates/edetates, camsylates, carbonates, chlorides/hydrochlorides, citrates, ethane disulfonates (edisylates), estolates, esylates, fumarates, gluceptates, gluconates, glutamates, glycolates, glycollylarsanilates, hexylresorcinates, hydrabamines, hydroxymaleates, hydroxynaphthoates, iodides, isothionates, lactates, lactobionates, malates, maleates, mandelates, methanesulfonates (mesylates), mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates (tosylates), triethiodides, ammonium, benzathines, chlorprocaines, cholines, diethanolamines, ethylenediamines, meglumines, and procaines. Further pharmaceutically acceptable salts can be formed with cations from metals like aluminum, calcium, lithium, magnesium, potassium, sodium, zinc, and the like (also see Pharmaceutical salts, Birge, S. M. et al., J. Pharm. Sci., (1977), 66, 1-19). Some of the salts mentioned above may also be useful for purifying or isolating the compounds of the invention.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetate salts), also comprise a part of the invention.

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly an inhibitory effect on the enzyme 11-beta-hydroxysteroid dehydrogenase 1 (11beta-HSD1).

Biological Examples

The biological properties (inhibitory activity on 11β-hydroxysteroid dehydrogenase 1) of the new compounds may be investigated as follows:

In vitro inhibition of 11β-HSD1 by test compounds is determined with HTRF (Homogeneous Time-Resolved Fluorescence) technology (cisbio international, France) detecting cortisol generated from cortisterone by human liver microsomes. Briefly, compounds are incubated for 1 hour at 37° C. in Tris buffer (20 mM tris, 5 mM EDTA, pH 6.0) containing NADPH (200 µM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction is typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contains incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contains a calibration curve with cortisol to transform the fluorescent data into cortisol concentrations. Percent inhibition (% CTL) of each compound is determined relative to the carbenoxolone signal and $IC_{50}$ curves are generated.

The compounds of general formula I according to the invention for example have $IC_{50}$ values below 10000 nM, particularly below 1000 nM, most preferably below 500 nM.

TABLE 2

Inhibitory activity on 11β-HSD 1 of the Examples (Ex) compiled in the experimental part

| Ex | $IC_{50}$ [nM] |
|---|---|
| 1 | 320 |
| 2 | 201 |
| 3 | 389 |
| 4 | 50 |
| 5 | 1262 |
| 6 | 257 |
| 7 | 2651 |
| 8 | 1279 |
| 9 | 386 |
| 10 | 465 |
| 11 | 28 |
| 12 | 756 |
| 13 | 377 |
| 14 | 634 |
| 15 | 41 |
| 16 | >10000 |
| 17 | >10000 |
| 18 | 183 |
| 19 | 168 |
| 20 | 547 |
| 21 | 645 |
| 22 | 330 |
| 23 | 296 |
| 24 | 794 |
| 25 | 80 |

TABLE 2-continued

Inhibitory activity on 11β-HSD 1 of the Examples (Ex) compiled in the experimental part

| Ex | IC$_{50}$ [nM] |
|---|---|
| 26 | 378 |
| 27 | 2502 |
| 28 | 3500 |
| 29 | 401 |
| 30 | 69 |
| 31 | 69 |
| 32 | 1948 |
| 33 | 65 |
| 34 | 35 |
| 35 | 72 |
| 36 | 658 |
| 37 | 39 |
| 38 | 95 |
| 39 | 679 |
| 40 | 35 |
| 41 | 902 |
| 42 | 34 |
| 43 | 869 |
| 44 | 13 |
| 45 | 49 |
| 46 | 665 |
| 47 | 3182 |
| 48 | 330 |
| 49 | 324 |
| 50 | 30 |
| 51 | 650 |
| 52 | 82 |
| 53 | 128 |
| 54 | 2381 |
| 55 | 23 |
| 56 | 967 |
| 57 | 1714 |
| 58 | 81 |
| 59 | 1713 |
| 60 | 2459 |
| 61 | 235 |
| 62 | 118 |
| 63 | 974 |
| 64 | 28 |
| 65 | 162 |
| 66 | 41 |
| 67 | 882 |
| 68 | 56 |
| 69 | 1508 |
| 70 | 13 |
| 71 | 188 |
| 72 | 3009 |
| 73 | 108 |
| 74 | 1855 |
| 75 | 135 |
| 76 | 389 |
| 77 | 57 |
| 78 | 21 |
| 79 | 26 |
| 80 | 143 |
| 81 | 124 |
| 82 | 101 |
| 83 | 220 |
| 84 | 28 |
| 85 | 111 |
| 86 | 1158 |
| 87 | 745 |
| 88 | 27 |
| 89 | 65 |
| 90 | 304 |
| 91 | 339 |
| 92 | 55 |
| 93 | 681 |
| 94 | 11 |
| 95 | 109 |
| 96 | 103 |
| 97 | 805 |
| 98 | 119 |
| 99 | 1370 |
| 100 | 79 |
| 101 | 923 |
| 102 | 28 |
| 104 | 87 |
| 105 | 79 |
| 106 | 795 |
| 107 | 24 |
| 108 | 42 |
| 109 | 54 |
| 110 | 12 |
| 111 | 100 |
| 112 | 103 |
| 113 | 73 |
| 114 | 1866 |
| 115 | 27 |
| 116 | 495 |
| 117 | 231 |
| 118 | 46 |
| 119 | 488 |
| 120 | 13 |
| 121 | 188 |
| 122 | 16 |
| 123 | 67 |
| 124 | 367 |
| 125 | 2525 |
| 126 | 32 |
| 127 | 568 |
| 128 | 86 |
| 129 | 113 |
| 130 | 403 |

In view of their ability to inhibit the enzyme 11-beta-hydroxysteroid dehydrogenase 1 (11beta-HSD1), the compounds of general formula I according to the invention are suitable for the treatment and/or preventative treatment of all those conditions or diseases which may be affected by the inhibition of the 11-beta-hydroxysteroid dehydrogenase 1 (11beta-HSD1) activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances may also be suitable for preventing beta-cell degeneration such as e.g. apoptosis or necrosis of pancreatic beta-cells. The substances may also be suitable for improving or restoring the functionality of pancreatic cells, and also of increasing the number and size of pancreatic beta-cells. The compounds according to the invention may also be used as diuretics or antihypertensives and are suitable for the prevention and treatment of acute renal failure.

Additionally, inhibition of 11-beta-hydroxysteroid dehydrogenase 1 (11beta-HSD1) has been shown to lower intraocular pressure in subjects with ocular hypertension, therefore the compounds could be used to treat glaucoma.

In view of the role of 11-beta-hydroxysteroid dehydrogenase 1 (11beta-HSD1) in modulating cortisol levels for interaction with the glucocorticoid receptor and the known role of excess glucocorticoids in bone loss, the compounds may have beneficial effects against osteoporosis.

Stress and/or glucocorticoids have been shown to influence cognitive function, and excess cortisol has been associated with brain neuronal loss or dysfunction. Treatment with an 11-beta-hydroxysteroid dehydrogenase 1 (11beta-HSD1) inhibitor may result in amelioration or prevention of cognitive impairment. Such compounds may also be useful in treating anxiety or depression.

The dynamic interaction between the immune system and the HPA (hypothalamopituitary-adrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11-beta-hydroxysteroid dehydrogenase 1 (11beta-HSD1) inhibitor would bolster a temporal immune response in association with immunization to ensure that a cell based response would be obtained, and as such could be useful in immunomodulation.

In particular, the compounds according to the invention, including the physiologically acceptable salts thereof, are suitable for the prevention or treatment of diabetes, particularly type 1 and type 2 diabetes mellitus, and/or diabetic complications.

In a further aspect of the present invention the present invention relates to methods for the treatment or prevention of above mentioned diseases and conditions, which method comprises the administration of an effective amount of a compound of general formula I to a human being.

The dose range of the compounds of general formula I applicable per day is usually from 1 to 1000 mg, preferably from 5 to 800 mg, more preferably from 5 to 500 mg by oral route, in each case administered 1 to 4 times a day.

Each dosage unit may conveniently contain from 1 to 1000 mg, preferably 100 to 500 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, those which potentiate the therapeutic effect of an 11-beta-hydroxysteroid dehydrogenase 1 (11beta-HSD1) inhibitor according to the invention with respect to one of the indications mentioned and/or which allow the dosage of an 11-beta-hydroxysteroid dehydrogenase 1 (11beta-HSD1) inhibitor according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, remogliflozin etabonate, sergliflozin, canagliflozin), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, Linagliptin), alpha2-antagonists, insulin and insulin analogues, GPR40 agonists such as TAK-875, GPR119 agonists, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, taso-sartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt thereof combined with at least one of the active substances described above as a combination partner, for preparing a pharmaceutical composition which is suitable for the treatment or prevention of diseases or conditions which can be affected by inhibiting the enzyme 11-beta-hydroxysteroid dehydrogenase 1 (11beta-HSD1). These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of times. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it:

Analytical HPLC parameters employed for characterization of products (UV/VIS detection at 210-500 nM):

| method 1 column | Waters Xbridge C18, 30 × 4.6 mm, 2.5 µm | method 2 column | Waters Xbridge C18, 30 × 4.6 mm, 2.5 µm |
|---|---|---|---|
| mobile phase | A: water + 0.1% NH$_3$ B: methanol | mobile phase | A: water + 0.1% NH$_3$ B: methanol |
| time (min) | A % | B % | time (min) | A % | B % |
| 0.00 | 90 | 10 | 0.00 | 90 | 10 |
| 0.15 | 90 | 10 | 0.08 | 90 | 10 |
| 4.00 | 0 | 100 | 2.10 | 0 | 100 |
| 4.40 | 0 | 100 | 2.50 | 0 | 100 |
| 4.55 | 90 | 10 | 2.60 | 90 | 10 |
| 5.00 | 90 | 10 | 2.85 | 90 | 10 |
| flow rate | 1.6 mL/min | flow rate | 2.8 mL/min |

-continued

| method 3 column | Merck Cromolith Speed ROD, RP18e, 50 × 4.6 mm | method 4 column | Waters Xbridge C18, 30 × 3.0 mm, 2.5 µm |
|---|---|---|---|
| mobile phase | A: water + 0.1% HCO$_2$H B: acetonitrile + 0.1% HCO$_2$H | mobile phase | A: water + 0.1% NH$_3$ B: methanol |
| time (min) | A % | B % | time (min) | A % | B % |
| 0.00 | 90 | 10 | 0.00 | 90 | 10 |
| 4.50 | 10 | 90 | 2.20 | 0 | 100 |
| 5.00 | 10 | 90 | 2.40 | 0 | 100 |
| 5.50 | 90 | 10 | 2.60 | 90 | 10 |
| — | — | — | 2.80 | 90 | 10 |
| flow rate | 1.5 mL/min | flow rate | 1.5 mL/min |

| method 5 column | Waters Xbridge C18, 30 × 4.6 mm, 2.5 µm | method 6 column | StableBond SB-C18 30 × 4.6 mm, 1.8 µm |
|---|---|---|---|
| mobile phase | A: water + 0.1% F$_3$CCO$_2$H B: methanol | mobile phase | A: water + 0.1% F$_3$CCO$_2$H B: methanol |
| time (min) | A % | B % | time (min) | A % | B % |
| 0.00 | 90 | 10 | 0.00 | 90 | 10 |
| 1.50 | 0 | 100 | 0.18 | 0 | 100 |
| 1.75 | 0 | 100 | 2.00 | 0 | 100 |
| 1.80 | 90 | 10 | 2.15 | 90 | 10 |
| 2.00 | 90 | 10 | 2.35 | 90 | 10 |
| flow rate | 3.1 mL/min | flow rate | 3 mL/min |

| method 7 column | Waters Xbridge Phenyl, 30 × 3.0 mm, 2.5 µm | method 8 column | StableBond SB-C18 30 × 4.6 mm, 1.8 µm |
|---|---|---|---|
| mobile phase | A: water + 0.1% F$_3$CCO$_2$H B: methanol | mobile phase | A: water + 0.1% F$_3$CCO$_2$H B: methanol |
| time (min) | A % | B % | time (min) | A % | B % |
| 0.00 | 90 | 10 | 0.00 | 90 | 10 |
| 1.70 | 0 | 100 | 1.80 | 0 | 100 |
| 1.90 | 0 | 100 | 2.00 | 0 | 100 |
| 2.05 | 90 | 10 | 2.15 | 90 | 10 |
| 2.20 | 90 | 10 | 2.35 | 90 | 10 |
| flow rate | 1.75 mL/min | flow rate | 1.75 mL/min |

Intermediate 1

6,6-Diallyl-3-[(S)-1-(4-bromo-phenyl)-ethyl]-[1,3]oxazinan-2-one

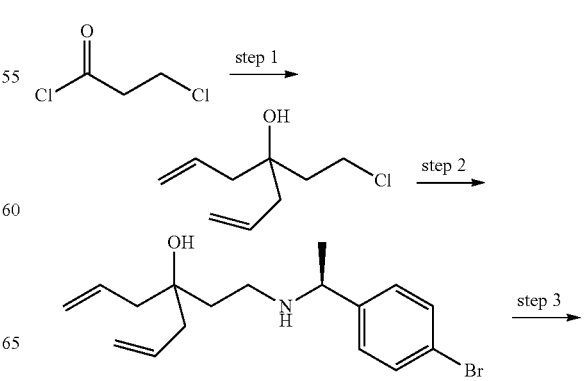

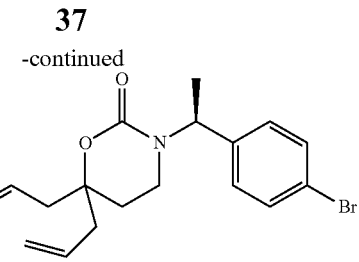

Step 1: 4-(2-chloro-ethyl)-hepta-1,6-dien-4-ol

3-Chloro-propionyl chloride (5.00 g) dissolved in tetrahydrofuran (50 mL) is added dropwise to a 1 M solution of allylmagnesium bromide in diethyl ether (72 mL) cooled to −15° C. The solution is warmed in the cooling bath to room temperature over a period of 2 h and stirred at room temperature overnight. Water is then added and the resulting mixture is neutralized using 4 M aqueous hydrochloric acid. The mixture is extracted with diethyl ether (3×) and the combined extracts are washed with water (2×). The organic phase is dried ($Na_2SO_4$) and the solvent is evaporated to afford the crude title compound. Yield: 7.87 g (ca. 85% pure).

Step 2: 4-{2-[(S)-1-(4-bromo-phenyl)-ethylamino]-ethyl}-hepta-1,6-dien-4-ol

A mixture of 4-(2-chloro-ethyl)-hepta-1,6-dien-4-ol (7.87 g), (S)-1-(4-bromo-phenyl)-ethylamine (13.52 g), $K_2CO_3$ (9.34 g), KI (8.23 g), and acetonitrile (150 mL) is stirred at reflux temperature overnight. After cooling to room temperature, the mixture is concentrated under reduced pressure and water is added to the residue. The resulting mixture is extracted with ethyl acetate (3×), and the combined extracts are washed with brine and dried ($MgSO_4$). The solvent is evaporated and the residue is chromatographed on silica gel (cyclohexane/ethyl acetate 1:1→0:1) to afford the title compound as an oil. Yield: 8.36 g (55% of theory); Mass spectrum ($ESI^+$): m/z=338/340 (Br) $[M+H]^+$.

Step 3: 6,6-diallyl-3-[(S)-1-(4-bromo-phenyl)-ethyl]-[1,3]oxazinan-2-one

Triphosgene (6.90 g) is added to a solution of 4-{2-[(S)-1-(4-bromo-phenyl)-ethylamino]-ethyl}-hepta-1,6-dien-4-ol (7.86 g) and ethyl-diisopropyl-amine (4 mL) in dichloromethane (150 mL) chilled in an ice bath. The cooling bath is removed and the solution is stirred at room temperature overnight. Water is added and the organic phase is then separated. The organic phase is dried ($Na_2SO_4$) and concentrated to give the crude title compound that is used without further purification. Yield: 8.65 g (ca. 90% pure); LC (method 1): $t_R$=4.03 min; Mass spectrum ($ESI^+$): m/z=364/366 (Br) $[M+H]^+$.

Intermediate 2

3-[(S)-1-(4-Bromo-phenyl)-ethyl]-1-oxa-3-aza-spiro[5.5]undecane-2,9-dione

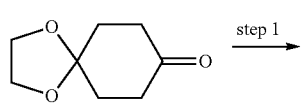

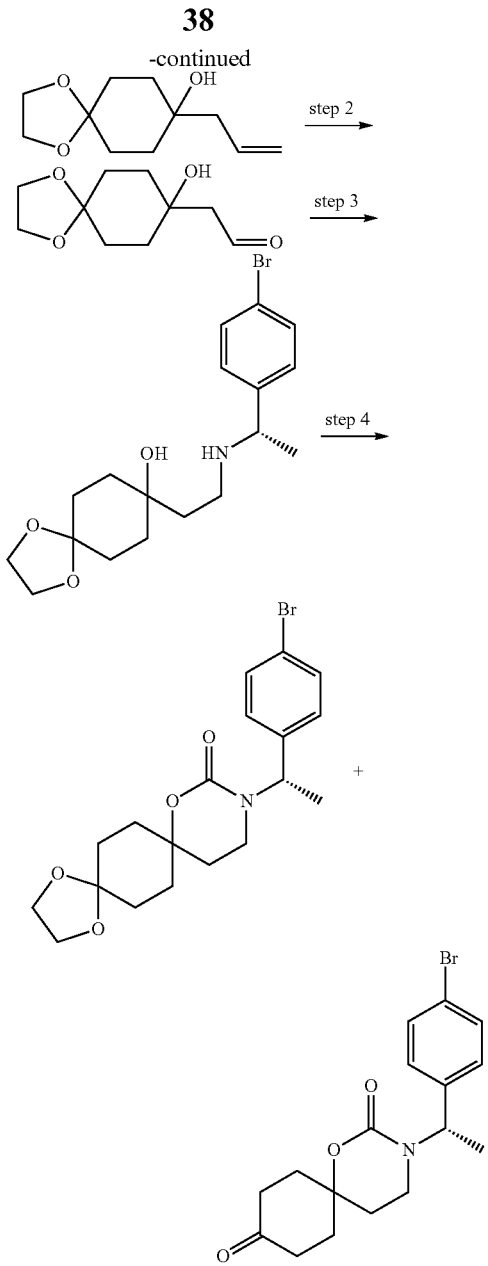

Step 1: 8-allyl-1,4-dioxa-spiro[4.5]decan-8-ol

Allyl bromide (11.1 mL) is added dropwise to a vigorously stirred mixture of zinc powder (8.37 g), 1,4-dioxa-spiro[4.5]decan-8-one (10.00 g), saturated aqueous $NH_4Cl$ solution (70 mL), and tetrahydrofuran (150 mL) at room temperature. The solution is stirred at room temperature until the starting material is completely consumed (TLC or HPLC). The mixture is extracted with tert-butyl methyl ether, and the combined extracts are washed with brine and dried ($Na_2SO_4$). The solvent is evaporated under reduced pressure to give the crude title compound. Yield: 12.59 g (ca. 90% pure); Mass spectrum ($ESI^+$): m/z=181 $[M+H-H_2O]^+$.

Step 2: (8-hydroxy-1,4-dioxa-spiro[4.5]dec-8-yl)-acetaldehyde $NaIO_4$ (18.13 g) followed by $OsO_4$ (4% in water, 0.96 mL) is added to a mixture of 8-allyl-1,4-dioxa-spiro[4.5]decan-8- ol (12.59 g), diethyl ether (65 ml), and water (85 mL) at room temperature. The mixture is vigorously stirred at room temperature overnight, before aqueous Na$_2$S$_2$O$_3$ solution (50 mL) is added and stirring is continued for another 45 min. The combined organic phases are washed with water, dried (MgSO$_4$), and concentrated. The crude product is used without further purification. Yield: 2.68 g (ca. 70% pure); Mass spectrum (ESI$^+$): m/z=201 [M+H]$^+$.

Step 3: 8-{2-[(S)-1-(4-bromo-phenyl)-ethylamino]-ethyl}-1,4-dioxa-spiro[4.5]decan-8-ol (S)-1-(4-Bromo-phenyl)-ethylamine (2.68 g), sodium triacetoxyborohydride (2.84 g), and acetic acid (0.77 mL) are added in the given order to a solution of (8-hydroxy-1,4-dioxa-spiro[4.5]dec-8-yl)-acetaldehyde (7.86 g) in tetrahydrofuran (150 mL) at room temperature. The resulting mixture is stirred at room temperature overnight. Water (100 mL) and 1 M aqueous NaOH solution (100 mL) are then added and the mixture is stirred for another 20 min. The mixture is extracted with ethyl acetate, and the combined extracts are washed with water and brine. After drying (MgSO$_4$), the solvent is evaporated to give the crude title compound that is used without further purification. Yield: 2.91 g (crude); LC (method 3): t$_R$=2.00 min; Mass spectrum (ESI$^+$): m/z=384/386 (Br) [M+H]$^+$.

Step 4: 11-[(S)-1-(4-bromo-phenyl)-ethyl]-1,4,9-trioxa-11-aza-dispiro[4.2.5.2]pentadecan-10-one and 3-[(S)-1-(4-bromo-phenyl)-ethyl]-1-oxa-3-aza-spiro[5.5]undecane-2,9-dione The title compounds are prepared from 8-{2-[(S)-1-(4-bromo-phenyl)-ethylamino]-ethyl}-1,4-dioxa-spiro[4.5]decan-8-ol and triphosgene following a procedure analogous to that described in step 3 of Intermediate 1. The ketal group is partially cleaved under these conditions to give a mixture of the title compounds that is separated by chromatography on silica gel (cyclohexane/ethyl acetate 9:1→1:1). 11-[(S)-1-(4-bromo-phenyl)-ethyl]-1,4,9-trioxa-11-aza-dispiro[4.2.5.2] pentadecan-10-one: Yield: 6% of theory; LC (method 1): t$_R$=3.65 min; Mass spectrum (ESI$^+$): m/z=410/412 (Br) [M+H]$^+$.

3-[(S)-1-(4-bromo-phenyl)-ethyl]-1-oxa-3-aza-spiro[5.5] undecane-2,9-dione: Yield: 19% of theory; Mass spectrum (ESI$^+$): m/z=366/368 (Br) [m+H]$^+$.

Alternatively, Intermediate 2 is obtained following the synthetic route described below:

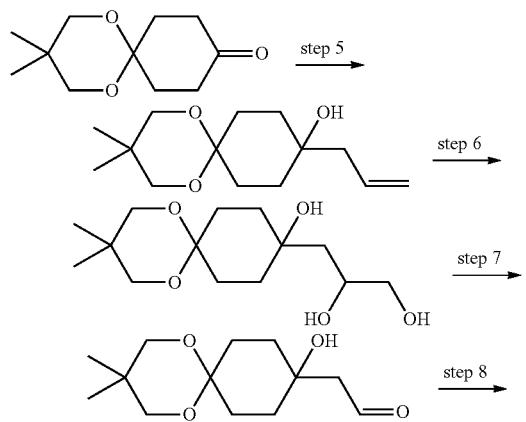

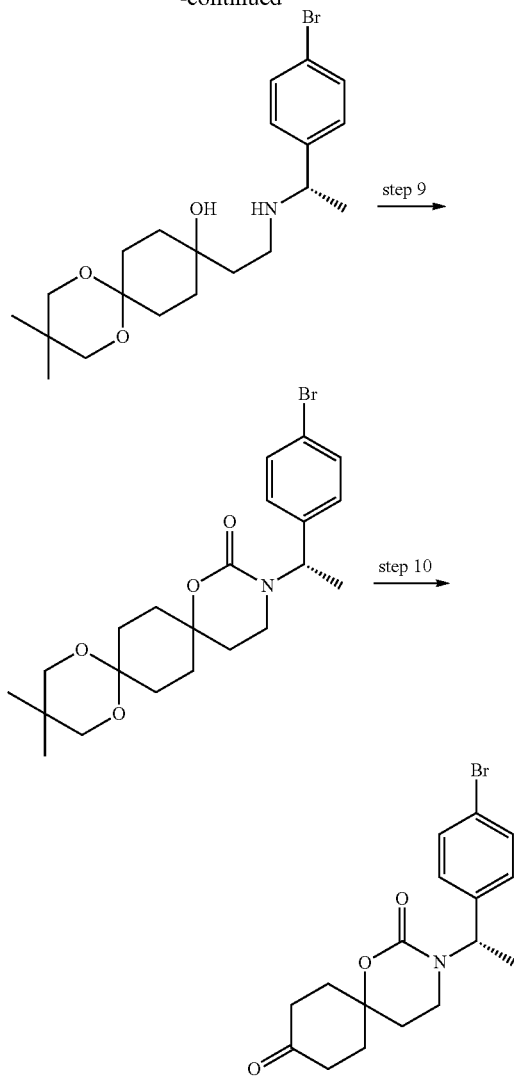

Step 5: 9-allyl-3,3-dimethyl-1,5-dioxa-spiro[5.5]undecan-9-ol

The title compound is prepared from 3,3-dimethyl-1,5-dioxa-spiro[5.5]undecan-9-one and allyl bromide following a procedure analogous to that described in Step 1 of Intermediate 2. Yield: quantitative; Mass spectrum (ESI$^+$): m/z=223 [M+H—H$_2$O]$^+$.

Step 6: 3-(9-hydroxy-3,3-dimethyl-1,5-dioxa-spiro[5.5]undec-9-yl)-propane-1,2-diol K$_2$OsO$_4$*2H$_2$O (0.23 g) and N-methyl-morpholine-N-oxide (3.22 g) are added to a solution of 9-allyl-3,3-dimethyl-1,5-dioxa-spiro[5.5]undecan-9-ol (6.00 g) in a mixture of tetrahydrofuran (75 mL) and water (35 mL) chilled in an ice bath. The cooling bath is removed and the solution is stirred at room temperature overnight. Aqueous Na$_2$S$_2$O$_3$ solution (50 mL) is then added and stirring is continued for another 45 min. The tetrahydrofuran is evaporated and the residue is extracted with dichloromethane (3×) and ethyl acetate (3×). The combined extracts are dried (MgSO$_4$) and the solvent is evaporated to give the crude product. Yield: 4.63 g (crude); Mass spectrum (ESI$^+$): m/z=275 [m+H]$^+$.

Step 7: (9-hydroxy-3,3-dimethyl-1,5-dioxa-spiro[5.5]undec-9-yl)-acetaldehyde Water (7 mL) and NaIO$_4$ (5.41 g) are added to a solution of 3-(9-hydroxy-3,3-dimethyl-1,5-dioxa-spiro[5.5]undec-9-yl)-propane-1,2-diol (4.63 g) in dichloromethane (70 mL) chilled in an ice bath. The cooling bath is removed and the resulting mixture is vigorously stirred at room temperature overnight. The mixture is then filtered and the filtrate is dried (Na$_2$SO$_4$) and concentrated to give the crude title compound that is directly subjected to the next reaction step. Yield: 4.28 g (crude); Mass spectrum (ESI$^+$): m/z=243 [M+H]$^+$.

Step 8: 9-{2-[(S)-1-(4-bromo-phenyl)-ethylamino]-ethyl}-3,3-dimethyl-1,5-dioxa-spiro[5.5]undecan-9-ol The title compound is prepared from (9-hydroxy-3,3-dimethyl-1,5-dioxa-spiro[5.5]undec-9-yl)-acetaldehyde and (S)-1-(4-bromo-phenyl)-ethylamine following a procedure analogous to that described in Step 3 of Intermediate 2. Yield: 71% of theory; LC (method 1): t$_R$=4.06 min; Mass spectrum (ESI$^+$): m/z=426/428 (Br) [M+H]$^+$.

Step 9: 3-[(S)-1-(4-bromo-phenyl)-ethyl]-12,12-dimethyl-1,10,14-trioxa-3-aza-dispiro[5.2.5.2]hexadecan-2-one The title compound is prepared from 9-{2-[(S)-1-(4-bromo-phenyl)-ethylamino]-ethyl}-3,3-dimethyl-1,5-dioxa-spiro[5.5]undecan-9-ol and triphosgene following a procedure analogous to that described in Step 4 of Intermediate 2; besides the title compound 3-[(S)-1-(4-bromo-phenyl)-ethyl]-1-oxa-3-aza-spiro[5.5]undecane-2,9-dione (36% of theory) is obtained. Yield: 40% of theory; Mass spectrum (ESI$^+$): m/z=452/454 (Br) [M+H]$^+$.

Step 10: 3-[(S)-1-(4-bromo-phenyl)-ethyl]-1-oxa-3-aza-spiro[5.5]undecane-2,9-dione A solution of 3-[(S)-1-(4-bromo-phenyl)-ethyl]-12,12-dimethyl-1,10,14-trioxa-3-aza-dispiro[5.2.5.2]hexadecan-2-one (0.75 g), aqueous hydrochloric acid (5 mL), and acetone (10 mL) is stirred at room temperature overnight. The acetone is then evaporated, and the residue is diluted with saturated aqueous K$_2$CO$_3$ solution and extracted with ethyl acetate. The combined extracts are washed with water and brine, dried (MgSO$_4$), and concentrated to give the crude title compound that is used without further purification. Yield: 0.70 g (ca. 65% pure); Mass spectrum (ESI$^+$): m/z=366/368 (Br) [M+H]$^+$.

Intermediate 3

(2S,5R)-2-Hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one

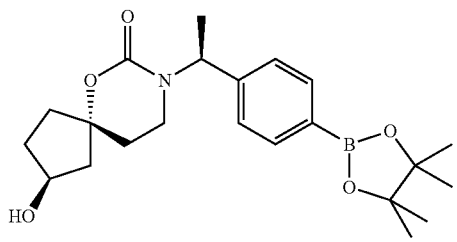

A flask charged with a stir bar, (2S,5R)-8-[(S)-1-(4-bromo-phenyl)-ethyl]-2-hydroxy-6-oxa-8-aza-spiro[4.5]decan-7-one (Example 3, 1.00 g), bis(pinacolato)diboron (0.93 g), potassium acetate (0.97 g), and dimethyl sulfoxide (15 mL) is sparged with argon for 5 min. 1,1'-[Bis(diphenyl-phosphino)ferrocene]dichloropalladium dichloromethane complex (0.12 g) is then added and the mixture is heated to 90° C. and stirred at this temperature for 4 h. After cooling to room temperature, water is added and the resulting mixture is extracted with ethyl acetate. The combined extracts are washed with brine, dried (Na$_2$SO$_4$), and concentrated. The residue is taken up in tert-butyl methyl ether and stirred in an ice bath for 20 min. The precipitate formed is separated by filtration and dried to give the title compound as a solid. Yield: 0.45 g (40% of theory); Mass spectrum (ESI$^+$): m/z=402 [M+H]$^+$.

Intermediate 4

Mixture of (2S,5S)—,(2R,5R)—, and (2R,5S)-2-Hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one

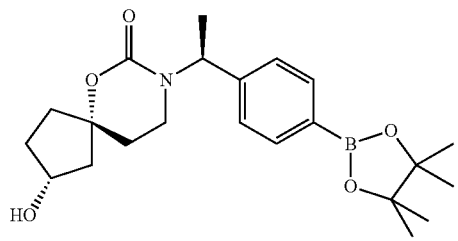 [SMILES: C[C@@H](c1ccc(B2OC(C)(C)C(C)(C)O2)cc1)N1CC[C@@]2(CC[C@H](O)C2)OC1=O]

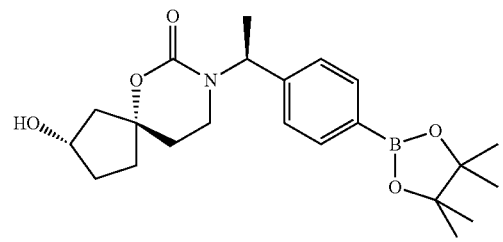

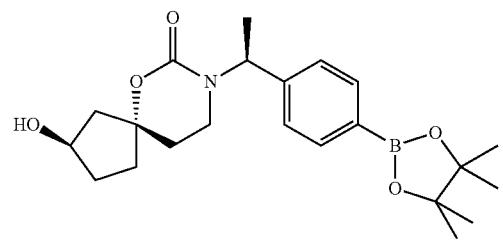

The title compound is prepared from a mixture of (2S,5S)—, (2R,5R)—, and (2R,5S)-8-[(S)-1-(4-bromo-phenyl)-ethyl]-2-hydroxy-6-oxa-8-aza-spiro[4.5]decan-7-one (ca. 1:1:0.3, Examples 4/5/6) and bis(pinacolato)-diboron following a procedure analogous to that described in Intermediate 3. The crude mixture of the three title compounds is used without further purification.

Intermediate 5

(2R,5S)-2-Hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one

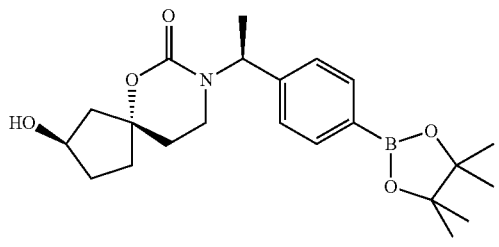 [SMILES: C[C@@H](c1ccc(B2OC(C)(C)C(C)(C)O2)cc1)N1CC[C@]2(CC[C@@H](O)C2)OC1=O]

The title compound is prepared from (2R,5S)-8-[(S)-1-(4-bromo-phenyl)-ethyl]-2-hydroxy-6-oxa-8-aza-spiro[4.5]decan-7-one (Example 4) and bis(pinacolato)-diboron following a procedure analogous to that described in Intermediate 3. Yield: 63% of theory; Mass spectrum (ESI$^+$): m/z=402 [M+H]$^+$.

Intermediate 6 trans-4-Nitro-benzoic acid 3-[(S)-1-(4-bromo-phenyl)-ethyl]-2-oxo-1-oxa-3-aza-spiro[5.5]undec-9-yl ester

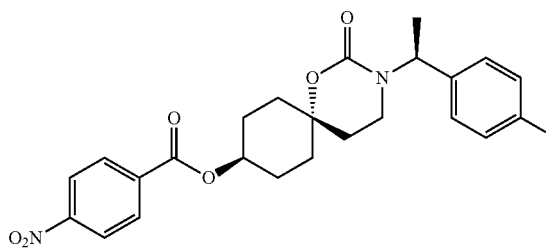

Triphenylphosphine (0.78 g), 4-nitrobenzoic acid (0.54 g), and diisopropyl diazodicarboxylate (0.59 mL) are added in the given order to a solution of 3-[(S)-1-(4-bromophenyl)ethyl]-cis-9-hydroxy-1-oxa-3-azaspiro[5.5]undecan-2-one (contains ca. 20% of corresponding trans isomer, 0.50 g) in tetrahydrofuran (5 mL) at room temperature. The resulting mixture is stirred at room temperature overnight and then concentrated. The residue is purified by HPLC on reversed phase (methanol/water) and then by MPLC on silica gel (cyclohexane/ethyl acetate 6:4→4:6) to give fractions of the title compound in varying mixtures with cis-4-nitro-benzoic acid 3-[(S)-1-(4-bromo-phenyl)-ethyl]-2-oxo-1-oxa-3-aza-spiro[5.5]undec-9-yl ester and a fraction of the pure title compound. Yield: 0.10 g (14% of theory, pure fraction); Mass spectrum (ESI$^+$): m/z=517/519 (Br) [M+H]$^+$.

Intermediate 7

12,12-Dimethyl-3-{(S)-[4-(4,4,5,5-tetramethyl-[1,3,2]dioxaborolan-2-yl)-phenyl]-ethyl}-1,10,14-trioxa-3-aza-dispiro[5.2.5.2]hexadecan-2-one

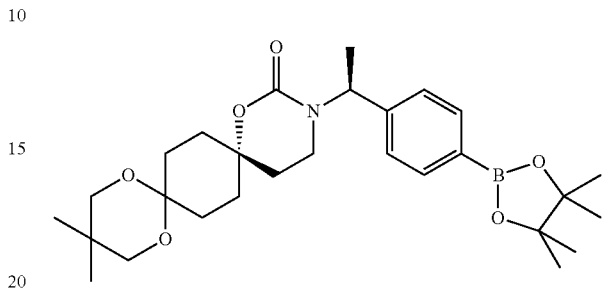

The title compound is prepared from 3-[(S)-1-(4-bromo-phenyl)-ethyl]-12,12-dimethyl-1,10,14-trioxa-3-aza-dispiro[5.2.5.2]hexadecan-2-one and bis(pinacolato)-diboron following a procedure analogous to that described in Intermediate 3. Yield: 65% of theory; Mass spectrum (ESI$^+$): m/z=500 [M+H]$^+$.

Intermediate 8

[(S)-1-(4-Bromo-phenyl)-ethyl]-[2-(7-hydroxy-1,4-dioxa-spiro[4.5]dec-7-yl)-ethyl]-carbamic acid methyl ester

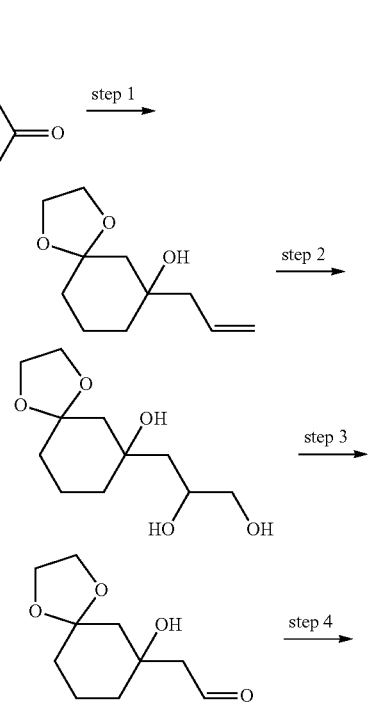

-continued

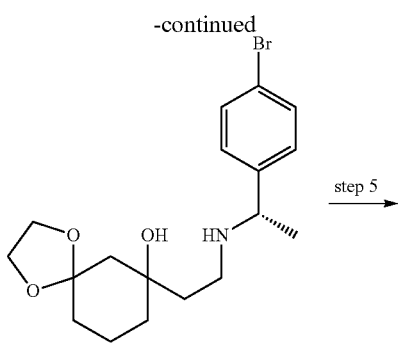

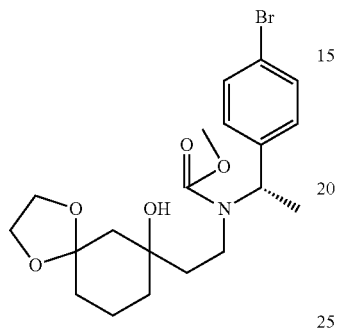

Step 1: 7-allyl-1,4-dioxa-spiro[4.5]decan-7-ol

The title compound is prepared from 1,4-dioxa-spiro[4.5]decan-7-one and allyl bromide following a procedure analogous to that described in Step 1 of Intermediate 2. Yield: 84% of theory; Mass spectrum (ESI$^+$): m/z=181 [M+H—H$_2$O]$^+$.

Step 2: 3-(7-hydroxy-1,4-dioxa-spiro[4.5]dec-7-yl)-propane-1,2-diol

The title compound is prepared from 7-allyl-1,4-dioxa-spiro[4.5]decan-7-ol following a procedure analogous to that described in Step 6 of Intermediate 2. Yield: 44% of theory; Mass spectrum (ESI$^+$): m/z=233 [M+H]$^+$.

Step 3: (7-hydroxy-1,4-dioxa-spiro[4.5]dec-7-yl)-acetaldehyde

The title compound is prepared from 3-(7-hydroxy-1,4-dioxa-spiro[4.5]dec-7-yl)-propane-1,2-diol following a procedure analogous to that described in Step 7 of Intermediate 2; the product is directly submitted to the next reaction step. Yield: 87% of theory; Mass spectrum (ESI$^+$): m/z=183 [M+H—H$_2$O]$^+$.

Step 4: 7-{2-[(S)-1-(4-bromo-phenyl)-ethylamino]-ethyl}-1,4-dioxa-spiro[4.5]decan-7-ol The title compound is prepared from (7-hydroxy-1,4-dioxa-spiro[4.5]dec-7-yl)-acetaldehyde and (S)-1-(4-bromophenyl)-ethylamine following a procedure analogous to that described in Step 3 of Intermediate 2. Yield: 68% of theory; LC (method 1): t$_R$=3.83 min; Mass spectrum (ESI$^+$): m/z=384/386 (Br) [M+H]$^+$.

Step 5: [(S)-1-(4-bromo-phenyl)-ethyl]-[2-(7-hydroxy-1,4-dioxa-spiro[4.5]dec-7-yl)-ethyl]-carbamic acid methyl ester Methyl chloroformate (0.20 mL) is added dropwise to a solution of 7-{2-[(S)-1-(4-bromo-phenyl)-ethylamino]-ethyl}-1,4-dioxa-spiro[4.5]decan-7-ol (0.50 g), triethylamine (0.4 mL), and pyridine (0.2 mL) in dichloromethane (10 mL) chilled in an ice bath. The solution is warmed to room temperature and stirred at this temperature overnight. Water is then added and the resulting mixture is extracted with dichloromethane. The combined extracts are washed with water (3×), dried (MgSO$_4$), and concentrated. The residue is purified by HPLC on reversed phase (methanol/water) to give the title compound. Yield: 0.30 g (50% of theory); Mass spectrum (ESI$^+$): m/z=442/444 (Br) [M+H]$^+$.

Intermediate 9

(7S)-10-[(S)-1-[4-(4,4,5,5-tetramethyl-1,3,2-dioxaborolan-2-yl)phenyl]ethyl]-1,4,8-trioxa-10-azadispiro[4.1.5$^7$.3$^5$]pentadecan-9-one

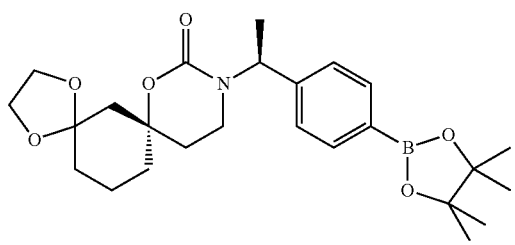 [SMILES: C[C@@H](c1ccc(B2OC(C)(C)C(C)(C)O2)cc1)N1CC[C@]2(CCCC3(C2)OCCO3)OC1=O]

The title compound is prepared from (7S)-10-[(S)-1-(4-bromophenyl)ethyl]-1,4,8-trioxa-10-azadispiro[4.1.5$^7$.3$^5$]pentadecan-9-one and bis(pinacolato)-diboron following a procedure analogous to that described in Intermediate 3. Yield: 55% of theory; Mass spectrum (ESI$^+$): m/z=458 [M+H]$^+$.

Intermediate 10

(7R)-10-[(S)-1-[4-(4,4,5,5-tetramethyl-1,3,2-dioxaborolan-2-yl)phenyl]ethyl]-1,4,8-trioxa-10-azadispiro[4.1.5$^7$.3$^5$]pentadecan-9-one

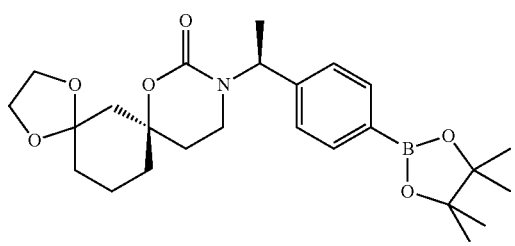 [SMILES: C[C@@H](c1ccc(B2OC(C)(C)C(C)(C)O2)cc1)N1CC[C@@]2(CCCC3(C2)OCCO3)OC1=O]

The title compound is prepared from (7R)-10-[(S)-1-(4-bromophenyl)ethyl]-1,4,8-trioxa-10-azadispiro[4.1.5$^7$.3$^5$]pentadecan-9-one and bis(pinacolato)-diboron following a procedure analogous to that described in Intermediate 3. Yield: 86% of theory; Mass spectrum (ESI$^+$): m/z=458 [M+H]$^+$.

Intermediate 11

9-{2-[(S)-1-(4-Methoxy-phenyl)-ethylamino]-ethyl}-3,3-dimethyl-1,5-dioxa-spiro[5.5]undecan-9-ol

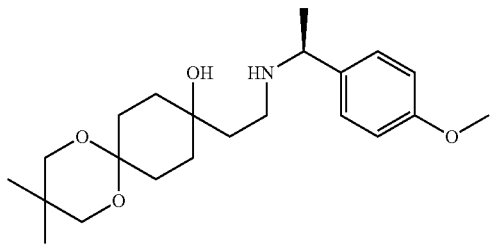

The title compound is prepared from (9-hydroxy-3,3-dimethyl-1,5-dioxa-spiro[5.5]undec-9-yl)-acetaldehyde and (S)-1-(4-methoxy-phenyl)-ethylamine following a procedure analogous to that described in Step 3 of Intermediate 2. Yield: 45% of theory; LC (method 1): $t_R$=1.44 min; Mass spectrum (ESI$^+$): m/z=378 [M+H]$^+$.

Intermediate 12

9-{2-[(S)-1-(4-Chloro-phenyl)-ethylamino]-ethyl}-3,3-dimethyl-1,5-dioxa-spiro[5.5]undecan-9-ol

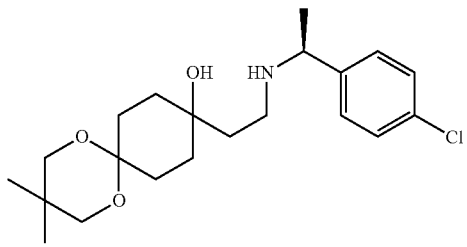 [SMILES: C[C@H](NCCC1(O)CCC2(CC1)OCC(C)(C)CO2)c1ccc(Cl)cc1]

The title compound is prepared from (9-hydroxy-3,3-dimethyl-1,5-dioxa-spiro[5.5]undec-9-yl)-acetaldehyde and (S)-1-(4-chloro-phenyl)-ethylamine following a procedure analogous to that described in Step 3 of Intermediate 2. Yield: 63% of theory; LC (method 1): $t_R$=1.55 min; Mass spectrum (ESI$^+$): m/z=382/384 (Cl) [M+H]$^+$.

Intermediate 13

4-[(S)-1-(12,12-Dimethyl-2-oxo-1,10,14-trioxa-3-aza-dispiro[5.2.5.2]hexadec-3-yl)-ethyl]-benzonitrile

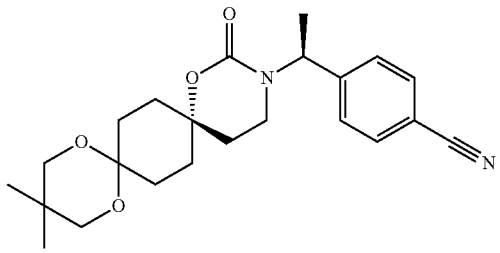

A flask charged with a stir bar, 12,12-dimethyl-3-{(S)-1-[4-(4,4,5,5-tetramethyl-[1,3,2]dioxaborolan-2-yl)-phenyl]-ethyl}-1,10,14-trioxa-3-aza-dispiro[5.2.5.2]hexadecan-2-one (1.09 g), tetrakis(triphenylphosphine)palladium (0.60 g), copper(I) thiophene-2-carboxylate (0.50 g), and benzyl thiocyanate (0.26 g) is sparged with argon for 5 min. 1,4-Dioxane (20 mL) is added and the resulting mixture is heated to 100° C. After stirring at 100° C. for 12 h, the mixture is cooled to room temperature, diluted with diethyl ether, and washed with saturated aqueous NH$_4$Cl solution, saturated aqueous NaHCO$_3$ solution, and brine. The organic phase is dried (MgSO$_4$), the solvent is evaporated, and the residue is chromatographed on silica gel (cyclohexane/ethyl acetate) to afford the title compound. Yield: 0.23 g (33% of theory); LC (method 4): $t_R$=1.27 min; Mass spectrum (ESI$^+$): m/z=399 [M+H]$^+$.

Intermediate 14

9-(2-{[(S)-(4-Bromo-phenyl)-cyclopropyl-methyl]-amino}-ethyl)-3,3-dimethyl-1,5-dioxa-spiro[5.5]undecan-9-ol

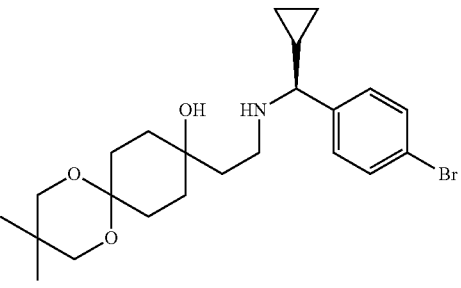 [SMILES: CC1(C)COC2(CCC(O)(CCN[C@H](c3ccc(Br)cc3)C3CC3)CC2)OC1]

The title compound is prepared from (9-hydroxy-3,3-dimethyl-1,5-dioxa-spiro[5.5]undec-9-yl)-acetaldehyde and (S)-(4-bromophenyl)(cyclopropyl)methanamine following a procedure analogous to that described in Step 3 of Intermediate 2. Yield: 71% of theory; LC (method 1): $t_R$=1.64 min; Mass spectrum (ESI$^+$): m/z=452/454 (Br) [M+H]$^+$.

Intermediate 15

4-{2-[(S)-1-(4-Bromo-phenyl)-ethylamino]-ethyl}-adamantane-1,4-diol

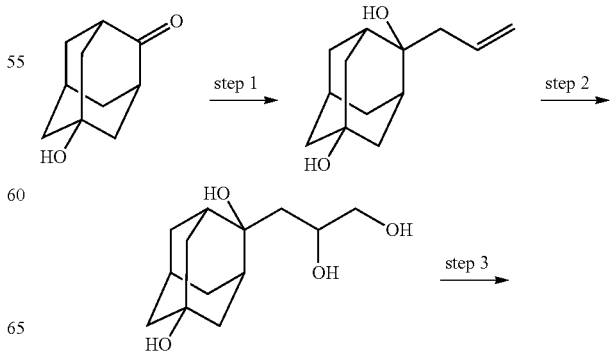

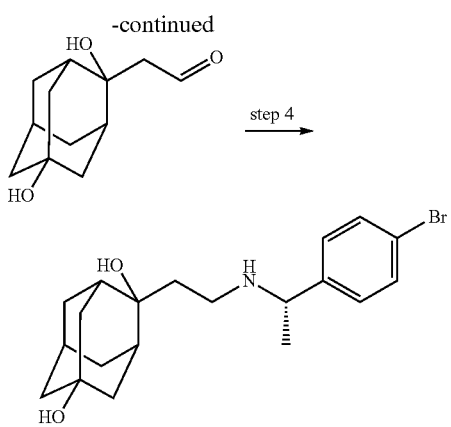

Step 1: 4-allyl-adamantane-1,4-diol

The title compound is prepared from 5-hydroxy-adamantan-2-one and allyl bromide following a procedure analogous to that described in Step 1 of Intermediate 2. Yield: quantitative; Mass spectrum (ESI$^+$): m/z=226 [M+NH$_4$]$^+$.

Step 2: 4-(2,3-dihydroxy-propyl)-adamantane-1,4-diol

The title compound is prepared from 4-allyl-adamantane-1,4-diol following a procedure analogous to that described in Step 6 of Intermediate 2. Yield: 32% of theory; Mass spectrum (ESI$^-$): m/z=287 [M+HCOO]$^-$.

Step 3: (2,5-dihydroxy-adamantan-2-yl)-acetaldehyde

The title compound is prepared from 4-(2,3-dihydroxy-propyl)-adamantane-1,4-diol following a procedure analogous to that described in Step 7 of Intermediate 2; the product is directly submitted to the next reaction step. Yield: quantitative; Mass spectrum (ESI$^+$): m/z=228 [M+NH$_4$]$^+$.

Step 4: 4-{2-[(S)-1-(4-bromo-phenyl)-ethylamino]-ethyl}-adamantane-1,4-diol

The title compound is prepared from (2,5-dihydroxy-adamantan-2-yl)-acetaldehyde and (S)-1-(4-bromo-phenyl)-ethylamine following a procedure analogous to that described in Step 3 of Intermediate 2; the title compound is obtained as a mixture of 2 diastereomers. Yield: 20% of theory; Mass spectrum (ESI$^+$): m/z=394/396 (Br) [M+H]$^+$.

Intermediate 16

9-{2-[(S)-1-(4-Fluoro-phenyl)-ethylamino]-ethyl}-3,3-dimethyl-1,5-dioxa-spiro[5.5]undecan-9-ol

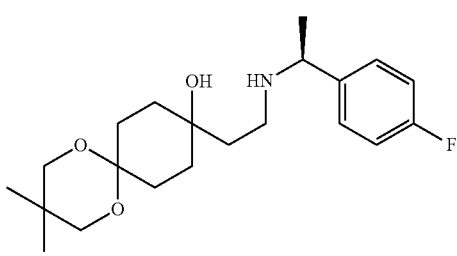 [SMILES: C[C@H](NCCC1(O)CCC2(CC1)OCC(C)(C)CO2)c1ccc(F)cc1]

The title compound is prepared from (9-hydroxy-3,3-dimethyl-1,5-dioxa-spiro[5.5]undec-9-yl)-acetaldehyde and (S)-1-(4-fluoro-phenyl)-ethylamine following a procedure analogous to that described in Step 3 of Intermediate 2. Yield: 74% of theory; Mass spectrum (ESI$^+$): m/z=366 [M+H]$^+$.

Intermediate 17

4-{2-[(S)-1-(4-Bromo-phenyl)-ethylamino]-ethyl}-4-hydroxy-cyclohexanecarboxylic acid ethyl ester

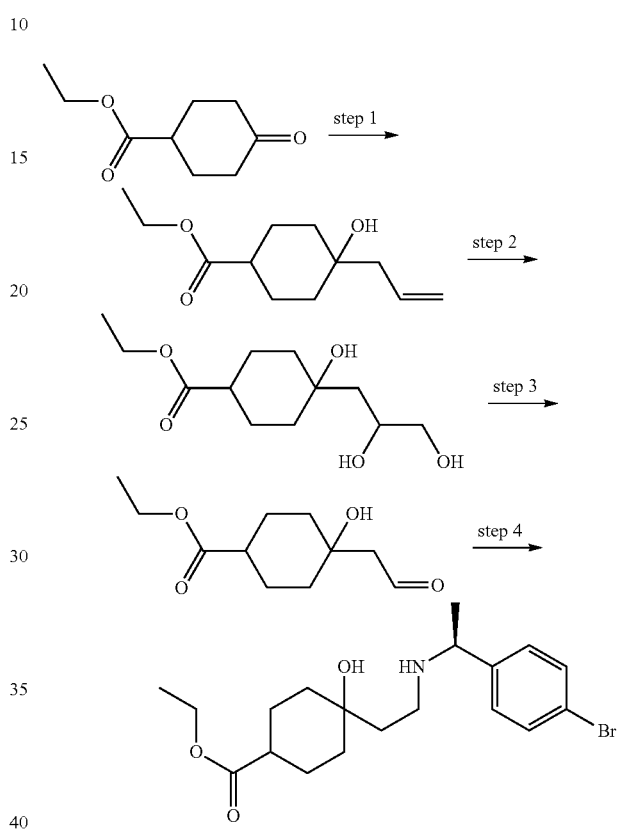

Step 1: 4-allyl-4-hydroxy-cyclohexanecarboxylic acid ethyl ester

The title compound is prepared from 4-oxo-cyclohexanecarboxylic acid ethyl ester and allyl bromide following a procedure analogous to that described in Step 1 of Intermediate 2. Yield: quantitative; Mass spectrum (ESI$^+$): m/z=213 [M+H]$^+$.

Step 2: 4-(2,3-dihydroxy-propyl)-4-hydroxy-cyclohexanecarboxylic acid ethyl ester The title compound is prepared from 4-allyl-4-hydroxy-cyclohexanecarboxylic acid ethyl ester following a procedure analogous to that described in Step 6 of Intermediate 2. Yield: 71% of theory; Mass spectrum (ESI$^+$): m/z=247 [M+H]$^+$.

Step 3: 4-hydroxy-4-(2-oxo-ethyl)-cyclohexanecarboxylic acid ethyl ester

The title compound is prepared from 4-(2,3-dihydroxy-propyl)-4-hydroxy-cyclohexanecarboxylic acid ethyl ester following a procedure analogous to that described in Step 7 of Intermediate 2; the title compound is directly submitted to the next reaction step. Yield: 52% of theory; Mass spectrum (ESI⁺): m/z=215 [M+H]⁺.

Step 4: 4-{2-[(S)-1-(4-bromo-phenyl)-ethylamino]-ethyl}-4-hydroxy-cyclohexanecarboxylic acid ethyl ester The title compound (a mixture of two diastereomers) is prepared from 4-hydroxy-4-(2-oxo-ethyl)-cyclohexanecarboxylic acid ethyl ester and (S)-1-(4-bromo-phenyl)-ethylamine following a procedure analogous to that described in Step 3 of Intermediate 2. Yield: 45% of theory; LC (method 5): $t_R$=1.04 min; Mass spectrum (ESI⁺): m/z=398/400 (Br) [M+H]⁺.

Intermediate 18

9-{2-[(S)-1-(4-Difluoromethoxy-phenyl)-ethylamino]-ethyl}-3,3-dimethyl-1,5-dioxa-spiro[5.5]undecan-9-ol

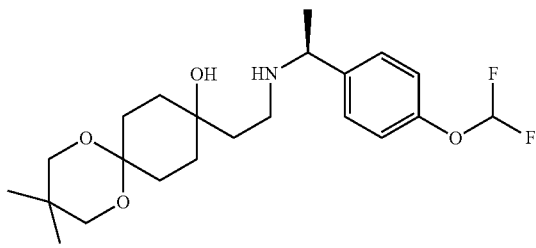 [SMILES: C[C@H](NCCC1(O)CCC2(CC1)OCC(C)(C)CO2)c1ccc(OC(F)F)cc1]

The title compound is prepared from (9-hydroxy-3,3-dimethyl-1,5-dioxa-spiro[5.5]undec-9-yl)-acetaldehyde and (S)-1-(4-difluoromethoxy-phenyl)-ethylamine following a procedure analogous to that described in Step 3 of Intermediate 2. Yield: 65% of theory; LC (method 5): $t_R$=1.02 min; Mass spectrum (ESI⁺): m/z=414 [M+H]⁺.

Intermediate 19

9-{2-[(S)-1-(2,5-Dimethyl-phenyl)-ethylamino]-ethyl}-3,3-dimethyl-1,5-dioxa-spiro[5.5]undecan-9-ol

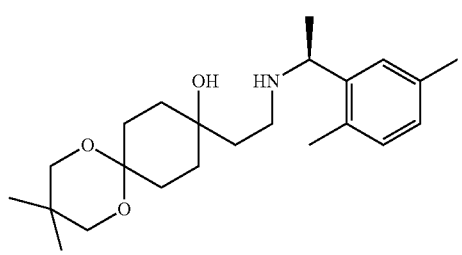

The title compound is prepared from (9-hydroxy-3,3-dimethyl-1,5-dioxa-spiro[5.5]undec-9-yl)-acetaldehyde and (S)-1-(2,5-dimethyl-phenyl)-ethylamine following a procedure analogous to that described in Step 3 of Intermediate 2. Yield: 77% of theory; LC (method 5): $t_R$=1.12 min; Mass spectrum (ESI⁺): m/z=376 [M+H]⁺.

Intermediate 20

3,3-Dimethyl-9-{2-[(S)-1-(4-trifluoromethoxy-phenyl)-ethylamino]-ethyl}-1,5-dioxa-spiro[5.5]undecan-9-ol

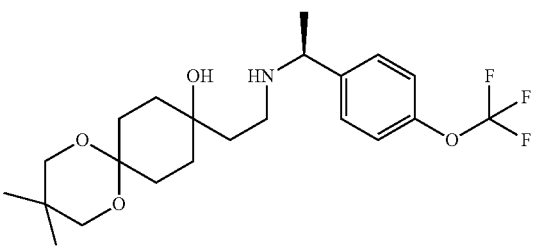 [SMILES: C[C@H](NCCC1(O)CCC2(CC1)OCC(C)(C)CO2)c1ccc(OC(F)(F)F)cc1]

The title compound is prepared from (9-hydroxy-3,3-dimethyl-1,5-dioxa-spiro[5.5]undec-9-yl)-acetaldehyde and (S)-1-(4-trifluoromethoxy-phenyl)-ethylamine following a procedure analogous to that described in Step 3 of Intermediate 2. Yield: 52% of theory; LC (method 5): $t_R$=1.13 min; Mass spectrum (ESI⁺): m/z=432 [M+H]⁺.

Intermediate 21

9-{2-[(S)-1-(4-Chloro-phenyl)-propylamino]-ethyl}-3,3-dimethyl-1,5-dioxa-spiro[5.5]undecan-9-ol The title compound is prepared from (9-hydroxy-3,3-dimethyl-1,5-dioxa-spiro[5.5]undec-9-yl)-acetaldehyde and (S)-1-(4-chloro-phenyl)-propylamine following a procedure analogous to that described in Step 3 of Intermediate 2. Yield: 60% of theory; LC (method 5): $t_R$=1.15 min; Mass spectrum (ESI⁺): m/z=396/398 (Cl) [M+H]⁺.

Intermediate 22

12-[(S)-1-(4-Bromo-phenyl)-ethyl]-3,3-dimethyl-1,5-dioxa-12-aza-dispiro[5.2.5.2]hexadecan-11-one -continued

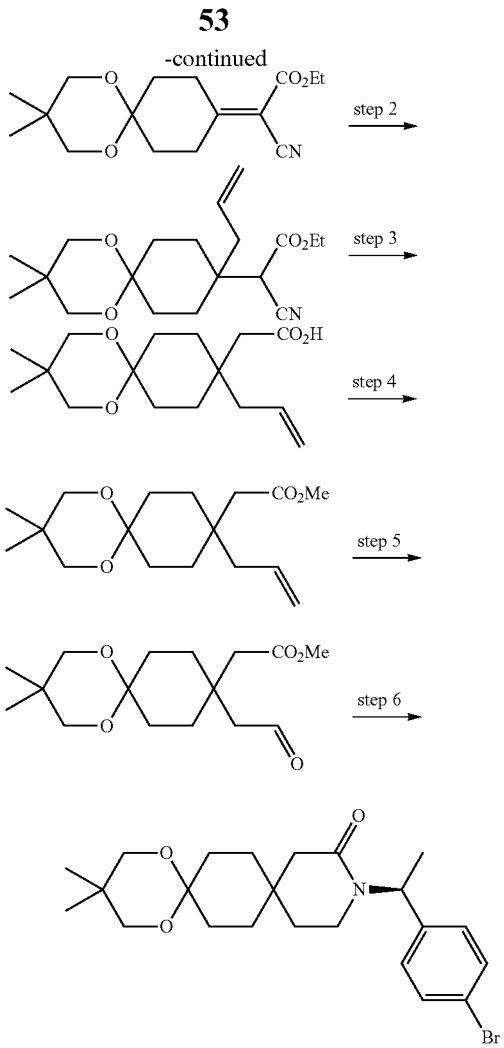

Step 1: cyano-(3,3-dimethyl-1,5-dioxa-spiro[5.5]
undec-9-ylidene)-acetic acid ethyl ester A mixture of 3,3-dimethyl-1,5-dioxa-spiro[5.5]undecan-9-one (10.0 g), ethyl cyanoacetate (5.9 mL), piperidine (0.5 mL), acetic acid (0.3 mL), and ethanol (100 mL) is stirred at room temperature overnight. The mixture is then cooled to −5° C. and the precipitate formed is separated by filtration, washed with ice-cold ethanol, and dried to give the title compound as a colorless solid. Yield: 13.7 g (93% of theory); Mass spectrum (ESI$^+$): m/z=294 [M+H]$^+$.

Step 2: 3-(9-allyl-3,3-dimethyl-1,5-dioxa-spiro[5.5]
undec-9-yl)-3-cyano-propionic acid ethyl ester Allylmagnesium chloride (2 mol/L in tetrahydrofuran, 56 ml) is added to a solution of cyano-(3,3-dimethyl-1,5-dioxa-spiro[5.5]undec-9-ylidene)-acetic acid ethyl ester (13.7 g) and CuI (2.7 g) in tetrahydrofuran (100 mL) under argon atmosphere and chilled in an ice bath. The mixture is warmed in the cooling bath to room temperature and stirred overnight. Aqueous NH$_4$Cl solution is then added and the resulting mixture is extracted with tert-butyl methyl ether. The combined extracts are washed with brine, dried (Na$_2$SO$_4$), and concentrated. The residue is chromatographed on silica gel (cyclohexane/ethyl acetate 1:02:3) to give the title compound. Yield: 5.0 g (31% of theory); Mass spectrum (ESI$^+$): m/z=336 [M+H]$^+$.

Step 3: (9-allyl-3,3-dimethyl-1,5-dioxa-spiro[5.5]
undec-9-yl)-acetic acid 3-(9-Allyl-3,3-dimethyl-1,5-dioxa-spiro[5.5]undec-9-yl)-3-cyano-propionic acid ethyl ester (4.21 g) is dissolved in a solution of KOH (16.5 g) in ethylene glycol (110 mL) and the resulting mixture is heated to 190° C. and stirred at this temperature for 3 h. After cooling to room temperature, the solution is diluted with water and neutralized with acetic acid. The resulting solution is extracted several times with ethyl acetate. The extracts are combined and the solvent is evaporated. The residue is chromatographed on silica gel (cyclohexane/ethyl acetate 1:0→1:1) to give the title compound. Yield: 3.54 g (quantitative); Mass spectrum (ESI$^+$): m/z=283 [M+H]$^+$.

Step 4: (9-allyl-3,3-dimethyl-1,5-dioxa-spiro[5.5]
undec-9-yl)-acetic acid methyl ester A mixture of (9-allyl-3,3-dimethyl-1,5-dioxa-spiro[5.5]undec-9-yl)-acetic acid (0.50 g), methyl iodide (0.12 mL), K$_2$CO$_3$ (0.37 g), and N,N-dimethylformamide (5 mL) is stirred at room temperature overnight. 10% aqueous K$_2$CO$_3$ solution is then added and the resulting mixture is extracted with ethyl acetate. The combined extract is washed with brine, dried (MgSO$_4$), and concentrated to give the crude title compound that is used without further purification. Yield: 0.36 g (crude); LC (method 6): t$_R$=1.65 min; Mass spectrum (ESI$^+$): m/z=297 [M+H]$^+$.

Step 5: [3,3-dimethyl-9-(2-oxo-ethyl)-1,5-dioxa-spiro[5.5]undec-9-yl]-acetic acid methyl ester The title compound is prepared from (9-allyl-3,3-dimethyl-1,5-dioxa-spiro[5.5]undec-9-yl)-acetic acid methyl ester following a procedure analogous to that described in Step 2 of Intermediate 2 and submitted directly to the next reaction step. Mass spectrum (ESI$^+$): m/z=299 [M+H]$^+$.

Step 6: 12-[(S)-1-(4-bromo-phenyl)-ethyl]-3,3-dimethyl-1,5-dioxa-12-aza-dispiro[5.2.5.2]hexadecan-11-one (S)-1-(4-Bromo-phenyl)-ethylamine (0.17 mL), sodium triacetoxyborohydride (0.25 g), and acetic acid (0.07 mL) are added in the given order to a solution of [3,3-dimethyl-9-(2-oxo-ethyl)-1,5-dioxa-spiro[5.5]undec-9-yl]acetic acid methyl ester (0.35 g) in tetrahydrofuran (5 mL) at room temperature. The resulting mixture is stirred at room temperature overnight. Water (5 mL) and 1 M aqueous NaOH solution (5 mL) are then added and the mixture is stirred for another 20 min. The mixture is extracted with tert-butyl methyl ether, and the combined extract is washed with water and brine. After drying (MgSO$_4$), the solvent is evaporated to give an oil that is treated with a mixture of water and ethanol to precipitate the title compound. Yield: 0.29 g (ca. 70% pure); Mass spectrum (ESI$^+$): m/z=450/452 (Br) [m+H]$^+$.

Intermediate 23

9-{2-[(S)-1-(4-tert-Butyl-phenyl)-ethylamino]-ethyl}-3,3-dimethyl-1,5-dioxa-spiro[5.5]undecan-9-ol

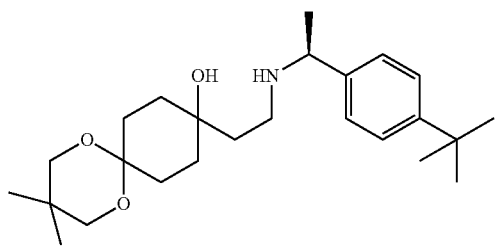 [SMILES: C[C@H](NCCC1(O)CCC2(CC1)OCC(C)(C)CO2)c1ccc(C(C)(C)C)cc1]

The title compound is prepared from (9-hydroxy-3,3-dimethyl-1,5-dioxa-spiro[5.5]undec-9-yl)-acetaldehyde and (S)-1-(4-tert-butyl-phenyl)-ethylamine following a procedure analogous to that described in Step 3 of Intermediate 2. Yield: 55% of theory; LC (method 5): $t_R$=1.22 min; Mass spectrum (ESI$^+$): m/z=404 [M+H]$^+$.

Intermediate 24

9-{2-[(S)-1-(2,4-Difluoro-phenyl)-ethylamino]-ethyl}-3,3-dimethyl-1,5-dioxa-spiro[5.5]undecan-9-ol

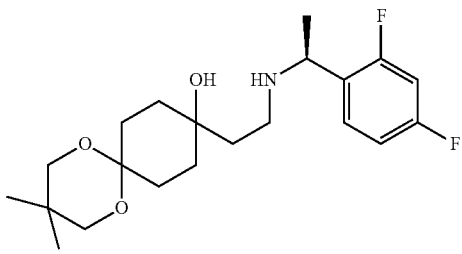 [SMILES: C[C@H](NCCC1(O)CCC2(CC1)OCC(C)(C)CO2)c1ccc(F)cc1F]

The title compound is prepared from (9-hydroxy-3,3-dimethyl-1,5-dioxa-spiro[5.5]undec-9-yl)-acetaldehyde and (S)-1-(2,4-difluoro-phenyl)-ethylamine following a procedure analogous to that described in Step 3 of Intermediate 2. Yield: 66% of theory; LC (method 5): $t_R$=0.99 min; Mass spectrum (ESI$^+$): m/z=384 [M+H]$^+$.

Intermediate 25

3-[(S)-1-(2,4-Difluoro-phenyl)-ethyl]-1-oxa-3-aza-spiro[5.5]undecane-2,9-dione

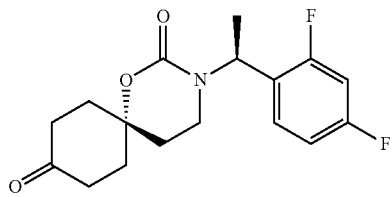

The title compound is prepared from 9-{2-[(S)-1-(2,4-difluoro-phenyl)-ethylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(2,4-difluoro-phenyl)-ethyl]-12,12-dimethyl-1,10,14-trioxa-3-aza-dispiro[5.2.5.2]hexadecan-2-one, obtained after that is treated as described in Step 10 of Intermediate 2 to convert the intermediate to the title compound as well. Yield: 30% of theory; LC (method 6): $t_R$=1.10 min; Mass spectrum (ESI$^+$): m/z=324 [M+H]$^+$.

Intermediate 26

9-{2-[(S)-1-(4-Methoxy-phenyl)-propylamino]-ethyl}-3,3-dimethyl-1,5-dioxa-spiro[5.5]undecan-9-ol

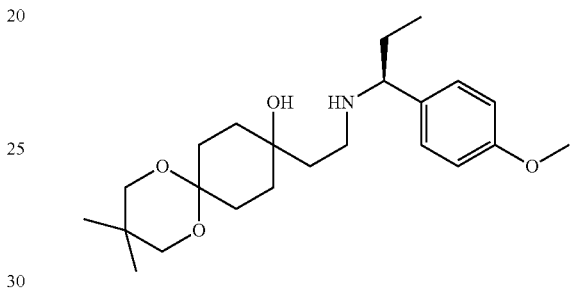

The title compound is prepared from (9-hydroxy-3,3-dimethyl-1,5-dioxa-spiro[5.5]undec-9-yl)-acetaldehyde and (S)-1-(4-methoxy-phenyl)-propylamine following a procedure analogous to that described in Step 3 of Intermediate 2. Yield: 53% of theory; LC (method 5): $t_R$=1.02 min; Mass spectrum (ESI$^+$): m/z=392 [M+H]$^+$.

Intermediate 27

9-{2-[1-(4-Bromo-phenyl)-1-methyl-ethylamino]-ethyl}-3,3-dimethyl-1,5-dioxa-spiro[5.5]undecan-9-ol

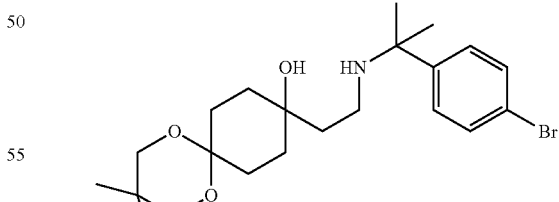

The title compound is prepared from (9-hydroxy-3,3-dimethyl-1,5-dioxa-spiro[5.5]undec-9-yl)-acetaldehyde and 1-(4-bromo-phenyl)-1-methyl-ethylamine following a procedure analogous to that described in Step 3 of Intermediate 2. Yield: 75% of theory; LC (method 5): $t_R$=1.12 min; Mass spectrum (ESI$^+$): m/z=440/442 (Br) [M+H]$^+$.

Intermediate 28

3-[1-(4-Bromo-phenyl)-1-methyl-ethyl]-1-oxa-3-aza-spiro[5.5]undecane-2,9-dione

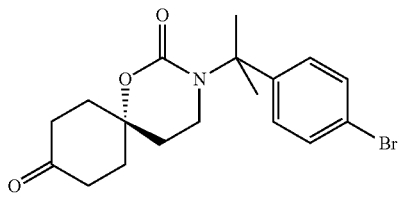

The title compound is prepared from 9-{2-[1-(4-bromo-phenyl)-1-methyl-ethylamino]-ethyl}-3,3-dimethyl-1,5-di-oxa-spiro[5.5]undecan-9-ol and triphosgene following a procedure analogous to that described in Step 4 of Intermediate 2; the crude product, a mixture of the title compound and 3-[1-(4-bromo-phenyl)-1-methyl-ethyl]-12,12-dimethyl-1,10,14-trioxa-3-aza-dispiro[5.2.5.2]hexadecan-2-one, obtained after that is treated as described in Step 10 of Intermediate 2 to convert the intermediate to the title compound as well. Yield: 37% of theory; LC (method 6): $t_R$=1.28 min; Mass spectrum (ESI$^+$): m/z=380/382 (Br) [m+H]$^+$.

Intermediate 29

3,3-Dimethyl-9-{2-[(S)-1-phenyl-ethylamino]-ethyl}-1,5-dioxa-spiro[5.5]undecan-9-ol

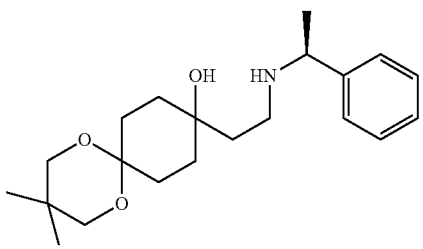 [SMILES: C[C@H](NCCC1(O)CCC2(CC1)OCC(C)(C)CO2)c1ccccc1]

The title compound is prepared from (9-hydroxy-3,3-dimethyl-1,5-dioxa-spiro[5.5]undec-9-yl)-acetaldehyde and (S)-1-phenyl-ethylamine following a procedure analogous to that described in Step 3 of Intermediate 2. Yield: 62% of theory; LC (method 6): $t_R$=1.10 min; Mass spectrum (ESI$^+$): m/z=348 [M+H]$^+$.

Intermediate 30

3,3-Dimethyl-9-{2-[(S)-1-naphthalen-2-yl-ethylamino]-ethyl}-1,5-dioxa-spiro[5.5]undecan-9-ol

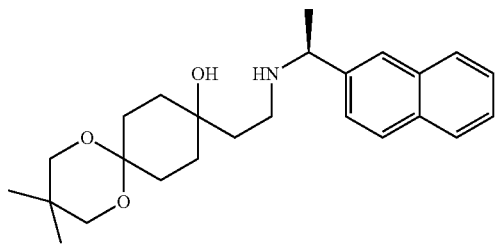 [SMILES: C[C@H](NCCC1(O)CCC2(CC1)OCC(C)(C)CO2)c1ccc2ccccc2c1]

The title compound is prepared from (9-hydroxy-3,3-dimethyl-1,5-dioxa-spiro[5.5]undec-9-yl)-acetaldehyde and (S)-1-naphthalen-2-yl-ethylamine following a procedure analogous to that described in Step 3 of Intermediate 2. Yield: 78% of theory; LC (method 6): $t_R$=1.27 min; Mass spectrum (ESI$^+$): m/z=398 [M+H]$^+$.

Intermediate 31

3,3-Dimethyl-9-{2-[4(S)-1-naphthalen-1-yl-ethylamino]-ethyl}-1,5-dioxa-spiro[5.5]undecan-9-ol

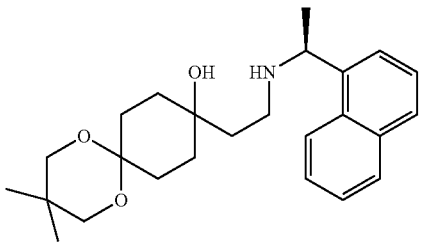 [SMILES: C[C@H](NCCC1(O)CCC2(CC1)OCC(C)(C)CO2)c1cccc2ccccc12]

The title compound is prepared from (9-hydroxy-3,3-dimethyl-1,5-dioxa-spiro[5.5]undec-9-yl)-acetaldehyde and (S)-1-naphthalen-1-yl-ethylamine following a procedure analogous to that described in Step 3 of Intermediate 2. Yield: 64% of theory; LC (method 6): $t_R$=1.27 min; Mass spectrum (ESI$^+$): m/z=398 [M+H]$^+$.

Intermediate 32

9-{2-[(S)-1-(3-Methoxy-phenyl)-ethylamino]-ethyl}-3,3-dimethyl-1,5-dioxa-spiro[5.5]undecan-9-ol

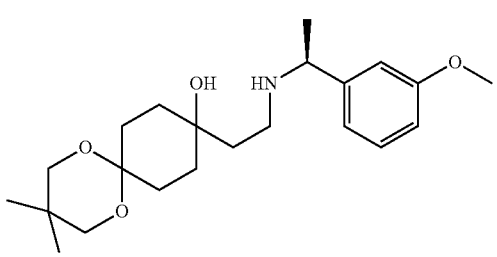

The title compound is prepared from (9-hydroxy-3,3-dimethyl-1,5-dioxa-spiro[5.5]undec-9-yl)-acetaldehyde and (S)-1-(3-methoxy-phenyl)-ethylamine following a procedure analogous to that described in Step 3 of Intermediate 2. Yield: 82% of theory; LC (method 6): $t_R$=1.12 min; Mass spectrum (ESI$^+$): m/z=378 [M+H]$^+$.

Intermediate 33

9-{2-[(S)-Indan-1-ylamino]-ethyl}-3,3-dimethyl-1,5-dioxa-spiro[5.5]undecan-9-ol

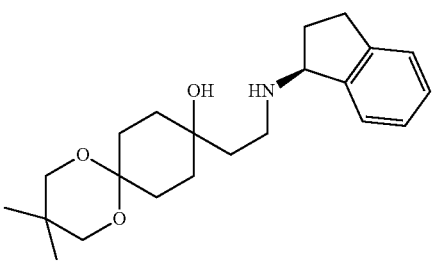 [SMILES: CC1(C)COC2(CCC(O)(CCN[C@H]3CCc4ccccc43)CC2)OC1]

The title compound is prepared from (9-hydroxy-3,3-dimethyl-1,5-dioxa-spiro[5.5]undec-9-yl)-acetaldehyde and (S)-indan-1-ylamine following a procedure analogous to that described in Step 3 of Intermediate 2. Yield: 26% of theory; LC (method 6): $t_R$=1.11 min; Mass spectrum (ESI$^+$): m/z=360 [M+H]$^+$.

Intermediate 34

3,3-Dimethyl-9-{2-[(S)-1-p-tolyl-propylamino]-ethyl}-1,5-dioxa-spiro[5.5]undecan-9-ol

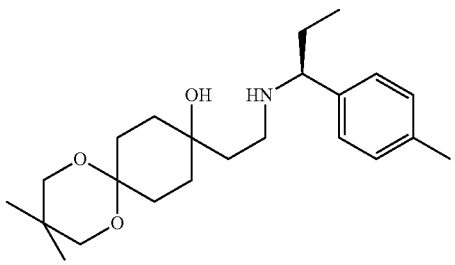

The title compound is prepared from (9-hydroxy-3,3-dimethyl-1,5-dioxa-spiro[5.5]undec-9-yl)-acetaldehyde and (S)-1-p-tolyl-propylamine following a procedure analogous to that described in Step 3 of Intermediate 2. Yield: 55% of theory; LC (method 5): $t_R$=1.10 min; Mass spectrum (ESI$^+$): m/z=376 [M+H]$^+$.

Intermediate 35

9-{2-[1-(4-Bromo-phenyl)-cyclopropylamino]-ethyl}-3,3-dimethyl-1,5-dioxa-spiro[5.5]undecan-9-ol

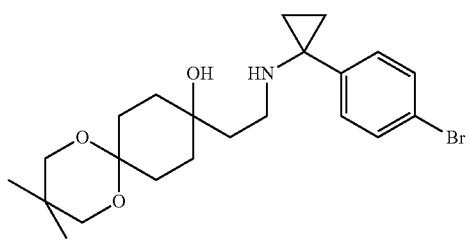 [SMILES: CC1(C)COC2(CCC(O)(CCNC3(c4ccc(Br)cc4)CC3)CC2)OC1]

The title compound is prepared from (9-hydroxy-3,3-dimethyl-1,5-dioxa-spiro[5.5]undec-9-yl)-acetaldehyde and 1-(4-bromo-phenyl)-cyclopropylamine following a procedure analogous to that described in Step 3 of Intermediate 2. Yield: 42% of theory; LC (method 5): $t_R$=1.12 min; Mass spectrum (ESI$^+$): m/z=438/440 (Br) [M+H]$^+$.

Intermediate 36

9-{2-[(S)-1-(4-Difluoromethyl-phenyl)-ethylamino]-ethyl}-3,3-dimethyl-1,5-dioxa-spiro[5.5]undecan-9-ol

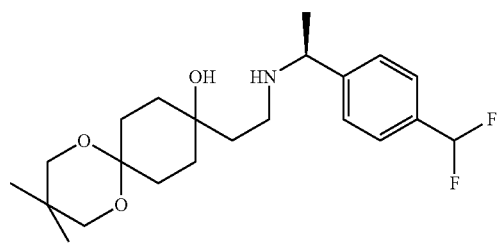 [SMILES: C[C@H](NCCC1(O)CCC2(CC1)OCC(C)(C)CO2)c1ccc(C(F)F)cc1]

The title compound is prepared from (9-hydroxy-3,3-dimethyl-1,5-dioxa-spiro[5.5]undec-9-yl)-acetaldehyde and (S)-1-(4-difluoromethyl-phenyl)-ethylamine following a procedure analogous to that described in Step 3 of Intermediate 2. Yield: 77% of theory; LC (method 8): $t_R$=1.10 min; Mass spectrum (ESI$^+$): m/z=398 [M+H]$^+$.

Intermediate 37

1-{2-[(S)-1-(4-Bromo-phenyl)-ethylamino]-ethyl}-cis-3-(tert-butyl-dimethyl-silanyloxy)-cyclohexanol

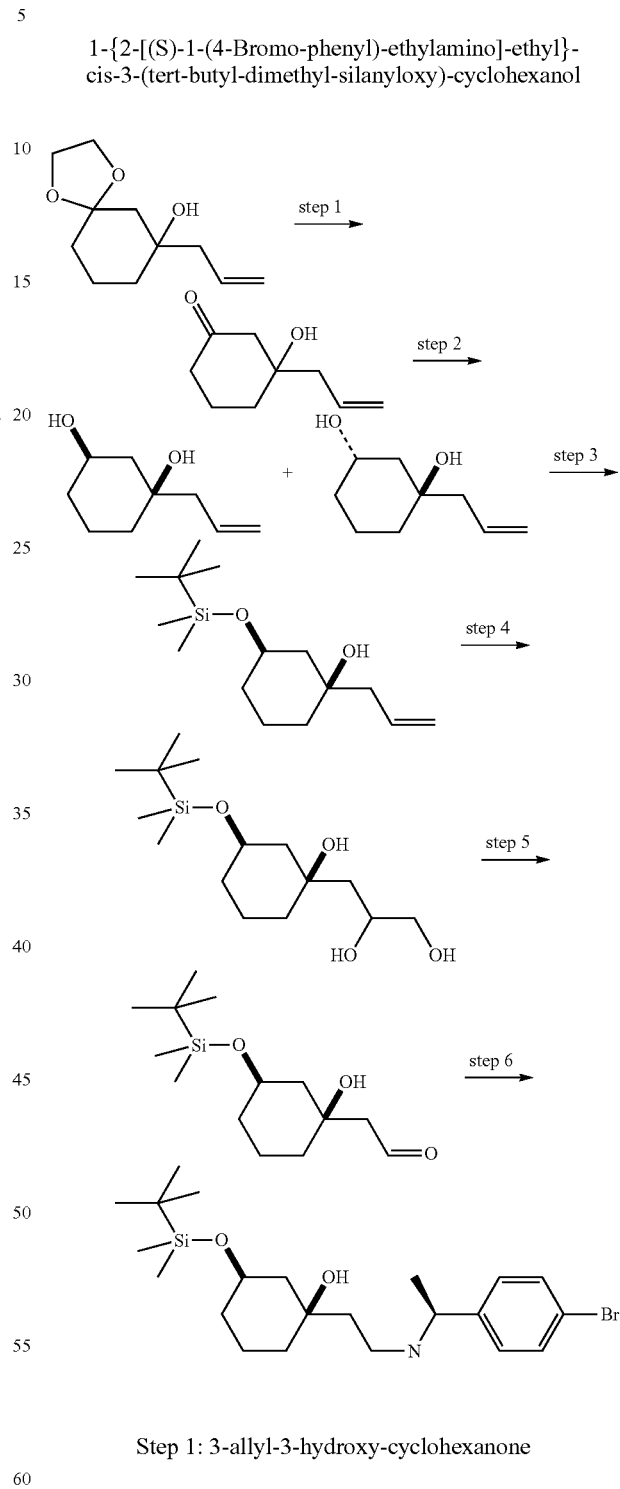

Step 1: 3-allyl-3-hydroxy-cyclohexanone

A mixture of 7-allyl-1,4-dioxa-spiro[4.5]decan-7-ol (12.8 g) and 0.5 M sulfuric acid (13 mL) is stirred at room temperature for 1 h. Water is then added and the resulting mixture is extracted with diethyl ether. The combined extract is washed with water (3×), brine, and dried (MgSO$_4$). The solvent is evaporated and the residue is triturated with diisopropyl ether/heptane 1:1 to give the title compound. Yield: 2.7 g (27% of theory); TLC [silicagel, cyclohexane/ethyl acetate 1:1]: $r_f$=0.55; Mass spectrum (ESI⁺): m/z=155 [M+H]⁺.

Step 2: 1-allyl-cyclohexane-cis-1,3-diol and 1-allyl-cyclohexane-trans-1,3-diol

Sodium borohydride (0.22 g) is added to a solution of 3-allyl-3-hydroxy-cyclohexanone (2.70 g) in methanol (30 mL) chilled in an ice bath. The mixture is warmed in the cooling bath to room temperature and stirred overnight. 1 M Hydrochloric acid (5 mL) is then added and the mixture is stirred for another 30 min. The mixture is concentrated and the residue is taken up in methanol. The resulting mixture is concentrated and the residue is chromatographed (cyclohexane/ethyl acetate 1:1→0:1) to give the two title compounds in separate fractions. 1-Allyl-cyclohexane-cis-1,3-diol: Yield: 0.85 g (31% of theory); Mass spectrum (ESI⁺): m/z=157 [m+H]⁺.

1-Allyl-cyclohexane-trans-1,3-diol: Yield: 1.80 g (66% of theory); Mass spectrum (ESI⁺): m/z=139 [M+H—H₂O]⁺.

Step 3: 1-allyl-cis-3-(tert-butyl-dimethyl-silanyloxy)-cyclohexanol

Imidazole (0.96 g) and tert-butyl-dimethylsilyl chloride (1.27 g) are added to a solution of 1-allyl-cyclohexane-cis-1,3-diol (1.10 g) in N,N-dimethylformamide (20 mL) at room temperature. The solution is stirred at room temperature overnight. Water is then added and the resulting solution is extracted with tert-butyl methyl ether. The combined extract is washed with water and brine and dried (MgSO₄). The solvent is evaporated to afford the title compound. Yield: 85% of theory; TLC [silicagel, cyclohexane/ethyl acetate 4:1]: $r_f$=0.60; Mass spectrum (ESI⁺): m/z=271 [M+H]⁺.

Step 4: 3-[cis-3-(tert-butyl-dimethyl-silanyloxy)-1-hydroxy-cyclohexyl]-propane-1,2-diol The title compound is prepared from 1-allyl-cis-3-(tert-butyl-dimethyl-silanyloxy)-cyclohexanol following a procedure analogous to that described in Step 6 of Intermediate 2. Yield: 80% of theory; Mass spectrum (ESI⁻): m/z=349 [M+HCOO]⁻.

Step 5: [cis-3-(tert-butyl-dimethyl-silanyloxy)-1-hydroxy-cyclohexyl]-acetaldehyde The title compound is prepared from 3-[cis-3-(tert-butyl-dimethyl-silanyloxy)-1-hydroxy-cyclohexyl]-propane-1,2-diol following a procedure analogous to that described in Step 7 of Intermediate 2; the product is directly submitted to the next reaction step. Yield: quantitative (crude).

Step 6: 1-{2-[(S)-1-(4-bromo-phenyl)-ethylamino]-ethyl}-cis-3-(tert-butyl-dimethyl-silanyloxy)-cyclohexanol The title compound is prepared from [cis-3-(tert-butyl-dimethyl-silanyloxy)-1-hydroxy-cyclohexyl]-acetaldehyde and (S)-1-(4-bromo-phenyl)-ethylamine following a procedure analogous to that described in Step 4 of Intermediate 2. Yield: quantitative; TLC [silicagel, CH₂Cl₂/(MeOH/NH₄OH 10:1) 9:1]: $r_f$=0.55.

Intermediate 38

1-{2-[(S)-1-(4-Bromo-phenyl)-ethylamino]-ethyl}-trans-3-(tert-butyl-dimethyl-silanyloxy)-cyclohexanol

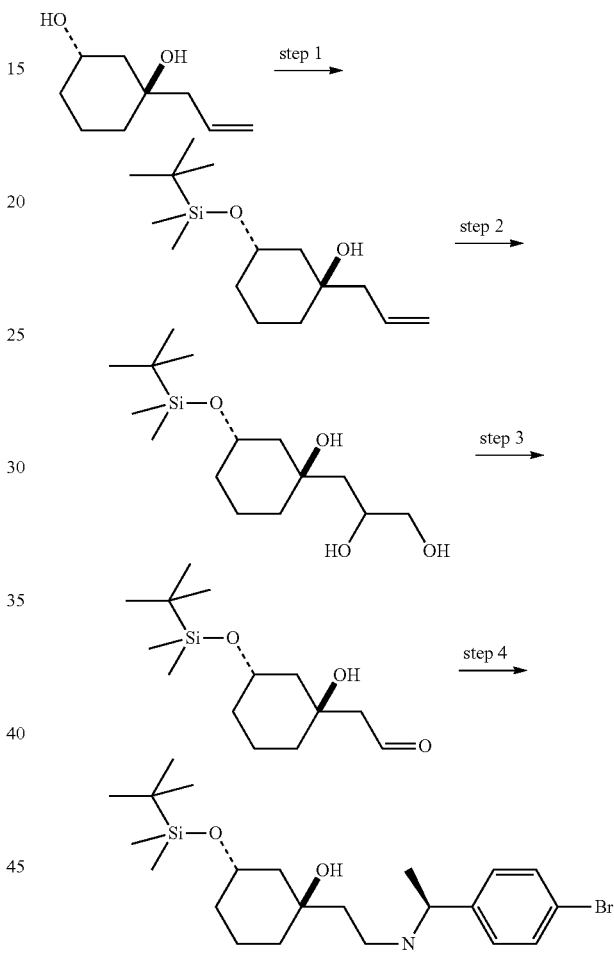

Step 1: 1-allyl-trans-3-(tert-butyl-dimethyl-silanyloxy)-cyclohexanol

The title compound is prepared from 1-allyl-cyclohexane-trans-1,3-diol following a procedure analogous to that described in Step 3 of Intermediate 37. Yield: quantitative; Mass spectrum (ESI⁺): m/z=271 [M+H]⁺.

Step 2: 3-[trans-3-(tert-butyl-dimethyl-silanyloxy)-1-hydroxy-cyclohexyl]-propane-1,2-diol The title compound is prepared from 1-allyl-trans-3-(tert-butyl-dimethyl-silanyloxy)-cyclohexanol following a procedure analogous to that described in Step 6 of Intermediate 2. Yield: 86% of theory; Mass spectrum (ESI⁺): m/z=305 [M+H]⁺.

Step 3: [trans-3-(tert-butyl-dimethyl-silanyloxy)-1-hydroxy-cyclohexyl]-acetaldehyde The title compound is prepared from 3-[trans-3-(tert-butyl-dimethyl-silanyloxy)-1-hydroxy-cyclohexyl]-propane-1,2-diol following a procedure analogous to that described in Step 7 of Intermediate 2; the product is directly submitted to the next reaction step. Yield: quantitative (crude).

Step 4: 1-{2-[(S)-1-(4-bromo-phenyl)-ethylamino]-ethyl}-trans-3-(tert-butyl-dimethyl-silanyloxy)-cyclohexanol The title compound is prepared from [trans-3-(tert-butyl-dimethyl-silanyloxy)-1-hydroxy-cyclohexyl]-acetaldehyde and (S)-1-(4-bromo-phenyl)-ethylamine following a procedure analogous to that described in Step 3 of Intermediate 2. Yield: quantitative; TLC [silicagel, $CH_2Cl_2$/(MeOH/$NH_4OH$ 10:1) 9:1]: $r_f$=0.50.

Intermediate 39

9-{2-[(S)-1-(2-Chloro-phenyl)-ethylamino]-ethyl}-3,3-dimethyl-1,5-dioxa-spiro[5.5]undecan-9-ol

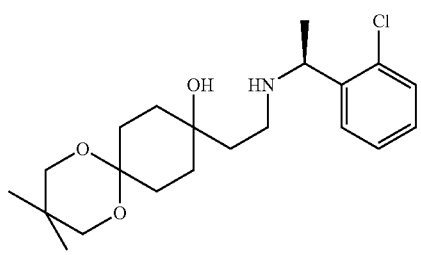 [SMILES: C[C@H](NCCC1(O)CCC2(CC1)OCC(C)(C)CO2)c1ccccc1Cl]

The title compound is prepared from (9-hydroxy-3,3-dimethyl-1,5-dioxa-spiro[5.5]undec-9-yl)-acetaldehyde and (S)-1-(2-chloro-phenyl)-ethylamine following a procedure analogous to that described in Step 3 of Intermediate 2. Yield: 89% of theory; LC (method 8): $t_R$=1.18 min; Mass spectrum (ESI$^+$): m/z=382/384 (Cl) [M+H]$^+$.

Intermediate 40

3,3-Dimethyl-9-{2-[(S)-1-phenyl-propylamino]-ethyl}-1,5-dioxa-spiro[5.5]undecan-9-ol

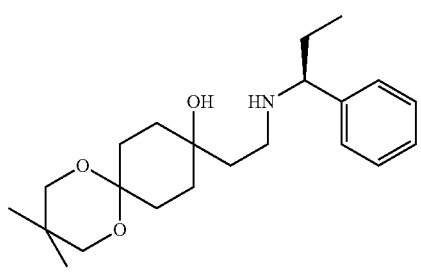 [SMILES: CC[C@H](NCCC1(O)CCC2(CC1)OCC(C)(C)CO2)c1ccccc1]

The title compound is prepared from (9-hydroxy-3,3-dimethyl-1,5-dioxa-spiro[5.5]undec-9-yl)-acetaldehyde and (S)-1-phenyl-propylamine following a procedure analogous to that described in Step 3 of Intermediate 2. Yield: 50% of theory; LC (method 8): $t_R$=1.16 min; Mass spectrum (ESI$^+$): m/z=362 [M+H]$^+$.

Intermediate 41

3,3-Dimethyl-9-{2-[(S)-1-o-tolyl-ethylamino]-ethyl}-1,5-dioxa-spiro[5.5]undecan-9-ol

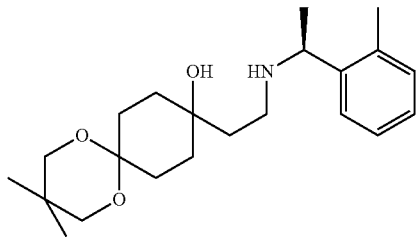 [SMILES: Cc1ccccc1[C@H](C)NCCC1(O)CCC2(CC1)OCC(C)(C)CO2]

The title compound is prepared from (9-hydroxy-3,3-dimethyl-1,5-dioxa-spiro[5.5]undec-9-yl)-acetaldehyde and (S)-1-o-tolyl-ethylamine following a procedure analogous to that described in Step 3 of Intermediate 2. Yield: 37% of theory; LC (method 8): $t_R$=1.16 min; Mass spectrum (ESI$^+$): m/z=362 [M+H]$^+$.

Intermediate 42

1-{2-[(S)-1-(4-Bromo-phenyl)-ethylamino]-ethyl}-trans-3-(tert-butyl-dimethyl-silanyloxy)-cyclohexanol

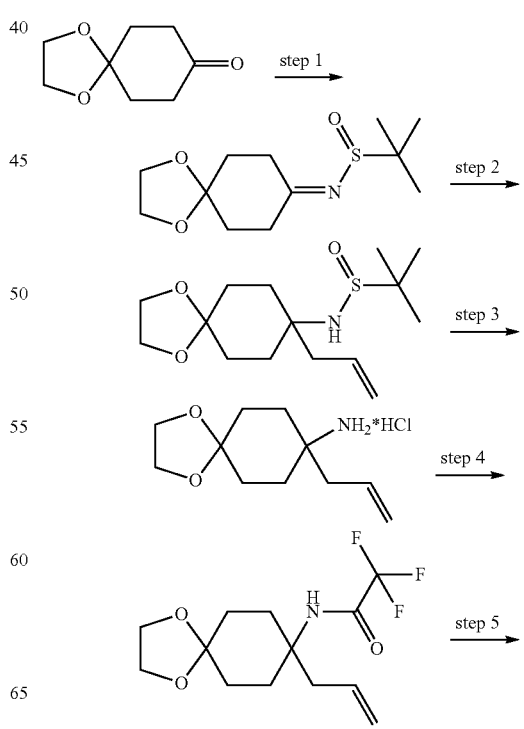

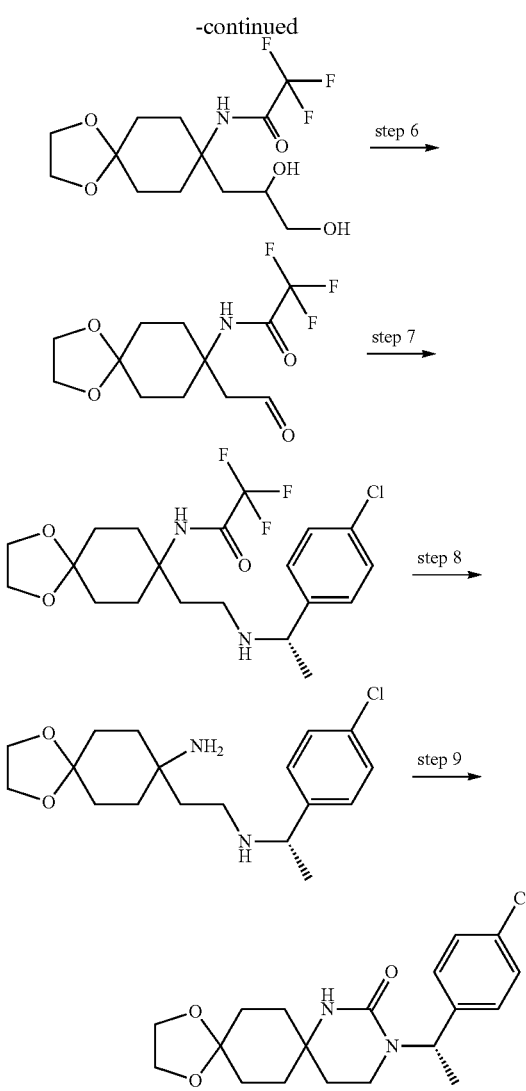

Step 1: 2-methyl-propane-2-sulfinic acid (1,4-dioxa-spiro[4.5]dec-8-ylidene)-amide 2-Methly-2-propanesulfinamide (7.4 g) is added to a solution of 1,4-dioxa-spiro[4.5]decan-8-one (10.0 g) and titanium tetraisopropoxide (37.9 mL) in tetrahydrofuran (130 mL) at room temperature. After stirring the solution at room temperature overnight, it is poured into a stirred saturated solution of NaHCO₃ in water. The resulting mixture is filtered over Celite and the remainder in the filter is thoroughly washed with ethyl acetate. The organic phase of the filtrate is separated, washed with brine, and dried (MgSO₄). The solvent is evaporated and the residue is chromatographed (cyclohexane/ethyl acetate 1:2→0:1) to give the title compound as a colorless solid. Yield: 7.0 g (42% of theory); TLC [silicagel, cyclohexane/ethyl acetate 1:2]: $r_f$=0.5; Mass spectrum (ESI⁺): m/z=260 [M+H]⁺.

Step 2: 2-methyl-propane-2-sulfinic acid (8-allyl-1, 4-dioxa-spiro[4.5]dec-8-yl)-amide Allylmagnesium chloride (2 mol/L in tetrahydrofuran, 17.0 mL) is added to a solution of 2-methyl-propane-2-sulfinic acid (1,4-dioxa-spiro[4.5]dec-8-ylidene)-amide (7.0 g) in tetrahydrofuran (70 mL) cooled to −78° C. The resulting solution is stirred with cooling for 3 h and then quenched by the addition of 10% aqueous NH₄Cl solution.

The resulting mixture is extracted with ethyl acetate, the combined extract is dried (MgSO₄), and the solvent is evaporated. The crude product is used without further purification. Yield: 8.5 g (crude); TLC [silicagel, cyclohexane/ethyl acetate 1:2]: $r_f$=0.2; Mass spectrum (ESI⁺): m/z=302 [M+H]⁺.

Step 3: 8-allyl-1,4-dioxa-spiro[4.5]dec-8-ylamine as hydrogenchloride salt

A solution of hydrochloric acid (2 mol/L in diethyl ether, 40 mL) and 2-methyl-propane-2-sulfinic acid (8-allyl-1,4-dioxa-spiro[4.5]dec-8-yl)-amide (8.5 g) in diethyl ether (80 mL) is stirred at room temperature for 30 min. The solvent is evaporated and the residue is triturated with diethyl ether to give the title compound as a solid. Yield: 3.5 g (impure); Mass spectrum (ESI⁺): m/z=198 [M+H]⁺.

Step 4: N-(8-allyl-1,4-dioxa-spiro[4.5]dec-8-yl)-2,2, 2-trifluoro-acetamide

Trifluoroacetic anhydride (2.5 mL) is added to an ice-cold solution of 8-allyl-1,4-dioxa-spiro[4.5]dec-8-ylamine (as hydrogenchloride salt, 3.50 g), triethylamine (4.5 mL), and 4-dimethylaminopyridine (catalytic amount) in dichloromethane (35 mL) at such a rate that the solution temperature maintained below 10° C. The solution is stirred at 10° C. for 1 h and at room temperature for another 2 h. Dichloromethane (100 ml) is added and the resulting solution is washed with saturated aqueous NaHCO₃ solution and brine and dried (MgSO₄). The solvent is evaporated and the residue is chromatographed (cyclohexane/ethyl acetate 4:1→1:4) to give the title compound as an oil. Yield: 2.00 g (46% of theory); LC (method 8): $t_R$=1.18 min; Mass spectrum (ESI⁺): m/z=294 [M+H]⁺.

Step 5: N-[8-(2,3-dihydroxy-propyl)-1,4-dioxa-spiro [4.5]dec-8-yl]-2,2,2-trifluoro-acetamide The title compound is prepared from N-(8-allyl-1,4-dioxa-spiro[4.5]dec-8-yl)-2,2,2-trifluoro-acetamide following a procedure analogous to that described in Step 6 of Intermediate 2. Yield: 99% of theory; LC (method 8): $t_R$=0.72 min; Mass spectrum (ESI⁺): m/z=328 [M+H]⁺.

Step 6: 2,2,2-trifluoro-N-[8-(2-oxo-ethyl)-1,4-dioxa-spiro[4.5]dec-8-yl]-acetamide The title compound is prepared from N-[8-(2,3-dihydroxy-propyl)-1,4-dioxa-spiro[4.5]dec-8-yl]-2,2,2-trifluoro-acetamide following a procedure analogous to that described in Step 7 of Intermediate 2. Yield: quantitative; LC (method 8): $t_R$=0.80 min; Mass spectrum (ESI⁺): m/z=296 [M+H]⁺.

Step 7: N-(8-{2-[(S)-1-(4-chloro-phenyl)-ethylamino]-ethyl}-1,4-dioxa-spiro[4.5]dec-8-yl)-2,2,2-trifluoro-acetamide The title compound is prepared from 2,2,2-trifluoro-N-[8-(2-oxo-ethyl)-1,4-dioxa-spiro[4.5]dec-8-yl]-acetamide and (S)-1-(4-chloro-phenyl)-ethylamine following a procedure analogous to that described in Step 3 of Intermediate 2. Yield: 75% of theory; LC (method 8): $t_R$=1.10 min; Mass spectrum (ESI⁺): m/z=435/437 (Cl) [M+H]⁺.

Step 8: 8-{2-[(S)-1-(4-chloro-phenyl)-ethylamino]-ethyl}-1,4-dioxa-spiro[4.5]dec-8-ylamine A mixture of 4 M aqueous NaOH solution (6 mL), N-(8-{2-[(S)-1-(4-chloro-phenyl)-ethylamino]-ethyl}-1,4-dioxaspiro[4.5]dec-8-yl)-2,2,2-trifluoro-acetamide (2.10 g), and methanol (10 mL) is stirred at 50° C. for 24 h. After cooling to room temperature, most of the methanol is evaporated and the residue is extracted with ethyl acetate. The combined extract is washed with brine, dried (MgSO$_4$), and concentrated to give the title compound. Yield: 98% of theory; LC (method 8): $t_R$=0.78 min; Mass spectrum (ESI$^+$): m/z=339/341 (Cl) [M+H]$^+$.

Step 9: 11-[(S)-1-(4-chloro-phenyl)-ethyl]-1,4-dioxa-9,11-diaza-dispiro[4.2.5.2]pentadecan-10-one The title compound is prepared from N-(8-{2-[(S)-1-(4-chloro-phenyl)-ethylamino]-ethyl}-1,4-dioxa-spiro[4.5]dec-8-yl)-2,2,2-trifluoro-acetamide and triphosgene following a procedure analogous to that described in Step 4 of Intermediate 2. Yield: quantitative (crude); Mass spectrum (ESI$^+$): m/z=365/367 (Cl) [M+H]$^+$.

Intermediate 43

9-{2-[(S)-1-(3,4-Difluoro-phenyl)-ethylamino]-ethyl}-3,3-dimethyl-1,5-dioxa-spiro[5.5]undecan-9-ol

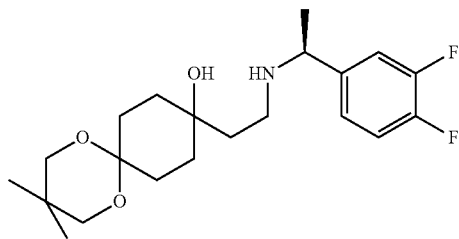 [SMILES: C[C@H](NCCC1(O)CCC2(CC1)OCC(C)(C)CO2)c1ccc(F)c(F)c1]

The title compound is prepared from (9-hydroxy-3,3-dimethyl-1,5-dioxa-spiro[5.5]undec-9-yl)-acetaldehyde and (S)-1-(3,4-difluoro-phenyl)-ethylamine following a procedure analogous to that described in Step 3 of Intermediate 2. Yield: 54% of theory; LC (method 5): $t_R$=1.00 min; Mass spectrum (ESI$^+$): m/z=384 [M+H]$^+$.

Intermediate 44

3,3-Dimethyl-9-{2-[(S)-1-(4-trifluoromethyl-phenyl)-ethylamino]-ethyl}-1,5-dioxa-spiro[5.5]undecan-9-ol

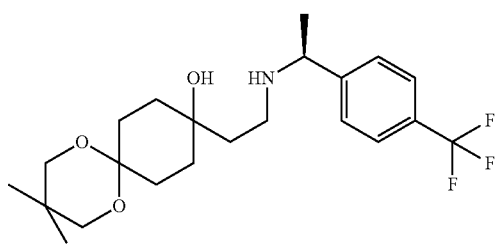 [SMILES: C[C@H](NCCC1(O)CCC2(CC1)OCC(C)(C)CO2)c1ccc(C(F)(F)F)cc1]

The title compound is prepared from (9-hydroxy-3,3-dimethyl-1,5-dioxa-spiro[5.5]undec-9-yl)-acetaldehyde and (S)-1-(4-trifluoro-phenyl)-ethylamine following a procedure analogous to that described in Step 3 of Intermediate 2. Yield: 64% of theory; LC (method 5): $t_R$=1.10 min; Mass spectrum (ESI$^+$): m/z=416 [M+H]$^+$.

Example 1

8-[(S)-1-(4-Bromo-phenyl)-ethyl]-6-oxa-8-aza-spiro[4.5]dec-2-en-7-one

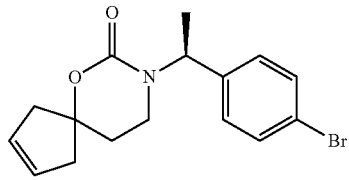 [SMILES: C[C@@H](c1ccc(Br)cc1)N1CCC2(CC=CC2)OC1=O]

(1,3-Bis(2,4,6-trimethylphenyl)-2-imidazolidinylidene)-dichloro-(phenylmethylene)-(tricyclohexylphosphine)-ruthenium (Grubbs' 2$^{nd}$ generation metathesis catalyst, 1.00 g) is added to a solution of (S)-6,6-diallyl-3-[1-(4-bromo-phenyl)-ethyl]-[1,3]oxazinan-2-one (8.65 g) in dichloromethane (120 mL) at room temperature. The resulting solution is stirred at room temperature overnight and then concentrated. The residue is chromatographed on silica gel (cyclohexane/ethyl acetate 3:2→0:1) to afford the title compound as a greyish solid. Yield: 6.11 g (77% of theory); LC (method 1): $t_R$=3.68 min; Mass spectrum (ESI$^+$): m/z=336/338 (Br) [M+H]$^+$.

Example 2

3-[(S)-1-(4-bromophenyl)ethyl]-cis-9-hydroxy-1-oxa-3-azaspiro[5.5]undecan-2-one

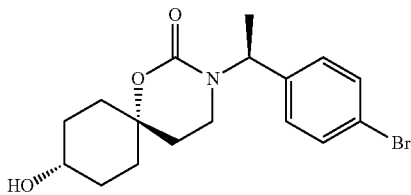

Sodium borohydride (47 mg) is added to 3-[(S)-1-(4-bromo-phenyl)-ethyl]-1-oxa-3-aza-spiro[5.5]undecane-2,9-dione (0.45 g) dissolved in tetrahydrofuran (4.5 mL) and water (0.6 mL) at room temperature. The mixture is stirred at room temperature for 2 h and then diluted with diethyl ether and acidified with 1 M aqueous hydrochloric acid. The organic phase is separated, washed with aqueous K$_2$CO$_3$ solution and brine, and dried (Na$_2$SO$_4$). The solvent is evaporated and the residue is submitted to HPLC on reversed phase (methanol/water) to give the title compound in a ca. 9:1 mixture with 3-[(S)-1-(4-bromophenyl)ethyl]-trans-9-hydroxy-1-oxa-3-azaspiro[5.5]undecan-2-one. Yield: 0.25 g (55% of theory); LC (method 1): $t_R$=3.42 min; Mass spectrum (ESI$^+$): m/z=368/370 (Br) [M+H]$^+$; $^1$H NMR (400 MHz, DMSO-d$_6$) δ 1.33-1.55 (m, 4H) superimposed on 1.47 (d, J=7.1 Hz, 3H), 1.55-1.87 (m, 6H), 2.66-2.76 (m, 1H), 3.13-

3.22 (m, 1H), 3.45 (m$_c$, 1H), 4.53 (d, J=4.5 Hz, 1H), 5.44 (q, J=7.1 Hz, 1H), 7.25 (d, J=8.4 Hz, 2H), 7.55 (d, J=8.4 Hz, 2H).

Examples 3, 4, 5, and 6

8-[(S)-1-(4-Bromo-phenyl)-ethyl]-2-hydroxy-6-oxa-8-aza-spiro[4.5]decan-7-one

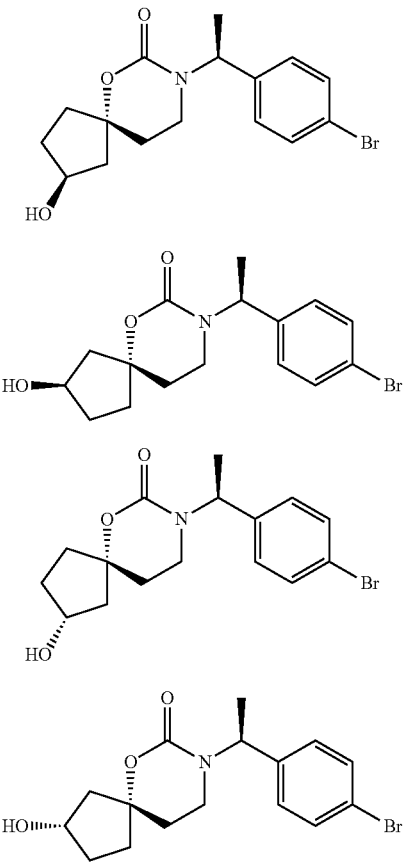

Borane dimethyl sulfide complex (2 mol/L in diethyl ether, 4.64 mL) is added dropwise to a solution of 8-[(S)-1-(4-bromo-phenyl)-ethyl]-6-oxa-8-aza-spiro[4.5]dec-2-en-7-one (2.60 g) in tetrahydrofuran (30 mL) chilled in an ice bath. The cooling bath is removed and the solution is stirred at room temperature overnight. The solution is then chilled again in an ice bath and 4 M aqueous NaOH solution (2.1 mL) is added followed by the dropwise addition of hydrogen peroxide (35% in water, 6 mL). The cooling bath is removed and the mixture is warmed to 40° C. and stirred at this temperature for 1 h. The mixture is diluted with water and extracted with diethyl ether. The combined extracts are washed with water, dried (Na$_2$SO$_4$), and concentrated. The residue is chromatographed on silica gel (methanol/ethyl acetate 0:1→4:1) to afford a mixture of the four title compounds which is submitted to SFC (Supercritical Fluid Chromatography) on chiral phase (column: phenomenex LUX 2A, 250×20 mm, 5 μM; eluent: isopropanol containing 0.2% diethylamine/sc carbon dioxide 25:75; flow: 60 mL/min) to give the four isomers in separate fractions.

(2S,5R)-8-[(1S)-1-(4-bromophenyl)ethyl]-2-hydroxy-6-oxa-8-azaspiro[4.5]decan-7-one (3):
Yield: 0.57 g (21% of theory); LC (method 1): t$_R$=2.54 min; Mass spectrum (ESI$^+$): m/z=354/356 (Br) [M+H]$^+$; $^1$H NMR (400 MHz, DMSO-d$_6$) δ 1.47 (d, J=7.2 Hz, 3H), 1.51-1.61 (m, 2H), 1.70-1.80 (m, 1H), 1.83-2.01 (m, 5H), 2.69-2.77 (m, 1H), 3.17-3.25 (m, 1H), 4.25 (m$_c$, 1H), 4.62 (d, J=3.6 Hz, 1H), 5.43 (q, J=7.1 Hz, 1H), 7.25 (dm, J=8.4 Hz, 2H), 7.55 (dm, J=8.4 Hz, 2H); assignment of the configurations is based on an X-ray structure.

(2R,5S)-8-[(1S)-1-(4-bromophenyl)ethyl]-2-hydroxy-6-oxa-8-azaspiro[4.5]decan-7-one (4): Yield: 0.61 g (22% of theory); Mass spectrum (ESI$^+$): m/z=354/356 (Br) [M+H]$^+$; $^1$H NMR (400 MHz, DMSO-d$_6$) δ 1.47 (d, J=7.3 Hz, 3H), ca. 1.49-1.57 (m, 1H), 1.60-1.71 (m, 2H), 1.78-1.98 (m, 4H), 2.04 (dd, J=14.0, 6.3 Hz, 1H), 2.76 (m$_c$, 1H), 3.14-3.22 (m, 1H), 4.26 (m$_c$, 1H), 4.65 (d, J=3.9 Hz, 1H), 5.43 (q, J=7.3 Hz, 1H), 7.25 (dm, J=8.3 Hz, 2H), 7.55 (dm, J=8.3 Hz, 2H).

(2R,5R)-8-[(1S)-1-(4-bromophenyl)ethyl]-2-hydroxy-6-oxa-8-azaspiro[4.5]decan-7-one (5): Yield: 0.18 g (6% of theory); Mass spectrum (ESI$^+$): m/z=354/356 (Br) [M+H]$^+$; $^1$H NMR (400 MHz, DMSO-d$_6$) δ 1.47 (d, J=7.1 Hz, 3H), 1.57-1.70 (m, 3H), 1.73-1.86 (m, 3H), 1.86-2.00 (m, 2H), 2.72 (m$_c$, 1H), 3.14-3.22 (m, 1H), 4.07 (m$_c$, 1H), 4.69 (d, J=4.4 Hz, 1H), 5.43 (q, J=7.1 Hz, 1H), 7.25 (dm, J=8.3 Hz, 2H), 7.55 (dm, J=8.5 Hz, 2H); position and spatial orientation of the hydroxyl group are arbitrarily chosen from possible isomers 5 and 6.

(2S,5S)-8-[(1S)-1-(4-bromophenyl)ethyl]-2-hydroxy-6-oxa-8-azaspiro[4.5]decan-7-one (6): Yield: 0.17 g (6% of theory); Mass spectrum (ESI$^+$): m/z=354/356 (Br) [M+H]$^+$; $^1$H NMR (400 MHz, DMSO-d$_6$) δ 1.47 (d, J=7.1 Hz, 3H), 1.50-1.71 (m, 3H), 1.71-1.89 (m, 4H), 2.05 (dd, J=14.2, 7.3 Hz, 1H), 2.73 (m$_c$, 1H), 3.13-3.22 (m, 1H), 4.09 (m$_c$, 1H), 4.69 (d, J=4.3 Hz, 1H), 5.43 (q, J=7.1 Hz, 1H), 7.25 (dm, J=8.3 Hz, 2H), 7.55 (dm, J=8.5 Hz, 2H); position and spatial orientation of the hydroxyl group are arbitrarily chosen from possible isomers 5 and 6.

Example 7

(2S,5R)-2-Hydroxy-8-{(S)-1-[4-(1-methyl-2-oxo-1,2-dihydro-pyridin-4-yl)-phenyl]-ethyl}-6-oxa-8-aza-spiro[4.5]decan-7-one

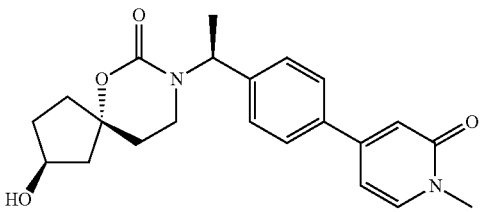 [SMILES: C[C@@H](c1ccc(-c2ccn(C)c(=O)c2)cc1)N1CC[C@@]2(CC[C@H](O)C2)OC1=O]

2 M aqueous Na$_2$CO$_3$ solution (0.37 mL) is added to a solution of (2S,5R)-2-hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one (150 mg) and 4-bromo-1-methyl-1H-pyridin-2-one (84 mg) in N,N-dimethylformamide (3 mL). The resulting mixture is sparged with argon for 5 min prior to the addition of [1,1'-bis(diphenylphosphino)ferrocene]dichloropalladium(11) dichloromethane complex (31 mg). The mixture is heated to 100° C. and stirred at this temperature overnight. After cooling to ambient temperature, water is added and the resulting mixture is extracted with ethyl acetate. The combined organic extracts are washed with brine, dried (MgSO$_4$), and concentrated. The residue is purified by HPLC on reversed phase (acetonitrile/water) to afford the title compound. Yield: 8 mg (6% of theory); LC (method 3): t$_R$=2.69 min; Mass spectrum (ESI$^+$): m/z=383 [M+H]$^+$.

Example 8

5-{(S)-4-[1-((2S,5R)-2-Hydroxy-7-oxo-6-oxa-8-aza-spiro[4.5]dec-8-yl)-ethyl]-phenyl}-pyridine-2-carboxylic acid dimethylamide

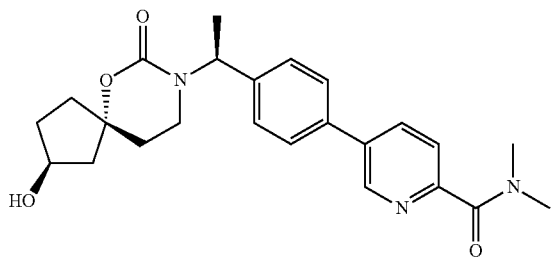 [SMILES: C[C@@H](c1ccc(-c2ccc(C(=O)N(C)C)nc2)cc1)N1CC[C@@]2(CC[C@H](O)C2)OC1=O]

The title compound is prepared from (2S,5R)-2-hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one and 5-bromo-pyridine-2-carboxylic acid dimethylamide following a procedure analogous to that described in Example 7. Yield: 11% of theory; LC (method 3): t$_R$=2.78 min; Mass spectrum (ESI$^+$): m/z=424 [M+H]$^+$.

Examples 9 and 10

(2R,5R)-2-Hydroxy-8-{(S)-1-[4-(1-methyl-2-oxo-1,2-dihydro-pyridin-4-yl)-phenyl]-ethyl}-6-oxa-8-aza-spiro[4.5]decan-7-one (9) and (2S,5S)-2-Hydroxy-8-{(S)-1-[4-(1-methyl-2-oxo-1,2-dihydro-pyridin-4-yl)-phenyl]-ethyl}-6-oxa-8-aza-spiro[4.5]decan-7-one (10)

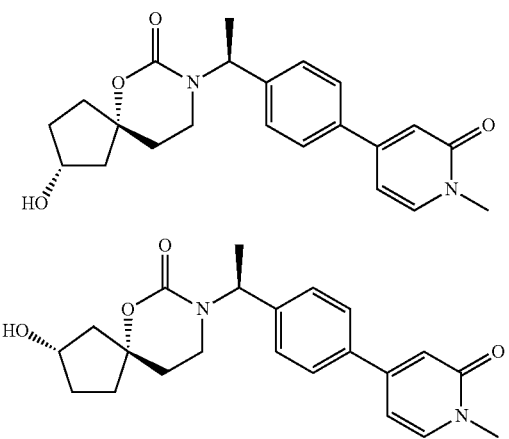

The title compounds are prepared from a mixture of (2R,5R)—, (2S,5S)—, and (2R,5S)-2-hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one (Intermediate 4, ca. 1:1:0.3) and 4-bromo-1-methyl-1H-pyridin-2-one following a procedure analogous to that described in Example 7. The mixture of the title compounds is submitted to HPLC on reversed phase (MeOH/water) to give two fractions containing mixtures of two isomers.

(2R,5R)-2-Hydroxy-8-{(S)-1-[4-(1-methyl-2-oxo-1,2-dihydro-pyridin-4-yl)-phenyl]-ethyl}-6-oxa-8-aza-spiro[4.5]decan-7-one (9, ca. 60:40 mixture of 2 isomers): Yield: 22% of theory; Mass spectrum (ESI$^+$): m/z=383 [M+H]$^+$; $^1$H NMR (400 MHz, DMSO-d$_6$) δ 1.52 (d, J=7.2 Hz, 3H) superimposed on ca. 1.48-2.09 (m, 8H), 2.75-2.86 (m, 1H), 3.17-3.26 (m, 1H), 3.45 (s, 3H), 4.23-4.31 (m, 1H), 4.63 (d, J=3.9 Hz, 0.6H), 4.65 (d, J=3.9 Hz, 0.4H), 5.46-5.54 (m, 1H), 6.57 (dd, J=7.1, 2.0 Hz, 1H), 6.67 (hardly resolved d, J=1.7 Hz, 1H), 7.39 (d, J=8.3 Hz, 2H), 7.72 (d, J=8.3 Hz, 2H), 7.76 (d, J=7.1 Hz, 1H). The configurations of the stereogenic centers of the spirooxazinone are arbitrarily assigned.

(2R,5S)-2-Hydroxy-8-{(S)-1-[4-(1-methyl-2-oxo-1,2-dihydro-pyridin-4-yl)-phenyl]-ethyl}-6-oxa-8-aza-spiro[4.5]decan-7-one (10, ca. 85:15 mixture of isomers): Yield: 7% of theory; Mass spectrum (ESI$^+$): m/z=383 [M+H]$^+$; $^1$H NMR (400 MHz, DMSO-d$_6$) δ 1.52 (d, J=7.13 Hz, 3H) superimposed on ca. 1.48-1.59 (m, 1H), 1.59-2.00 (m, 6H), 2.05 (dd, J=14.0, 6.3 Hz, 1H), 2.77-2.86 (m, 1H), 3.17-3.26 (m, 1H), 3.45 (s, 3H), 4.28 (m$_c$, 1H), 4.65 (d, J=3.9 Hz, 1H), 5.50 (q, J=7.1 Hz, 1H), 6.57 (dd, J=7.1, 1.9 Hz, 1H), 6.67 (hardly resolved d, J=1.7 Hz, 1H), 7.39 (d, J=8.1 Hz, 2H), 7.72 (d, J=8.3 Hz, 2H), 7.76 (d, J=7.1 Hz, 1H). The configurations of the stereogenic centers of the spirooxazinone are arbitrarily assigned.

Example 11

3-[(S)-1-(4-bromo-phenyl)-ethyl]-1-oxa-3-aza-spiro[5.5]undecane-2,9-dione

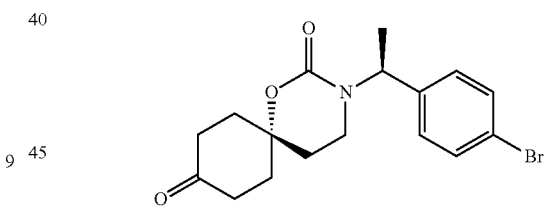

Triphosgene (2.51 g) is added to a solution of 9-{2-[(S)-1-(4-bromo-phenyl)-ethylamino]-ethyl}-3,3-dimethyl-1,5-dioxa-spiro[5.5]undecan-9-ol (4.00 g) and ethyl-diisopropylamine (1.7 mL) in dichloromethane (40 mL) chilled in an ice bath. The cooling bath is removed and the solution is stirred at room temperature overnight. Water is added and the organic phase is separated. The organic phase is dried (Na$_2$SO$_4$) and concentrated to give an oil that is dissolved in acetone (20 mL). 1 M Hydrochloric acid (19 mL) is added and the solution is stirred at room temperature for 3 h. The acetone is then evaporated, and the residue is diluted with saturated aqueous K$_2$CO$_3$ solution and extracted with ethyl acetate. The combined extracts are washed with water and brine, dried (MgSO$_4$), and concentrated. The residue is chromatographed on silica gel (cyclohexane/ethyl acetate 1:1→0:1) to give the title compound. Yield: 1.89 g (52% of theory); LC (method 8): t$_R$=1.27 min; Mass spectrum (ESI$^+$): m/z=366/368 (Br) [M+H]$^+$.

Example 12

2R,5S)-8-{(S)-1-[4-(1-Cyclopropyl-2-oxo-1,2-dihydro-pyridin-4-yl)-phenyl]-ethyl}-2-hydroxy-6-oxa-8-aza-spiro[4.5]decan-7-one

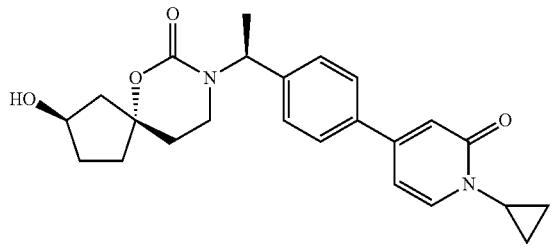 [SMILES: C[C@@H](c1ccc(-c2ccn(C3CC3)c(=O)c2)cc1)N1CC[C@]2(CC[C@@H](O)C2)OC1=O]

The title compound is prepared from (2R,5S)-2-hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one and 4-bromo-1-cyclopropyl-1H-pyridin-2-one following a procedure analogous to that described in Example 7. Yield: 37% of theory; LC (method 2): $t_R$=1.58 min; Mass spectrum (ESI⁺): m/z=409 [M+H]⁺.

Example 13

(2R,5S)-1-(5-{4-[(S)-1-(2-Hydroxy-7-oxo-6-oxa-8-aza-spiro[4.5]dec-8-yl)-ethyl]-phenyl}-pyridin-2-yl)-cyclopropanecarboxylic acid amide

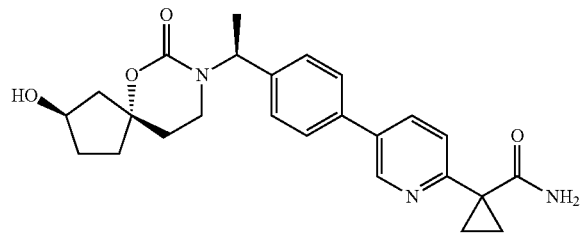 [SMILES: C[C@@H](c1ccc(-c2ccc(C3(C(N)=O)CC3)nc2)cc1)N1CC[C@]2(CC[C@@H](O)C2)OC1=O]

The title compound is prepared from (2R,5S)-2-hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one and 1-(5-bromo-pyridin-2-yl)-cyclopropanecarboxylic acid amide following a procedure analogous to that described in Example 7. Yield: 52% of theory; LC (method 2): $t_R$=1.60 min; Mass spectrum (ESI⁺): m/z=436 [M+H]⁺.

Example 14

2R,5S)-5-{4-[(S)-1-(2-Hydroxy-7-oxo-6-oxa-8-aza-spiro[4.5]dec-8-yl)-ethyl]-phenyl}-pyridine-2-carboxylic acid dimethylamide

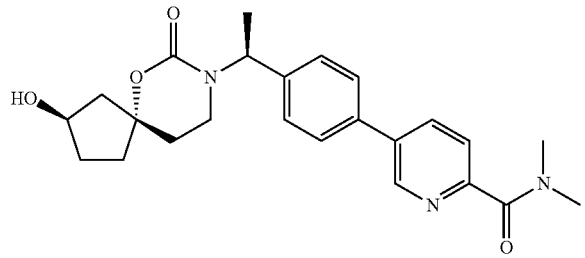 [SMILES: C[C@@H](c1ccc(-c2ccc(C(=O)N(C)C)nc2)cc1)N1CC[C@]2(CC[C@@H](O)C2)OC1=O]

The title compound is prepared from (2R,5S)-2-hydroxy-8-{(S)-1-[4-(4,4,5,5-tetramethyl-[1,3,2]dioxaborola-2-yl)-phenyl]-ethyl}-6-oxa-8-aza-spiro[4.5]decan-7-one and 5-bromo-pyridine-2-carboxylic acid dimethylamide following a procedure analogous to that described in Example 7. Yield: 36% of theory; LC (method 2): $t_R$=1.52 min; Mass spectrum (ESI⁺): m/z=424 [M+H]⁺.

Example 15

3-[(1S)-1-(4-bromophenyl)ethyl]-trans-9-hydroxy-1-oxa-3-azaspiro[5.5]undecan-2-one

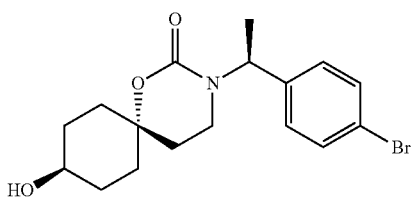 [SMILES: C[C@@H](c1ccc(Br)cc1)N1CC[C@]2(CC[C@@H](O)CC2)OC1=O]

1 M aqueous NaOH solution (1.2 mL) is added to trans-4-nitro-benzoic acid 3-[(S)-1-(4-bromo-phenyl)-ethyl]-2-oxo-1-oxa-3-aza-spiro[5.5]undec-9-yl ester (100 mg) suspended in methanol (2 mL) at room temperature. The mixture is stirred at room temperature for 4 h and then concentrated. The residue is purified by HPLC on reversed phase (methanol/water) to give the title compound. Yield: 60 mg (84% of theory); Mass spectrum (ESI⁺): m/z=368/370 (Br) [M+H]⁺; ¹H NMR (400 MHz, DMSO-d₆) δ 1.32-1.59 (m, 4H) superimposed on 1.47 (d, J=7.2 Hz, 3H), 1.62-1.79 (m, 5H), 1.83-1.91 (m, 1H), 2.68-2.76 (m, 1H), 3.15-3.23 (m, 1H), 3.69 (m_c, 1H), 4.46 (d, J=3.6 Hz, 1H), 5.43 (q, J=7.1 Hz, 1H), 7.25 (d, J=8.3 Hz, 2H), 7.55 (d, J=8.4 Hz, 2H).

Example 16

12,12-Dimethyl-3-{(S)-1-[4-(1-methyl-2-oxo-1,2-dihydro-pyridin-4-yl)-phenyl]-ethyl}-1,10,14-trioxa-3-aza-dispiro[5.2.5.2]hexadecan-2-one

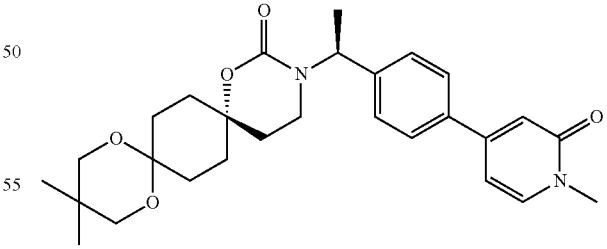

The title compound is prepared from 12,12-dimethyl-3-{(S)-1-[4-(4,4,5,5-tetramethyl-[1,3,2]dioxaborolan-2-yl)-phenyl]-ethyl}-1,10,14-trioxa-3-aza-dispiro[5.2.5.2]hexadecan-2-one and 4-bromo-1-methyl-1H-pyridin-2-one following a procedure analogous to that described in Example 7. Yield: 71% of theory; LC (method 3): $t_R$=3.40 min; Mass spectrum (ESI⁺): m/z=481 [M+H]⁺.

Example 17

5-{4-[(S)-1-(12,12-Dimethyl-2-oxo-1,10,14-trioxa-3-aza-dispiro[5.2.5.2]hexadec-3-yl)-ethyl]-phenyl}-pyridine-2-carboxylic acid dimethylamide

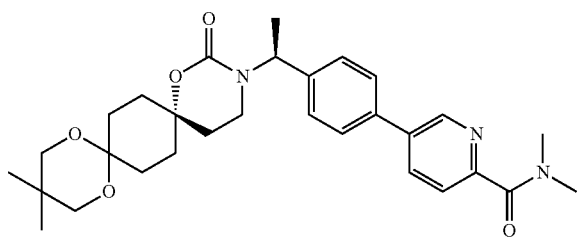

The title compound is prepared from 12,12-dimethyl-3-{(S)-1-[4-(4,4,5,5-tetramethyl-[1,3,2]dioxaborolan-2-yl)-phenyl]-ethyl}-1,10,14-trioxa-3-aza-dispiro[5.2.5.2]hexadecan-2-one and 5-bromo-pyridine-2-carboxylic acid dimethylamide following a procedure analogous to that described in Example 7. Yield: 76% of theory; LC (method 3): $t_R$=3.48 min; Mass spectrum (ESI$^+$): m/z=522 [M+H]$^+$.

Example 18

3-{(S)-1-[4-(1-Methyl-2-oxo-1,2-dihydro-pyridin-4-yl)-phenyl]-ethyl}-1-oxa-3-aza-spiro[5.5]undecane-2,9-dione

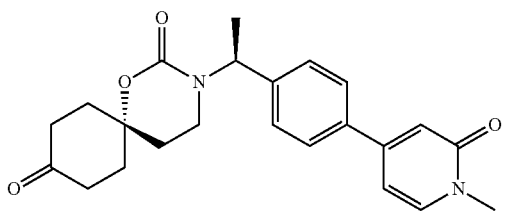

The title compound is prepared from 12,12-dimethyl-3-{(S)-1-[4-(1-methyl-2-oxo-1,2-dihydro-pyridin-4-yl)-phenyl]-ethyl}-1,10,14-trioxa-3-aza-dispiro[5.2.5.2]hexadecan-2-one following a procedure analogous to that described in Step 10 of Intermediate 2. Yield: 48% of theory; Mass spectrum (ESI$^+$): m/z=395 [M+H]$^+$; $^1$H NMR (400 MHz, DMSO-d$_6$) δ 1.55 (d, J=7.1 Hz, 3H), 1.85-2.05 (m, 5H), 2.08-2.27 (m, 3H), 2.44-2.56 (m, 2H) superimposed by DMSO-d$_5$, 2.81-2.89 (m, 1H), ca. 3.25-3.33 (m, 1H) superimposed by H$_2$O, 3.45 (s, 3H), 5.54 (q, J=7.1 Hz, 1H), 6.57 (dd, J=7.1, 2.0 Hz, 1H), 6.68 (d, J=2.0 Hz, 1H), 7.42 (dm, J=8.2 Hz, 2H), 7.72 (dm, J=8.2 Hz, 2H), 7.76 (d, J=7.1 Hz, 1H).

Example 19

5-{4-[(S)-1-(2,9-Dioxo-1-oxa-3-aza-spiro[5.5]undec-3-yl)-ethyl]-phenyl}-pyridine-2-carboxylic acid dimethylamide

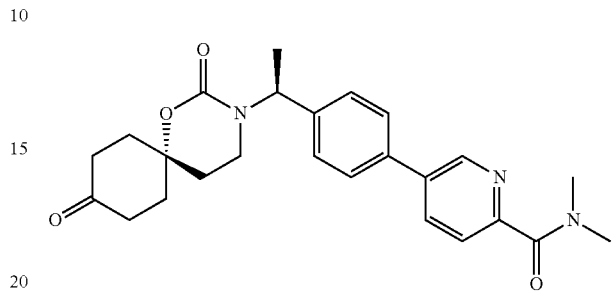

The title compound is prepared from 5-{4-[(S)-1-(12,12-dimethyl-2-oxo-1,10,14-trioxa-3-aza-dispiro[5.2.5.2]hexadec-3-yl)-ethyl]-phenyl}-pyridine-2-carboxylic acid dimethylamide following a procedure analogous to that described in Step 10 of Intermediate 2. Yield: 54% of theory; Mass spectrum (ESI$^+$): m/z=436 [M+H]$^+$; $^1$H NMR (400 MHz, DMSO-d$_6$) δ 1.57 (d, J=7.1 Hz, 3H), 1.85-2.05 (m, 5H), 2.09-2.28 (m, 3H), 2.45-2.57 (m, 2H) superimposed by DMSO-d$_5$, 2.83-2.91 (m, 1H), 3.01 (s, 3H), 3.03 (s, 3H), ca. 3.27-3.35 (m, 1H) superimposed by H$_2$O, 5.56 (q, J=7.1 Hz, 1H), 7.47 (dm, J=8.2 Hz, 2H), 7.65 (dm, J=8.2 Hz, 1H), 7.79 (dm, J=8.2 Hz, 2H), 8.20 (dd, J=8.2, 2.3 Hz, 1H), 8.91 (d, J=2.3 Hz, 1H).

Example 20 cis-9-Hydroxy-3-{(S)-1-[4-(1-methyl-2-oxo-1,2-dihydro-pyridin-4-yl)-phenyl]-ethyl}-1-oxa-3-aza-spiro[5.5]undecan-2-one

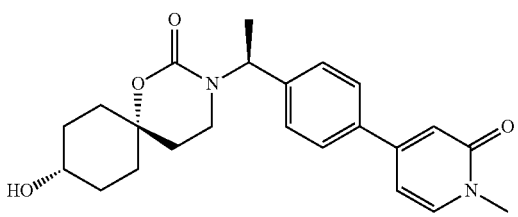 [SMILES: C[C@@H](c1ccc(-c2ccn(C)c(=O)c2)cc1)N1CC[C@]2(CC[C@H](O)CC2)OC1=O]

The title compound is prepared from 3-{(S)-1-[4-(1-methyl-2-oxo-1,2-dihydro-pyridin-4-yl)-phenyl]-ethyl}-1-oxa-3-aza-spiro[5.5]undecane-2,9-dione following a procedure analogous to that described in Example 2; after HPLC on reversed phase (methanol/water) the title compound is obtained in a ca. 4:1 mixture with cis-9-hydroxy-3-{(S)-1-[4-(1-methyl-2-oxo-1,2-dihydro-pyridin-4-yl)-phenyl]-ethyl}-1-oxa-3-aza-spiro[5.5]undecan-2-one. Yield: 63% of theory; LC (method 1): $t_R$=2.70 min; Mass spectrum (ESI$^+$): m/z=397 [M+H]$^+$.

Example 21 cis-5-{4-[1-(9-Hydroxy-2-oxo-1-oxa-3-aza-spiro[5.5]undec-3-yl)-ethyl]-phenyl}-pyridine-2-carboxylic acid dimethylamide

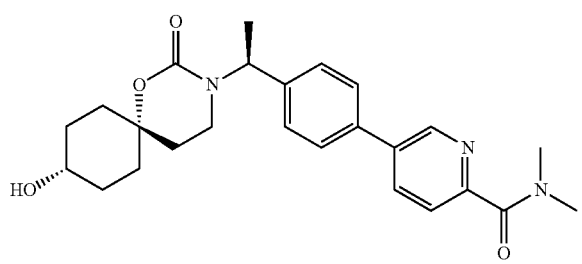

The title compound is prepared from 5-{4-[(S)-1-(2,9-dioxo-1-oxa-3-aza-spiro[5.5]undec-3-yl)-ethyl]-phenyl}-pyridine-2-carboxylic acid dimethylamide following a procedure analogous to that described in Example 2; after HPLC on reversed phase (methanol/water) the title compound is obtained in a ca. 4:1 mixture with cis-5-{4-[1-(9-hydroxy-2-oxo-1-oxa-3-aza-spiro[5.5]undec-3-yl)-ethyl]-phenyl}-pyridine-2-carboxylic acid dimethylamide. Yield: 77% of theory; LC (method 1): $t_R$=2.84 min; Mass spectrum (ESI$^+$): m/z=438 [M+H]$^+$.

Example 22

9-Hydroxy-3-{(S)-1-[4-(1-methyl-2-oxo-1,2-dihydro-pyridin-4-yl)-phenyl]-ethyl}-1-oxa-3-aza-spiro[5.5]undecan-2-one

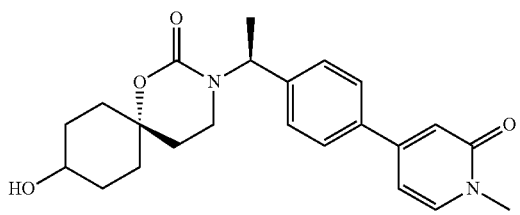

A mixture of 3-{(S)-1-[4-(1-methyl-2-oxo-1,2-dihydro-pyridin-4-yl)-phenyl]-ethyl}-1-oxa-3-aza-spiro[5.5]undecane-2,9-dione (130 mg), aluminum triisopropoxide (100 mg), and isopropanol (2 mL) is stirred at 140° C. for 1 h. After cooling to room temperature, the mixture is filtered and the filtrate is concentrated. The residue is purified by HPLC on reversed phase (methanol/water) to afford the title compound in a ca. 1:1 mixture of cis- and trans-isomer. Yield: 72% of theory; LC (method 2): $t_R$=1.49 and 1.51 min; Mass spectrum (ESI$^+$): m/z=397 [M+H]$^+$.

Example 23

5-{4-[1-(9-Hydroxy-2-oxo-1-oxa-3-aza-spiro[5.5]undec-3-yl)-ethyl]-phenyl}-pyridine-2-carboxylic acid dimethylamide

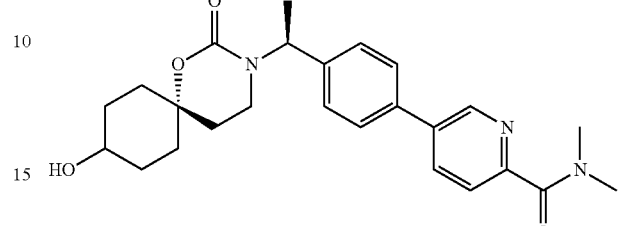

The title compound is prepared from 5-{4-[(S)-1-(2,9-dioxo-1-oxa-3-aza-spiro[5.5]undec-3-yl)-ethyl]-phenyl}-pyridine-2-carboxylic acid dimethylamide following a procedure analogous to that described in Example 22; after HPLC on reversed phase (methanol/water) the title compound is obtained in a ca. 1:1 mixture of cis- and trans-isomer. Yield: 53% of theory; LC (method 2): $t_R$=1.58 min; Mass spectrum (ESI$^+$): m/z=438 [M+H]$^+$.

Examples 24 and 25

(7R)-10-[(S)-1-(4-Bromophenyl)ethyl]-1,4,8-trioxa-10-azadispiro[4.1.5$^7$.3$^5$]pentadecan-9-one (24) and
(7S)-10-[(S)-1-(4-Bromophenyl)ethyl]-1,4,8-trioxa-10-azadispiro[4.1.5$^7$.3$^5$]pentadecan-9-one (25)

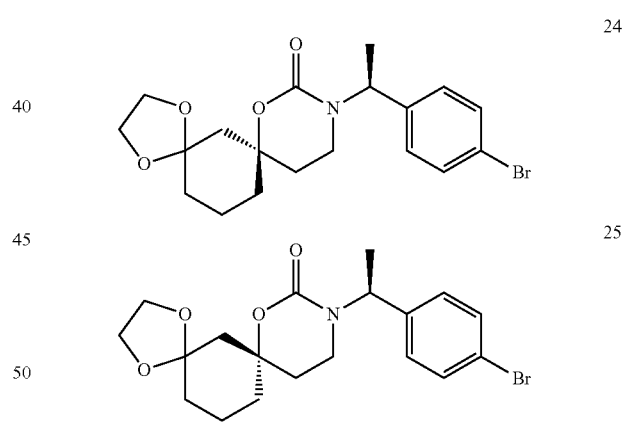

Sodium hydride (60% in mineral oil, 30 mg) is added to [(S)-1-(4-bromo-phenyl)-ethyl]-[2-(7-hydroxy-1,4-dioxa-spiro[4.5]dec-7-yl)-ethyl]-carbamic acid methyl ester (300 mg) dissolved in tetrahydrofuran (5 mL) at room temperature. The resulting mixture is stirred at room temperature for 20 min and at reflux temperature for 2 h. After cooling to room temperature, the mixture is diluted with water and methanol and then concentrated. The residue is submitted to HPLC on reversed phase (methanol/water) to give the two title compounds in separate fractions.

(7R)-10-[(S)-1-(4-Bromophenyl)ethyl]-1,4,8-trioxa-10-azadispiro[4.1.5$^7$.3$^5$]pentadecan-9-one (24): Yield: 120 mg (43% of theory); Mass spectrum (ESI$^+$): m/z=410/412 (Br) [M+H]$^+$.

(7S)-10-[(S)-1-(4-Bromophenyl)ethyl]-1,4,8-trioxa-10-azadispiro[4.1.5⁷.3⁵]pentadecan-9-one (25): Yield: 156 mg (56% of theory); Mass spectrum (ESI⁺): m/z=410/412 (Br) [m+H]⁺.

The structures of the two compounds have been confirmed by an X-ray structure.

Example 26

(7S)-10-[(S)-1-[4-(1-Methyl-2-oxo-1,2-dihydropyridin-4-yl)phenyl]ethyl]-1,4,8-trioxa-10-azadispiro[4.1.5⁷.3⁵]pentadecan-9-one

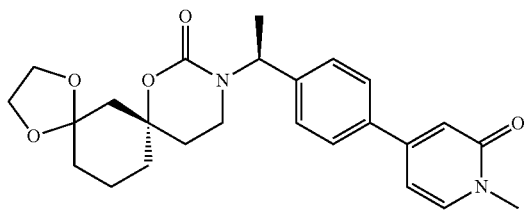 [SMILES: C[C@@H](c1ccc(-c2ccn(C)c(=O)c2)cc1)N1CC[C@]2(CCCC3(C2)OCCO3)OC1=O]

The title compound is prepared from (7S)-10-[(S)-1-[4-(4,4,5,5-tetramethyl-1,3,2-dioxaborolan-2-yl)phenyl]ethyl]-1,4,8-trioxa-10-azadispiro[4.1.5⁷.3⁵]pentadecan-9-one and 4-bromo-1-methyl-1H-pyridin-2-one following a procedure analogous to that described in Example 7. Yield: 92% of theory; LC (method 3): $t_R$=3.00 min; Mass spectrum (ESI⁺): m/z=439 [M+H]⁺.

Example 27

(7R)-10-[(S)-1-[4-(1-Methyl-2-oxo-1,2-dihydropyridin-4-yl)phenyl]ethyl]-1,4,8-trioxa-10-azadispiro[4.1.5⁷.3⁵]pentadecan-9-one

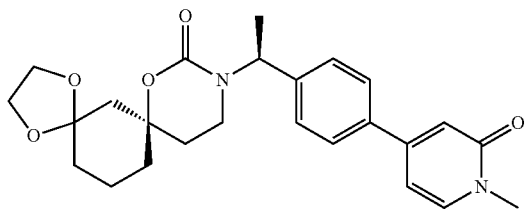 [SMILES: C[C@@H](c1ccc(-c2ccn(C)c(=O)c2)cc1)N1CC[C@@]2(CCCC3(C2)OCCO3)OC1=O]

The title compound is prepared from (7R)-10-[(S)-1-[4-(4,4,5,5-tetramethyl-1,3,2-dioxaborolan-2-yl)phenyl]ethyl]-1,4,8-trioxa-10-azadispiro[4.1.5⁷.3⁵]pentadecan-9-one and 4-bromo-1-methyl-1H-pyridin-2-one following a procedure analogous to that described in Example 7. Yield: 89% of theory; LC (method 3): $t_R$=3.04 min; Mass spectrum (ESI⁺): m/z=439 [M+H]⁺.

Example 28

(6R)-8-Hydroxy-3-[(S)-1-[4-(1-methyl-2-oxo-1,2-dihydropyridin-4-yl)phenyl]ethyl]-1-oxa-3-azaspiro[5.5]undecan-2-one

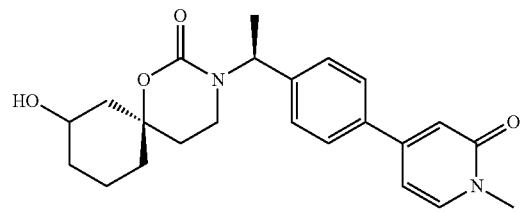

Ceric ammonium nitrate (0.23 g) dissolved in water (5 mL) is added in one portion to a solution of (7R)-10-[(S)-1-[4-(1-methyl-2-oxo-1,2-dihydropyridin-4-yl)phenyl]ethyl]-1,4,8-trioxa-10-azadispiro[4.1.5⁷.3⁵]pentadecan-9-one (75 mg) in acetonitrile (5 mL) stirred at 70° C. The resulting mixture is stirred at 70° C. for 10 min and then cooled to room temperature. Sodium borohydride (14 mg) is added and the mixture is stirred at room temperature overnight. Water is then added and the mixture is extracted with dichloromethane. The combined extracts are washed with water, dried (MgSO₄), and concentrated. The residue is submitted to HPLC on reversed phase (methanol/water) to give the title compound as an isomeric mixture (ca. 2:1). Yield: 10 mg (15% of theory); LC (method 2): $t_R$=1.55 min; Mass spectrum (ESI⁺): m/z=397 [M+H]⁺.

Example 29

(6S)-8-Hydroxy-3-[(S)-1-[4-(1-methyl-2-oxo-1,2-dihydropyridin-4-yl)phenyl]ethyl]-1-oxa-3-azaspiro[5.5]undecan-2-one

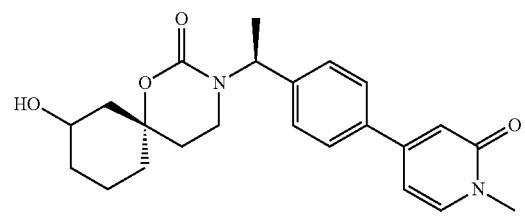

The title compound is prepared from (7S)-10-[(S)-1-[4-(1-methyl-2-oxo-1,2-dihydropyridin-4-yl)phenyl]ethyl]-1,4,8-trioxa-10-azadispiro[4.1.5⁷.3⁵]pentadecan-9-one following a procedure analogous to that described in Example 28; the title compound is obtained as an isomeric mixture (ca. 2:1). Yield: 29% of theory; LC (method 4): $t_R$=0.89 min; Mass spectrum (ESI⁺): m/z=397 [M+H]⁺.

Examples 30 and 31

(7S)-10-[(S)-1-(4-Methylphenyl)ethyl]-1,4,8-trioxa-10-azadispiro[4.1.5⁷.3⁵]pentadecan-9-one (30) and (7S)-10-[(S)-1-(4-Methoxyphenyl)ethyl]-1,4,8-trioxa-10-azadispiro[4.1.5⁷.3⁵]pentadecan-9-one (31)

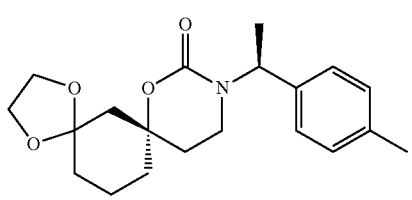

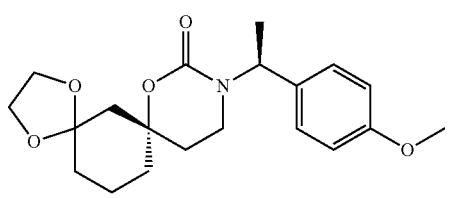

A flask charged with a stir bar, (7S)-10-[(S)-1-[4-(4,4,5,5-tetramethyl-1,3,2-dioxaborolan-2-yl)phenyl]ethyl]-1,4,8-trioxa-10-azadispiro[4.1.5⁷.3⁵]pentadecan-9-one (344 mg), 2 M aqueous $K_2CO_3$ solution (1.1 mL), toluene (10 mL), and ethanol (1.1 mL) is sparged with argon for 5 min. Methyl iodide (70 μL) and tetrakis(triphenylphosphine)palladium (0.35 g) are then added and the resulting mixture is heated to 80° C. After stirring at 80° C. for 18 h, the mixture is cooled to room temperature and extracted with tert-butyl methyl ether. The solvent is evaporated and the residue is submitted to HPLC on reversed phase (methanol/water) to afford the two title compounds in separate fractions.

(7S)-10-[(S)-1-(4-Methylphenyl)ethyl]-1,4,8-trioxa-10-azadispiro[4.1.5$^7$.3$^5$]pentadecan-9-one (30): Yield: 61 mg (23% of theory); Mass spectrum (ESI$^+$): m/z=346 [M+H]$^+$.

(7S)-10-[(S)-1-(4-Methoxyphenyl)ethyl]-1,4,8-trioxa-10-azadispiro[4.1.5$^7$.3$^6$]pentadecan-9-one (31): Yield: 67 mg (25% of theory); Mass spectrum (ESI$^+$): m/z=362 [M+H]$^+$.

Example 32

12,12-Dimethyl-3-[(S)-1-(4-methylphenyl)ethyl]-1,10,14-trioxa-3-azadispiro[5.2.5$^9$.2$^6$]hexadecan-2-one

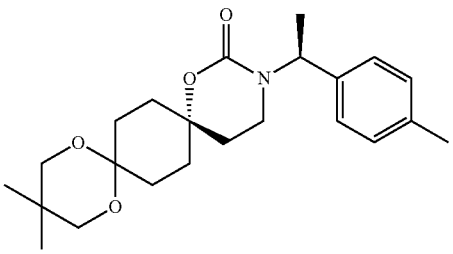

The title compound is prepared from 12,12-dimethyl-3-{(S)-1-[4-(4,4,5,5-tetramethyl-[1,3,2]dioxaborolan-2-yl)-phenyl]-ethyl}-1,10,14-trioxa-3-aza-dispiro[5.2.5.2]hexadecan-2-one and methyl iodide following a procedure analogous to that described in Example 30. Yield: 18% of theory; LC (method 4): $t_R$=1.16 min; Mass spectrum (ESI$^+$): m/z=388 [M+H]$^+$.

Example 33

3-[1-(S)-(4-Methylphenyl)-ethyl]-1-oxa-3-aza-spiro[5.5]undecane-2,9-dione

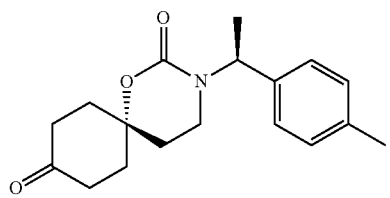

The title compound is prepared from 12,12-dimethyl-3-[(S)-1-(4-methylphenyl)ethyl]-1,10,14-trioxa-3-azadispiro[5.2.5$^9$.2$^6$]hexadecan-2-one following a procedure analogous to that described in Step 10 of Intermediate 2. Yield: 44% of theory; LC (method 4): $t_R$=1.52 min; Mass spectrum (ESI$^+$): m/z=302 [M+H]$^+$.

Example 34

3-[(S)-1-(4-Methoxy-phenyl)-ethyl]-1-oxa-3-aza-spiro[5.5]undecane-2,9-dione

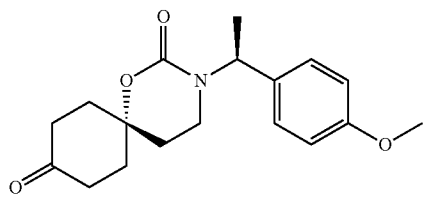

The title compound is prepared from 9-{2-[(S)-1-(4-methoxy-phenyl)-ethylamino]-ethyl}-3,3-dimethyl-1,5-dioxa-spiro[5.5]undecan-9-ol and triphosgene following a procedure analogous to that described in Step 4 of Intermediate 2; besides the title compound the intermediate 3-[(S)-1-(4-methoxy-phenyl)-ethyl]-12,12-dimethyl-1,10,14-trioxa-3-aza-dispiro[5.2.5.2]hexadecan-2-one (27% of theory) is also isolated. Yield: 38% of theory; LC (method 4): $t_R$=1.41 min; Mass spectrum (ESI$^+$): m/z=318 [m+H]$^+$.

Example 35

3-[(S)-1-(4-Chloro-phenyl)-ethyl]-1-oxa-3-aza-spiro[5.5]undecane-2,9-dione

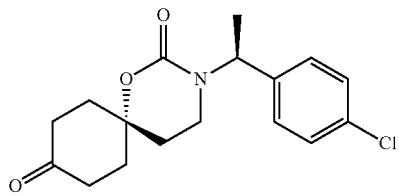

The title compound is prepared from 9-{2-[(S)-1-(4-chloro-phenyl)-ethylamino]-ethyl}-3,3-dimethyl-1,5-dioxa-spiro[5.5]undecan-9-ol and triphosgene following a procedure analogous to that described in Step 4 of Intermediate 2; besides the title compound the intermediate 3-[(S)-1-(4-chloro-phenyl)-ethyl]-12,12-dimethyl-1,10,14-trioxa-3-aza-dispiro[5.2.5.2]hexadecan-2-one (35% of theory) is also isolated. Yield: 23% of theory; LC (method 4): $t_R$=1.51 min; Mass spectrum (ESI$^+$): m/z=322/324 (Cl) [M+H]$^+$.

Example 36

4-[(S)-1-(2,9-Dioxo-1-oxa-3-aza-spiro[5.5]undec-3-yl)-ethyl]-benzonitrile

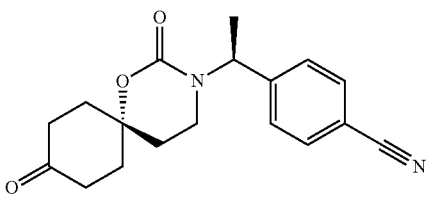

The title compound is prepared from 4-[(S)-1-(12,12-dimethyl-2-oxo-1,10,14-trioxa-3-aza-dispiro[5.2.5.2]hexadec-3-yl)-ethyl]-benzonitrile following a procedure analogous to that described in Step 10 of Intermediate 2. Yield: 61% of theory; LC (method 4): $t_R$=0.81 min; Mass spectrum (ESI$^+$): m/z=313 [M+H]$^+$.

Example 37

3-[(S)-(4-Bromo-phenyl)-cyclopropyl-methyl]-1-oxa-3-aza-spiro[5.5]undecane-2,9-dione

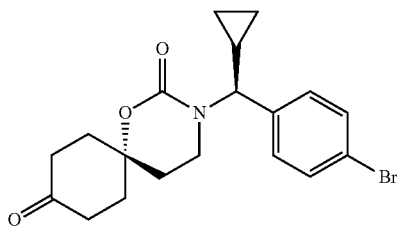

The title compound is prepared from 9-(2-{[(S)-(4-bromo-phenyl)-cyclopropyl-methyl]-amino}-ethyl)-3,3-dimethyl-1,5-dioxa-spiro[5.5]undecan-9-ol and triphosgene following a procedure analogous to that described in Step 4 of Intermediate 2; besides the title compound the intermediate 3-[(S)-(4-bromo-phenyl)-cyclopropyl-methyl]-12,12-dimethyl-1,10,14-trioxa-3-aza-dispiro[5.2.5.2]hexadecan-2-one (37% of theory) is also isolated. Yield: 25% of theory; LC (method 4): $t_R$=1.59 min; Mass spectrum (ESI$^+$): m/z=392/394 (Br) [M+H]$^+$.

Examples 38 and 39

5'-[(S)-1-(4-Bromophenyl)ethyl]-cis-5-hydroxyspiro[adamantane-2,2'-[1,5]oxazinane]-6'-one (38) and 5'-[(S)-1-(4-Bromophenyl)ethyl]-trans-5-hydroxyspiro[adamantane-2,2'-[1,5]oxazinane]-6'-one (39)

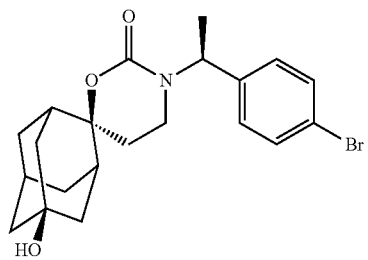

38

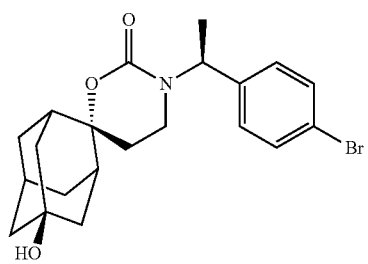

39

The title compounds are prepared from 4-{2-[(S)-1-(4-bromo-phenyl)-ethylamino]-ethyl}-adamantane-1,4-diol and triphosgene following a procedure analogous to that described in Step 4 of Intermediate 2 and separated by HPLC on reversed phase (methanol/water).

5'-[(S)-1-(4-Bromophenyl)ethyl]-cis-5-hydroxyspiro[adamantane-2,2'-[1,5]oxazinane]-6'-one (38): Yield: 53% of theory; LC (method 4): $t_R$=1.28 min; Mass spectrum (ESI$^+$): m/z=420/422 (Br) [M+H]$^+$.

5'-[(S)-1-(4-Bromophenyl)ethyl]-trans-5-hydroxyspiro[adamantane-2,2'-[1,5]oxazinane]-6'-one (39): Yield: 19% of theory; LC (method 4): $t_R$=1.41 min; Mass spectrum (ESI$^+$): m/z=420/422 (Br) [M+H]$^+$.

Examples 40 and 41 trans-9-Hydroxy-3-[(S)-1-(4-methoxy-phenyl)-ethyl]-1-oxa-3-aza-spiro[5.5]undecan-2-one (40) and cis-9-Hydroxy-3-[(S)-1-(4-methoxy-phenyl)-ethyl]-1-oxa-3-aza-spiro[5.5]undecan-2-one (41)

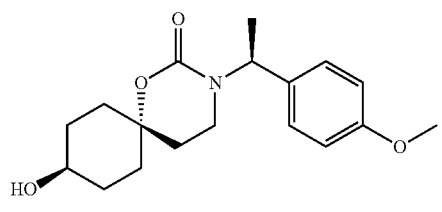

40

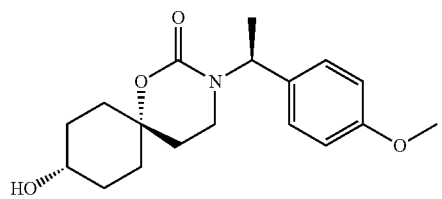

41

The title compounds are prepared from 3-[(S)-1-(4-methoxy-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

trans-9-Hydroxy-3-[(S)-1-(4-methoxy-phenyl)-ethyl]-1-oxa-3-aza-spiro[5.5]undecan-2-one (40): Yield: 26% of theory; Mass spectrum (ESI$^+$): m/z=320 [M+H]$^+$; $^1$H NMR (400 MHz, DMSO-d$_6$) δ 1.31-1.58 (m, 4H) superimposed by 1.44 (d, J=7.1 Hz, 3H), 1.58-1.78 (m, 5H), 1.79-1.88 (m, 1H), 2.61-2.70 (m, 1H), 3.09-3.18 (m, 1H), 3.69 (m$_c$, 1H), 3.74 (s, 3H), 4.46 (d, J=3.4 Hz, 1H), 5.46 (q, J=7.1 Hz, 1H), 6.91 (dm, J=8.7 Hz, 2H), 7.21 (dm, J=8.6 Hz, 2H).

cis-9-Hydroxy-3-[(S)-1-(4-methoxy-phenyl)-ethyl]-1-oxa-3-aza-spiro[5.5]undecan-2-one (41): Yield: 26% of theory; Mass spectrum (ESI$^+$): m/z=320 [M+H]$^+$; $^1$H NMR (400 MHz, DMSO-d$_6$) δ 1.30-1.53 (m, 4H) superimposed by 1.44 (d, J=7.1 Hz, 3H), 1.55-1.70 (m, 4H), 1.71-1.84 (m, 2H), 2.61-2.69 (m, 1H), 3.07-3.17 (m, 1H), 3.44 (m$_c$, 1H), 3.74 (s, 3H), 4.52 (d, J=4.5 Hz, 1H), 5.47 (q, J=7.1 Hz, 1H), 6.91 (dm, J=8.7 Hz, 2H), 7.21 (dm, J=8.7 Hz, 2H). The assignment of the configurations is based on an X-ray structure of the compound.

Examples 42 and 43

3-[(S)-1-(4-Chloro-phenyl)-ethyl]-trans-9-hydroxy-1-oxa-3-aza-spiro[5.5]undecan-2-one (42) and
3-[(S)-1-(4-Chloro-phenyl)-ethyl]-cis-9-hydroxy-1-oxa-3-aza-spiro[5.5]undecan-2-one (43)

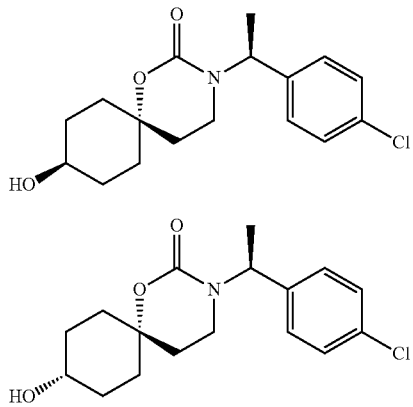

42

43

The title compounds are prepared from 3-[(S)-1-(4-chloro-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-1-(4-Chloro-phenyl)-ethyl]-trans-9-hydroxy-1-oxa-3-aza-spiro[5.5]undecan-2-one (42): Yield: 37% of theory; Mass spectrum (ESI+): m/z=324/326 (Cl) [M+H]+; $^1$H NMR (400 MHz, DMSO-$d_6$) δ 1.31-1.59 (m, 4H) superimposed by 1.47 (d, J=7.1 Hz, 3H), 1.62-1.79 (m, 5H), 1.83-1.91 (m, 1H), 2.68-2.76 (m, 1H), 3.16-3.23 (m, 1H), 3.69 (me, 1H), 4.46 (d, J=3.5 Hz, 1H), 5.45 (q, J=7.1 Hz, 1H), 7.31 (dm, J=8.5 Hz, 2H), 7.42 (dm, J=8.5 Hz, 2H).

3-[(S)-1-(4-Chloro-phenyl)-ethyl]-cis-9-hydroxy-1-oxa-3-aza-spiro[5.5]undecan-2-one (43): Yield: 43% of theory; Mass spectrum (ESI+): m/z=324/326 (Cl) [M+H]+; $^1$H NMR (400 MHz, DMSO-$d_6$) δ 1.33-1.54 (m, 4H) superimposed by 1.47 (d, J=7.2 Hz, 3H), 1.55-1.73 (m, 4H), 1.74-1.86 (m, 2H), 2.67-2.75 (m, 1H), 3.15-3.22 (m, 1H), 3.44 ($m_c$, 1H), 4.53 (d, J=4.4 Hz, 1H), 5.46 (q, J=7.2 Hz, 1H), 7.31 (dm, J=8.4 Hz, 2H), 7.42 (dm, J=8.4 Hz, 2H).

Examples 44 and 45

3-[(S)-(4-Bromophenyl)(cyclopropyl)methyl]-trans-9-hydroxy-1-oxa-3-azaspiro[5.5]undecan-2-one (44) and 3-[(S)-(4-Bromophenyl)(cyclopropyl)methyl]-cis-9-hydroxy-1-oxa-3-azaspiro[5.5]undecan-2-one (45)

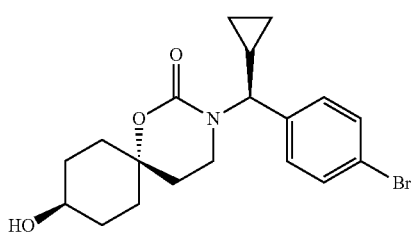

44

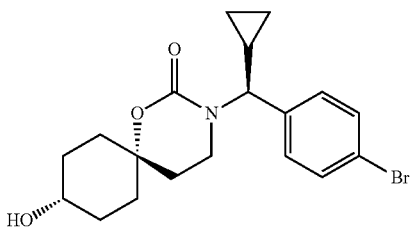

45

The title compounds are prepared from 3-[(S)-(4-bromophenyl)-cyclopropyl-methyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-(4-Bromophenyl)(cyclopropyl)methyl]-trans-9-hydroxy-1-oxa-3-azaspiro[5.5]undecan-2-one (44): Yield: 30% of theory; Mass spectrum (ESI+): m/z=394/396 (Br) [M+H]+; $^1$H NMR (400 MHz, DMSO-$d_6$) δ 0.28-0.37 (m, 1H), 0.39-0.47 (m, 1H), 0.55-0.64 (m, 1H), 0.73-0.82 (m, 1H), 1.33-1.63 (m, 5H), 1.65-1.83 (m, 5H), 1.90-1.99 (m, 1H), 2.88-2.96 (m, 1H), 3.37-3.46 (m, 1H), 3.70 ($m_c$, 1H), 4.45 (d, J=10.4 Hz, 1H), 4.49 (d, J=3.5 Hz, 1H), 7.34 (dm, J=8.3 Hz, 2H), 7.56 (dm, J=8.3 Hz, 2H).

3-[(S)-(4-Bromophenyl)(cyclopropyl)methyl]-cis-9-hydroxy-1-oxa-3-azaspiro[5.5]undecan-2-one (45): Yield: 26% of theory; Mass spectrum (ESI+): m/z=394/396 (Br) [M+H]+; $^1$H NMR (400 MHz, DMSO-$d_6$) δ 0.29-0.38 (m, 1H), 0.39-0.48 (m, 1H), 0.55-0.63 (m, 1H), 0.73-0.82 (m, 1H), 1.36-1.56 (m, 5H), 1.57-1.90 (m, 6H), 2.88-2.96 (m, 1H), 3.36-3.51 (m, 2H), 4.46 (d, J=10.4 Hz, 1H), 4.53 (d, J=4.5 Hz, 1H), 7.34 (dm, J=8.3 Hz, 2H), 7.56 (dm, J=8.4 Hz, 2H).

Examples 46 and 47

3-[(S)-1-(4-Cyano-phenyl)-ethyl]-trans-9-hydroxy-1-oxa-3-aza-spiro[5.5]undecan-2-one (46) and 3-[(S)-1-(4-Cyano-phenyl)-ethyl]-cis-9-hydroxy-1-oxa-3-aza-spiro[5.5]undecan-2-one (47)

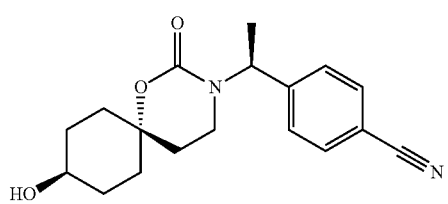

46

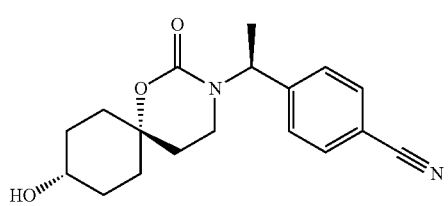

47

The title compounds are prepared from 3-[(S)-1-(4-cyano-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-1-(4-Cyano-phenyl)-ethyl]-trans-9-hydroxy-1-oxa-3-aza-spiro[5.5]undecan-2-one (46): Yield: 23% of theory; Mass spectrum (ESI⁺): m/z=315 [M+H]⁺; ¹H NMR (400 MHz, DMSO-d₆) δ 1.34-1.61 (m, 4H) superimposed by 1.52 (d, J=7.2 Hz, 3H), 1.65-1.82 (m, 5H), 1.87-1.95 (m, 1H), 2.76-2.84 (m, 1H), 3.21-3.29 (m, 1H), 3.70 (m$_c$, 1H), 4.47 (d, J=3.5 Hz, 1H), 5.46 (q, J=7.2 Hz, 1H), 7.48 (dm, J=8.2 Hz, 2H), 7.82 (dm, J=8.3 Hz, 2H).

3-[(S)-1-(4-Cyano-phenyl)-ethyl]-cis-9-hydroxy-1-oxa-3-aza-spiro[5.5]undecan-2-one (47): Yield: 30% of theory; Mass spectrum (ESI⁺): m/z=315 [M+H]⁺; ¹H NMR (400 MHz, DMSO-d₆) δ 1.34-1.55 (m, 4H) superimposed by 1.51 (d, J=7.2 Hz, 3H), 1.65-1.87 (m, 6H), 2.75-2.83 (m, 1H), 3.19-3.28 (m, 1H), 3.45 (m$_c$, 1H), 4.53 (d, J=4.5 Hz, 1H), 5.47 (q, J=7.2 Hz, 1H), 7.48 (dm, J=8.2 Hz, 2H), 7.83 (dm, J=8.2 Hz, 2H).

Example 48

3-[(S)-1-(4-Fluoro-phenyl)-ethyl]-1-oxa-3-aza-spiro[5.5]undecane-2,9-dione

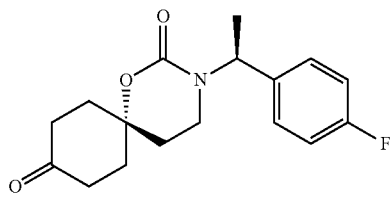

The title compound is prepared from 9-{2-[(S)-1-(4-fluoro-phenyl)-ethylamino]-ethyl}-3,3-dimethyl-1,5-dioxa-spiro[5.5]undecan-9-ol and triphosgene following a procedure analogous to that described in Step 4 of Intermediate 2. Yield: 50% of theory; LC (method 5): t$_R$=1.11 min; Mass spectrum (ESI⁺): m/z=306 [M+H]⁺.

Example 49

3-[(S)-1-(3,4-Difluoro-phenyl)-ethyl]-1-oxa-3-aza-spiro[5.5]undecane-2,9-dione

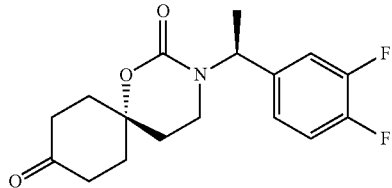

The title compound is prepared from 9-{2-[(S)-1-(3,4-difluoro-phenyl)-ethylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(3,4-difluoro-phenyl)-ethyl]-12,12-dimethyl-1,10,14-tri-oxa-3-aza-dispiro[5.2.5.2]hexadecan-2-one, obtained after that is treated as described in Step 10 of Intermediate 2 to convert the intermediate to the title compound, too. Yield: 68% of theory; LC (method 6): t$_R$=1.14 min; Mass spectrum (ESI⁺): m/z=324 [M+H]⁺.

Examples 50 and 51 trans-9-Hydroxy-3-[(S)-1-(4-methylphenyl)-ethyl]-1-oxa-3-aza-spiro[5.5]undecan-2-one (50) and cis-9-Hydroxy-3-[(S)-1-(4-methylphenyl)-ethyl]-1-oxa-3-aza-spiro[5.5]undecan-2-one (51)

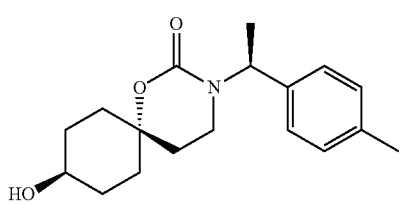

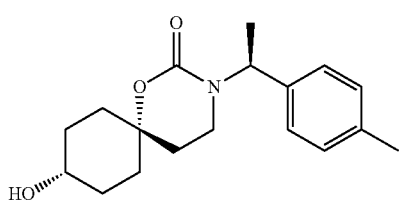

The title compounds are prepared from 3-[(S)-1-(4-methylphenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 µm; eluent: methanol containing 0.2% diethylamine/sc carbon dioxide 30:70; flow: 4 mL/min).

trans-9-Hydroxy-3-[(S)-1-(4-methylphenyl)-ethyl]-1-oxa-3-aza-spiro[5.5]undecan-2-one (50): Yield: 44% of theory; LC (method 6): t$_R$=1.25 min; Mass spectrum (ESI⁺): m/z=304 [m+H]⁺.

cis-9-Hydroxy-3-[(S)-1-(4-methylphenyl)-ethyl]-1-oxa-3-aza-spiro[5.5]undecan-2-one (51): Yield: 40% of theory; LC (method 6): t$_R$=1.30 min; Mass spectrum (ESI⁺): m/z=304 [M+H]⁺.

Example 52

3-[(S)-1-(4-Trifluoromethyl-phenyl)-ethyl]-1-oxa-3-aza-spiro[5.5]undecane-2,9-dione

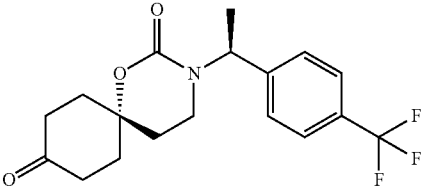

The title compound is prepared from 3,3-dimethyl-9-{2-[(S)-1-(4-trifluoromethyl-phenyl)-ethylamino]-ethyl}-1,5-dioxa-spiro[5.5]undecan-9-ol and triphosgene following a procedure analogous to that described in Step 4 of Intermediate 2; the crude product, a mixture of the title compound and 12,12-dimethyl-3-[(S)-1-(4-trifluoromethyl-phenyl)-ethyl]-

1,10,14-trioxa-3-aza-dispiro[5.2.5.2]hexadecan-2-one, obtained after that is treated as described in Step 10 of Intermediate 2 to convert the intermediate to the title compound, too. Yield: 67% of theory; LC (method 6): $t_R$=1.28 min; Mass spectrum (ESI$^+$): m/z=356 [M+H]$^+$.

Examples 53 and 54 trans-9-Hydroxy-3-[(S)-1-(4-fluoro-phenyl)-ethyl]-1-oxa-3-aza-spiro[5.5]undecan-2-one (53) and cis-9-Hydroxy-3-[(S)-1-(4-fluoro-phenyl)-ethyl]-1-oxa-3-aza-spiro[5.5]undecan-2-one (54)

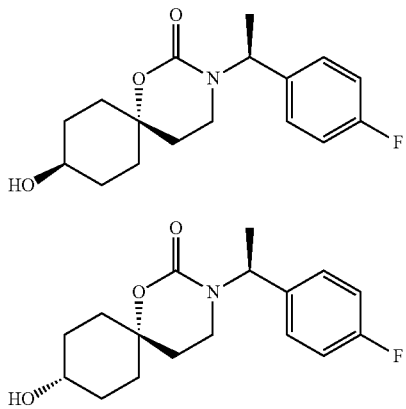

The title compounds are prepared from 3-[(S)-1-(4-fluoro-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 ml/min).

trans-9-Hydroxy-3-[(S)-1-(4-fluoro-phenyl)-ethyl]-1-oxa-3-aza-spiro[5.5]undecan-2-one (53): Yield: 43% of theory; LC (method 6): $t_R$=1.12 min; Mass spectrum (ESI$^+$): m/z=308 [m+H]$^+$.

cis-9-Hydroxy-3-[(S)-1-(4-fluoro-phenyl)-ethyl]-1-oxa-3-aza-spiro[5.5]undecan-2-one (54): Yield: 41% of theory; LC (method 6): $t_R$=1.16 min; Mass spectrum (ESI$^+$): m/z=308 [M+H]$^+$.

Example 55

3-[(S)-1-(4-Cyclopropyl-phenyl)-ethyl]-1-oxa-3-aza-spiro[5.5]undecane-2,9-dione

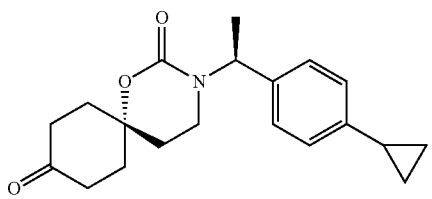

A flask charged with a stir bar, 3-[(S)-1-(4-bromo-phenyl)-ethyl]-1-oxa-3-aza-spiro[5.5]un-decane-2,9-dione (0.50 g), cyclopropylboronic acid (0.23 g), tricyclohexylphosphonium tetrafluoroborate (0.10 g), potassium phosphate (1.54 g), toluene (5 mL), and water (0.25 mL) is sparged with argon for 5 min. Palladium(II) acetate (31 mg) is then added and the mixture is heated to 105° C. and stirred at this temperature overnight. After cooling to ambient temperature, water is added and the resulting mixture is filtered. The aqueous phase of the filtrate is separated and extracted with ethyl acetate. The combined organic phases are washed with brine, dried (MgSO$_4$), and concentrated. The residue is chromatographed on silica gel (cyclohexane/ethyl acetate 3:1→0:1) to afford the title compound. Yield: 0.12 g (27% of theory); LC (method 6): $t_R$=1.36 min; Mass spectrum (ESI$^+$): m/z=328 [M+H]$^+$.

Examples 56 and 57

3-[(S)-1-(4-Bromo-phenyl)-ethyl]-2-oxo-1-oxa-3-aza-spiro[5.5]undecane-9-cis-carboxylic acid ethyl ester (56) and 3-[(S)-1-(4-Bromo-phenyl)-ethyl]-2-oxo-1-oxa-3-aza-spiro[5.5]undecane-9-trans-carboxylic acid ethyl ester (57)

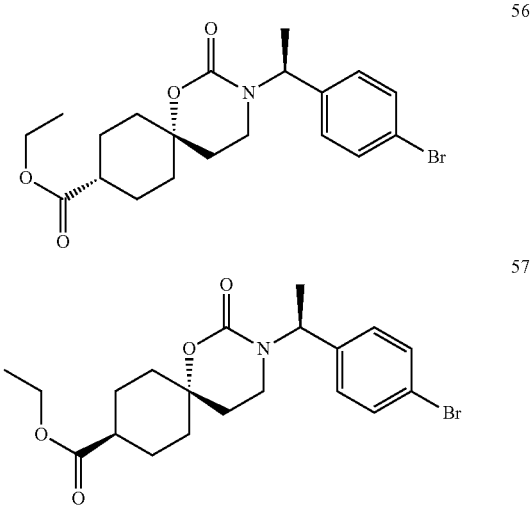

The title compounds are prepared from 4-{2-[(S)-1-(4-bromo-phenyl)-ethylamino]-ethyl}-4-hydroxy-cyclohexanecarboxylic acid ethyl ester (mixture of diastereomers) and triphosgene following a procedure analogous to that described in Step 4 of Intermediate 2 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-1-(4-Bromo-phenyl)-ethyl]-2-oxo-1-oxa-3-aza-spiro[5.5]undecane-9-cis-carboxylic acid ethyl ester (56): Yield: 23% of theory; Mass spectrum (ESI$^+$): m/z=424 [M+H]$^+$; $^1$H NMR (400 MHz, DMSO-d$_6$) δ 1.17 (t, J=7.1 Hz, 3H), 1.47 (d, J=7.2 Hz, 3H), 1.52-1.97 (m, 10H), 2.42-2.51 (m, 1H), 2.68-2.76 (m, 1H), 3.13-3.22 (m, 1H), 4.05 (q, J=7.1 Hz, 2H), 5.42 (q, J=7.2 Hz, 1H), 7.25 (dm, J=8.4 Hz, 2H), 7.55 (d, J=8.4 Hz, 2H).

3-[(S)-1-(4-Bromo-phenyl)-ethyl]-2-oxo-1-oxa-3-aza-spiro[5.5]undecane-9-trans-carboxylic acid ethyl ester (57): Yield: 38% of theory; Mass spectrum (ESI$^+$): m/z=424 [M+H]$^+$; $^1$H NMR (400 MHz, DMSO-d$_6$) δ 1.19 (t, J=7.1 Hz, 3H), 1.38-1.49 (m, 2H) superimposed by 1.47 (d, J=7.2 Hz, 3H), 1.59-1.89 (m, 8H), 2.28-2.38 (m, 1H), 2.69-2.77 (m, 1H), 3.16-3.25 (m, 1H), 4.07 (q, J=7.1 Hz, 2H), 5.44 (q, J=7.2 Hz, 1H), 7.25 (dm, J=8.4 Hz, 2H), 7.55 (d, J=8.4 Hz, 2H).

Example 58

3-[(S)-1-(4-Difluoromethoxy-phenyl)-ethyl]-1-oxa-3-aza-spiro[5.5]undecane-2,9-dione

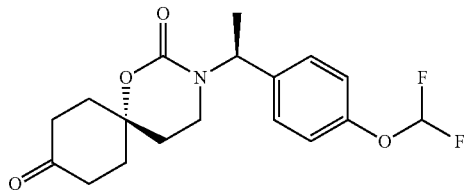

The title compound is prepared from 9-{2-[(S)-1-(4-difluoromethoxy-phenyl)-ethylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(4-difluoromethoxy-phenyl)-ethyl]-12,12-dimethyl-1,10,14-trioxa-3-aza-dispiro[5.2.5.2]hexadecan-2-one, obtained after that is treated as described in Step 10 of Intermediate 2 to convert the intermediate to the title compound, too. Yield: 45% of theory; LC (method 6): $t_R$=1.14 min; Mass spectrum (ESI$^+$): m/z=354 [M+H]$^+$.

Example 59

3-[(S)-1-(4-Bromo-phenyl)-ethyl]-2-oxo-1-oxa-3-aza-spiro[5.5]undecane-trans-9-carboxylic acid

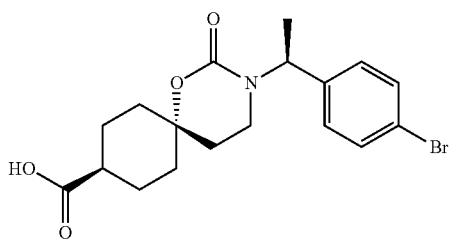 [SMILES: C[C@@H](c1ccc(Br)cc1)N1CC[C@]2(CC[C@@H](C(=O)O)CC2)OC1=O]

1 M aqueous NaOH solution (0.85 mL) is added to solution of 3-[(S)-1-(4-bromo-phenyl)-ethyl]-2-oxo-1-oxa-3-aza-spiro[5.5]undecane-trans-9-carboxylic acid ethyl ester (0.17 g) in methanol (2 mL). The resulting solution is stirred at room temperature for 3 h. 1 M aqueous HCl solution (0.9 mL) is then added and the precipitate formed thereafter is separated by filtration and dried to afford the title compound as a colorless solid. Yield: 0.16 (quantitative); LC (method 6): $t_R$=1.36 min; Mass spectrum (ESI$^+$): m/z=396/398 (Br) [M+H]$^+$.

Example 60

3-[(S)-1-(2,5-Dimethyl-phenyl)-ethyl]-1-oxa-3-aza-spiro[5.5]undecane-2,9-dione

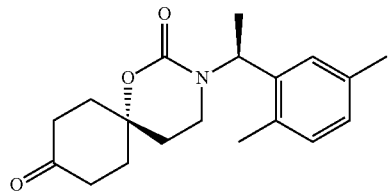

The title compound is prepared from 9-{2-[(S)-1-(2,5-dimethyl-phenyl)-ethylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(2,5-dimethyl-phenyl)-ethyl]-12,12-dimethyl-1,10,14-trioxa-3-aza-dispiro[5.2.5.2]hexadecan-2-one, obtained after that is treated as described in Step 10 of Intermediate 2 to convert the intermediate to the title compound, too. Yield: 49% of theory; Mass spectrum (ESI$^+$): m/z=316 [M+H]$^+$; $^1$H NMR (400 MHz, DMSO-d$_6$) δ 1.47 (d, J=7.2 Hz, 3H), 1.79-2.00 (m, 5H), 2.05-2.13 (m, 1H), 2.15-2.25 (m, 2H) superimposed by 2.20 (s, 3H) and 2.22 (s, 3H), 2.44-2.55 (m, 2H), 2.70-2.78 (m, 1H), 3.16-3.24 (m, 1H), 5.48 (q, J=7.2 Hz, 1H), 7.02 (dm, J=7.8 Hz, 1H), 7.08 (broad s, 1H), 7.12 (d, J=7.8 Hz, 1H).

Examples 61 and 62

3-[(S)-1-(4-Bromo-phenyl)-ethyl]-trans-9-hydroxy-9-methyl-1-oxa-3-aza-spiro[5.5]undecan-2-one (61) and 3-[(S)-1-(4-Bromo-phenyl)-ethyl]-cis-9-hydroxy-9-methyl-1-oxa-3-aza-spiro[5.5]undecan-2-one (62)

61

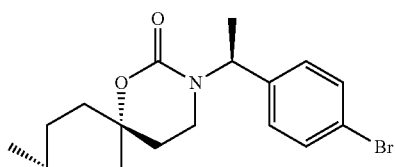

62

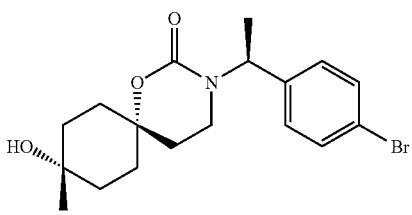

MeMgBr (1.4 mol/L in toluene/tetrahydrofuran, 1.56 mL) is added to a solution of 3-[(S)-1-(4-bromo-phenyl)-ethyl]-1-oxa-3-aza-spiro[5.5]undecane-2,9-dione (0.40 g) in tetrahydrofuran (4 mL) chilled in an ice bath. The solution is stirred with cooling for 2 h and the reaction is then quenched by the addition of aqueous NH$_4$Cl solution. The resulting mixture is extracted with tert-butyl methyl ether and the combined extracts are dried (Na$_2$SO$_4$). The solvent is evaporated and the residue is purified by HPLC on reversed phase (methanol/water) to give a mixture of the title compounds that is separated by SFC on chiral phase (column: Daicel IC, 250×4.6 mm, 5 µm; eluent: methanol containing 0.2% diethylamine/sc carbon dioxide 30:70; flow: 4 mL/min).

3-[(S)-1-(4-Bromo-phenyl)-ethyl]-trans-9-hydroxy-9-methyl-1-oxa-3-aza-spiro[5.5]undecan-2-one (61): Yield: 69 mg (17% of theory); Mass spectrum (ESI$^+$): m/z=382/384 (Br) [M+H]$^+$.

3-[(S)-1-(4-Bromo-phenyl)-ethyl]-cis-9-hydroxy-9-methyl-1-oxa-3-aza-spiro[5.5]undecan-2-one (62): Yield: 73 mg (17% of theory); Mass spectrum (ESI$^+$): m/z=382/384 (Br) [M+H]$^+$.

Example 63

3-[(S)-1-(4-Bromo-phenyl)-ethyl]-2-oxo-1-oxa-3-aza-spiro[5.5]undecane-cis-9-carboxylic acid

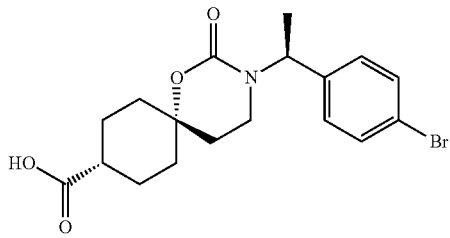 [SMILES: C[C@@H](c1ccc(Br)cc1)N1CC[C@]2(CC[C@H](C(=O)O)CC2)OC1=O]

The title compound is prepared from 3-[(S)-1-(4-bromo-phenyl)-ethyl]-2-oxo-1-oxa-3-aza-spiro[5.5]undecane-cis-9-carboxylic acid ethyl ester following a procedure analogous to that described in Example 59. Yield: 82% of theory; LC (method 6): t$_R$=1.32 min; Mass spectrum (ESI$^+$): m/z=396/398 (Br) [M+H]$^+$.

Examples 64 and 65

3-[(S)-1-(4-Bromo-phenyl)-ethyl]-trans-9-hydroxymethyl-1-oxa-3-aza-spiro[5.5]undecan-2-one (64) and 3-[(S)-1-(4-Bromo-phenyl)-ethyl]-cis-9-hydroxymethyl-1-oxa-3-aza-spiro[5.5]undecan-2-one (65)

64
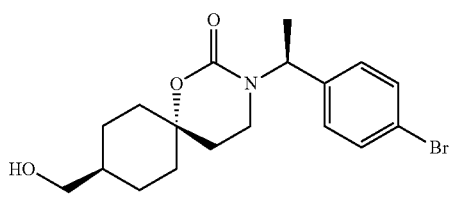

65
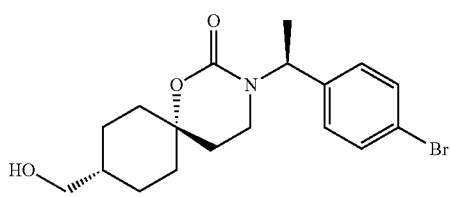

1,1'-Carbonyldiimidazole (0.18 g) is added to a solution of 3-[(S)-1-(4-bromo-phenyl)-ethyl]-2-oxo-1-oxa-3-aza-spiro[5.5]undecane-9-carboxylic acid (cis/trans mixture at C-9, 0.25 g) in tetrahydrofuran (3 mL) at room temperature. The solution is stirred at room temperature until TLC indicates complete consumption of the starting compound. NaBH$_4$ (0.12 g) dissolved in water (1.5 mL) is then added and stirring is continued overnight. Ethyl acetate is added and the resulting mixture is washed with aqueous K$_2$CO$_3$ solution. The organic phase is dried (Na$_2$SO$_4$) and the solvent is evaporated. The residue is purified by HPLC on reversed phase (methanol/water) to give a mixture of the title compounds that is separated by SFC on chiral phase (column: Daicel IC, 250×4.6 mm, 5 µm; eluent: methanol containing 0.2% diethylamine/sc carbon dioxide 30:70; flow: 4 mL/min).

3-[(S)-1-(4-Bromo-phenyl)-ethyl]-trans-9-hydroxymethyl-1-oxa-3-aza-spiro[5.5]undecan-2-one (64): Yield: 23 mg (10% of theory); SFC (column: Daicel IC, 250×4.6 mm, 5 µm; eluent: methanol containing 0.2% diethylamine/sc carbon dioxide 30:70; flow: 4 mL/min): t$_R$=4.55 min; Mass spectrum (ESI$^+$): m/z=382/384 (Br) [M+H]$^+$.

3-[(S)-1-(4-Bromo-phenyl)-ethyl]-cis-9-hydroxymethyl-1-oxa-3-aza-spiro[5.5]undecan-2-one (65): Yield: 25 mg (10% of theory); SFC (column: Daicel IC, 250×4.6 mm, 5 µm; eluent: methanol containing 0.2% diethylamine/sc carbon dioxide 30:70; flow: 4 mL/min): t$_R$=3.82 min; Mass spectrum (ESI$^+$): m/z=382/384 (Br) [M+H]$^+$.

Examples 66 and 67

3-[(S)-1-(4-Difluoromethoxy-phenyl)-ethyl]-trans-9-hydroxy-1-oxa-3-aza-spiro[5.5]undecan-2-one (66) and 3-[(S)-1-(4-Difluoromethoxy-phenyl)-ethyl]-cis-9-hydroxy-1-oxa-3-aza-spiro[5.5]undecan-2-one (67)

66
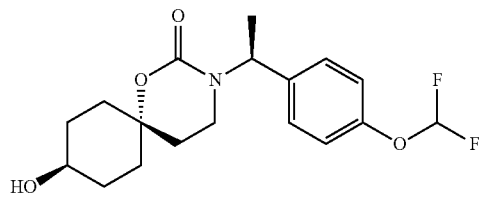

67
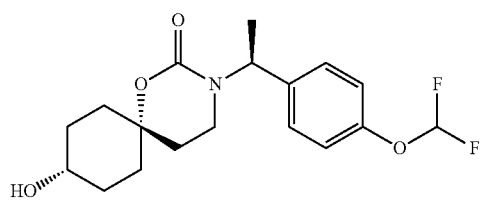

The title compounds are prepared from 3-[(S)-1-(4-difluoromethoxy-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 µm; eluent: methanol containing 0.2% diethylamine/sc carbon dioxide 30:70; flow: 4 mL/min).

3-[(S)-1-(4-Difluoromethoxy-phenyl)-ethyl]-trans-9-hydroxy-1-oxa-3-aza-spiro[5.5]undecan-2-one (66): Yield: 21% of theory; LC (method 6): t$_R$=1.15 min; Mass spectrum (ESI$^+$): m/z=356 [M+H]$^+$.

3-[(S)-1-(4-Difluoromethoxy-phenyl)-ethyl]-cis-9-hydroxy-1-oxa-3-aza-spiro[5.5]undecan-2-one (67): Yield: 26% of theory; LC (method 6): t$_R$=1.19 min;
Mass spectrum (ESI$^+$): m/z=356 [M+H]$^+$.

Examples 68 and 69 trans-9-Hydroxy-3-[(S)-1-(4-trifluoromethyl-phenyl)-ethyl]-1-oxa-3-aza-spiro[5.5]undecan-2-one (68) and cis-9-Hydroxy-3-[(S)-1-(4-trifluoromethyl-phenyl)-ethyl]-1-oxa-3-aza-spiro[5.5]undecan-2-one (69)

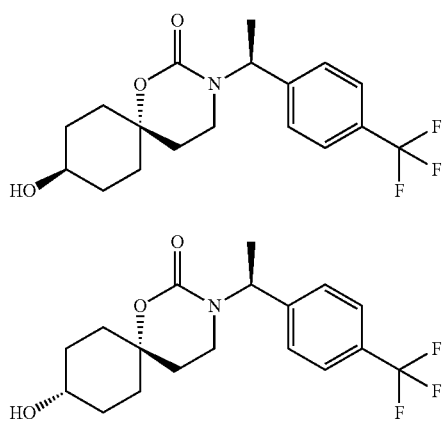

The title compounds are prepared from 3-[(S)-1-(4-trifluoromethyl-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

trans-9-Hydroxy-3-[(S)-1-(4-trifluoromethyl-phenyl)-ethyl]-1-oxa-3-aza-spiro[5.5]undecan-2-one (68): Yield: 22% of theory; LC (method 6): $t_R$=1.29 min; Mass spectrum (ESI$^+$): m/z=358 [M+H]$^+$.

cis-9-Hydroxy-3-[(S)-1-(4-trifluoromethyl-phenyl)-ethyl]-1-oxa-3-aza-spiro[5.5]undecan-2-one (69): Yield: 24% of theory; LC (method 6): $t_R$=1.32 min; Mass spectrum (ESI$^+$): m/z=358 [M+H]$^+$.

Examples 70 and 71

3-[(S)-1-(4-Cyclopropyl-phenyl)-ethyl]-trans-9-hydroxy-1-oxa-3-aza-spiro[5.5]undecan-2-one (70) and 3-[(S)-1-(4-Cyclopropyl-phenyl)-ethyl]-cis-9-hydroxy-1-oxa-3-aza-spiro[5.5]undecan-2-one (71)

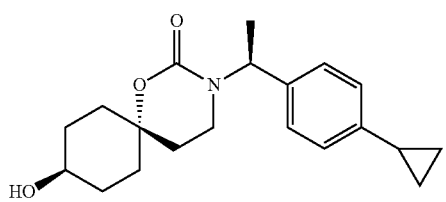

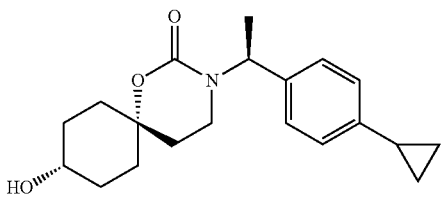

The title compounds are prepared from 3-[(S)-1-(4-cyclopropyl-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-1-(4-Cyclopropyl-phenyl)-ethyl]-trans-9-hydroxy-1-oxa-3-aza-spiro[5.5]undecan-2-one (70): Yield: 26% of theory; SFC (column: Daicel IC, 250×4.6 mm, 5 μm; eluent: methanol containing 0.2% diethylamine/sc carbon dioxide 30:70; flow: 4 mL/min): $t_R$=2.92 min; Mass spectrum (ESI$^+$): m/z=330 [M+H]$^+$.

3-[(S)-1-(4-Cyclopropyl-phenyl)-ethyl]-cis-9-hydroxy-1-oxa-3-aza-spiro[5.5]undecan-2-one (71): Yield: 26% of theory; SFC (column: Daicel IC, 250×4.6 mm, 5 μm; eluent: methanol containing 0.2% diethylamine/sc carbon dioxide 30:70; flow: 4 mL/min): $t_R$=4.87 min; Mass spectrum (ESI$^+$): m/z=330 [M+H]$^+$.

Example 72

3-[(S)-1-(2,5-Dimethyl-phenyl)-ethyl]-9-hydroxy-1-oxa-3-aza-spiro[5.5]undecan-2-one

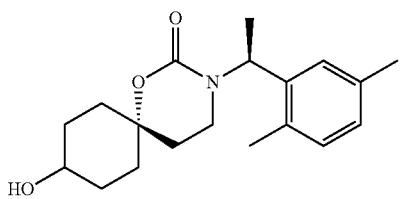

The title compound is prepared from 3-[(S)-1-(2,5-dimethyl-phenyl)-ethyl]-1-oxa-3-aza-spiro[5.5]undecane-2,9-dione following a procedure analogous to that described in Example 22; the title compound is obtained as a ca. 1:1 mixture of the cis- and trans-isomer. Yield: 75% of theory; Mass spectrum (ESI$^+$): m/z=318 [M+H]$^+$; $^1$H NMR (400 MHz, DMSO-d$_6$) δ 1.30-1.88 (m, 10H) superimposed by 1.44 (d, J=7.2 Hz, 3H), 2.19 (s, 3H), 2.21 (s, 3H), 2.62-2.71 (m, 1H), 3.08-3.17 (m, 3H), 3.44 (m$_c$, 0.5H), 3.69 (m$_c$, 0.5H), 3.46 (d, J=3.3 Hz, 0.5H), 4.52 (d, J=4.5 Hz, 0.5H), 5.41-5.49 (m, 1H), 6.99 (dm, J=7.9 Hz, 1H), 7.04 (s, 1H), 7.11 (d, J=7.8 Hz, 2H).

Examples 73 and 74

3-[(S)-1-(3,4-Difluoro-phenyl)-ethyl]-trans-9-hydroxy-1-oxa-3-aza-spiro[5.5]undecan-2-one (73) and 3-[(S)-1-(3,4-Difluoro-phenyl)-ethyl]-cis-9-hydroxy-1-oxa-3-aza-spiro[5.5]undecan-2-one (74)

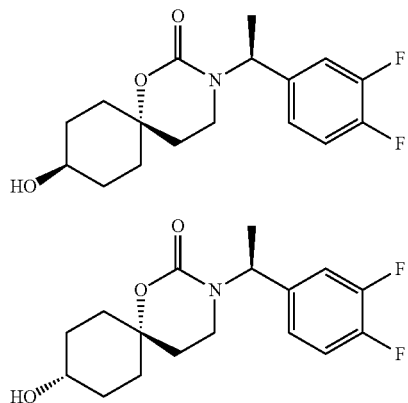

The title compounds are prepared from 3-[(S)-1-(3,4-difluoro-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-1-(3,4-Difluoro-phenyl)-ethyl]-trans-9-hydroxy-1-oxa-3-aza-spiro[5.5]undecan-2-one (73): Yield: 20% of theory; LC (method 6): $t_R$=1.15 min; Mass spectrum (ESI$^+$): m/z=326 [M+H]$^+$.

3-[(S)-1-(3,4-Difluoro-phenyl)-ethyl]-cis-9-hydroxy-1-oxa-3-aza-spiro[5.5]undecan-2-one (74): Yield: 27% of theory; LC (method 6): $t_R$=1.18 min; Mass spectrum (ESI$^+$): m/z=326 [m+H]$^+$.

Examples 75 and 76

3-[(S)-1-(4-Bromo-phenyl)-ethyl]-2-oxo-1-oxa-3-aza-spiro[5.5]undecane-cis-9-carboxylic acid amide (75) and 3-[(S)-1-(4-Bromo-phenyl)-ethyl]-2-oxo-1-oxa-3-aza-spiro[5.5]undecane-trans-9-carboxylic acid amide (76)

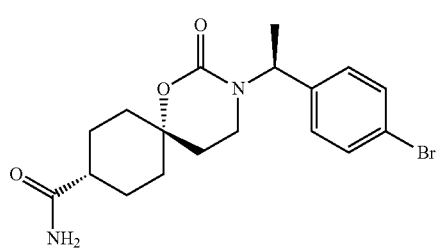

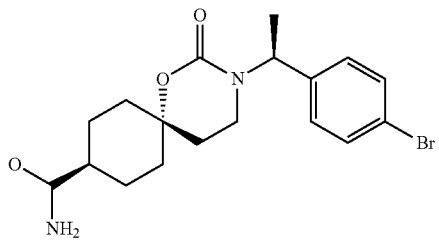

2-(1H-Benzotriazol-1-yl)-1,1,3,3-tetramethyluronium tetrafluoroborate (0.22 g) is added to a solution of 3-[(S)-1-(4-bromo-phenyl)-ethyl]-2-oxo-1-oxa-3-aza-spiro[5.5]undecane-9-carboxylic acid (cis/trans mixture, 0.25 g) and ethyldiisopropyl-amine (0.12 mL) in N,N-dimethylformamide (2 mL) at room temperature. The solution is stirred for 20 min prior to the addition of ammonia (32% in water, 0.10 mL). The resulting solution is stirred at room temperature for 4 h and then concentrated. The residue is purified HPLC on reversed phase (methanol/water) to afford a mixture of the two title compounds which are separated by SFC on chiral phase (column: Daicel IC, 250×4.6 mm, 5 μm; eluent: methanol containing 0.2% diethylamine/sc carbon dioxide 30:70; flow: 4 mL/min) to give each title compound as a solid.

3-[(S)-1-(4-Bromo-phenyl)-ethyl]-2-oxo-1-oxa-3-aza-spiro[5.5]undecane-cis-9-carboxylic acid amide (75): Yield: 0.07 g (26% of theory); SFC (column: Daicel IC, 250×4.6 mm, 5 μm; eluent: methanol containing 0.2% diethylamine/sc carbon dioxide 30:70; flow: 4 mL/min): $t_R$=6.36 min; Mass spectrum (ESI$^+$): m/z=395/397 (Br) [M+H]$^+$.

3-[(S)-1-(4-Bromo-phenyl)-ethyl]-2-oxo-1-oxa-3-aza-spiro[5.5]undecane-trans-9-carboxylic acid amide (76): Yield: 0.14 g (56% of theory); SFC (column: Daicel IC, 250×4.6 mm, 5 μm; eluent: methanol containing 0.2% diethylamine/sc carbon dioxide 30:70; flow: 4 mL/min): $t_R$=8.04 min; Mass spectrum (ESI$^+$): m/z=395/397 (Br) [M+H]$^+$.

Example 77

3-[(S)-1-(4-Trifluoromethoxy-phenyl)-ethyl]-1-oxa-3-aza-spiro[5.5]undecane-2,9-dione

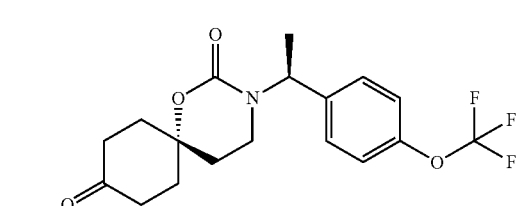

The title compound is prepared from 3,3-dimethyl-9-{2-[(S)-1-(4-trifluoromethoxy-phenyl)-ethylamino]-ethyl}-1,5-dioxa-spiro[5.5]undecan-9-ol and triphosgene following a procedure analogous to that described in Step 4 of Intermediate 2; the crude product, a mixture of the title compound and 12,12-dimethyl-3-[(S)-1-(4-trifluoromethoxy-phenyl)-ethyl]-1,10,14-trioxa-3-aza-dispiro[5.2.5.2]hexadecan-2-one, obtained after that is treated as described in Step 10 of Intermediate 2 to convert the intermediate to the title compound as well. Yield: 57% of theory; LC (method 6): $t_R$=1.33 min; Mass spectrum (ESI$^+$): m/z=372 [M+H]$^+$.

Example 78

3-[(S)-1-(4-Chloro-phenyl)-propyl]-1-oxa-3-aza-spiro[5.5]undecane-2,9-dione

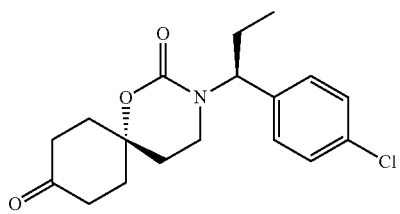

The title compound is prepared from 9-{2-[(S)-1-(4-chloro-phenyl)-propylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(4-chloro-phenyl)-propyl]-12,12-dimethyl-1,10,14-trioxa-3-aza-dispiro[5.2.5.2]hexadecan-2-one, obtained after that is treated as described in Step 10 of Intermediate 2 to convert the intermediate to the title compound as well. Yield: 68% of theory; LC (method 6): $t_R$=1.32 min; Mass spectrum (ESI$^+$): m/z=336/338 (Cl) [M+H]$^+$.

Example 79

3-[(S)-1-(4-Bromo-phenyl)-ethyl]-3-aza-spiro[5.5]undecane-2,9-dione

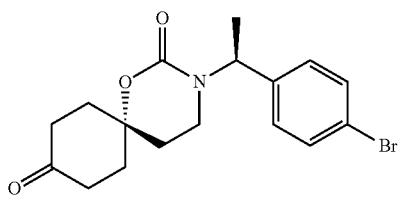

The title compound is prepared from 12-[(S)-1-(4-bromo-phenyl)-ethyl]-3,3-dimethyl-1,5-dioxa-12-aza-dispiro[5.2.5.2]hexadecan-11-one following a procedure analogous to that described in Step 10 of Intermediate 2. Yield: 41% of theory; LC (method 6): $t_R$=1.37 min; Mass spectrum (ESI$^+$): m/z=364/366 (Br) [M+H]$^+$.

Example 80

3-[(S)-1-(4-tert-Butyl-phenyl)-ethyl]-1-oxa-3-aza-spiro[5.5]undecane-2,9-dione

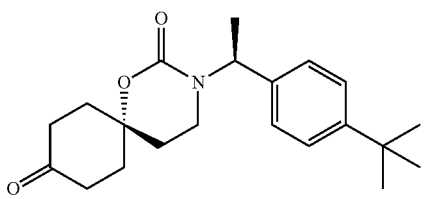

The title compound is prepared from 9-{2-[(S)-1-(4-tert-butyl-phenyl)-ethylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(4-tert-butyl-phenyl)-ethyl]-12,12-dimethyl-1,10,14-trioxa-3-aza-dispiro[5.2.5.2]hexadecan-2-one, obtained after that is treated as described in Step 10 of Intermediate 2 to convert the intermediate to the title compound as well. Yield: 65% of theory; LC (method 6): $t_R$=1.51 min; Mass spectrum (ESI$^+$): m/z=344 [M+H]$^+$.

Examples 81

3-[(S)-1-(2,4-Difluoro-phenyl)-ethyl]-9-hydroxy-1-oxa-3-aza-spiro[5.5]undecan-2-one

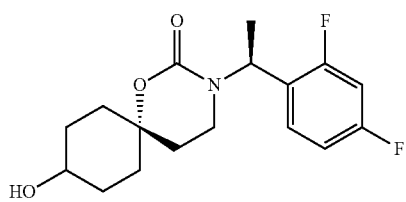

The title compound is prepared from 3-[(S)-1-(2,4-difluoro-phenyl)-ethyl]-1-oxa-3-aza-spiro[5.5]undecane-2,9-dione following a procedure analogous to that described in Example 22 and obtained as a mixture of cis/trans isomers. Yield: 67% of theory; Mass spectrum (ESI$^+$): m/z=326 [M+H]$^+$.

Examples 82 and 83

3-[(S)-1-(4-Bromo-phenyl)-ethyl]-cis-9-hydroxy-3-aza-spiro[5.5]undecan-2-one (82) and 3-[(S)-1-(4-Bromo-phenyl)-ethyl]-trans-9-hydroxy-3-aza-spiro[5.5]undecan-2-one (83)

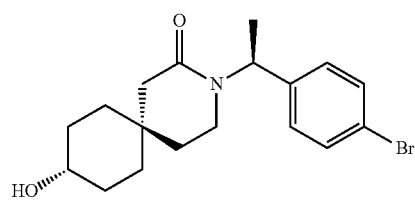

82

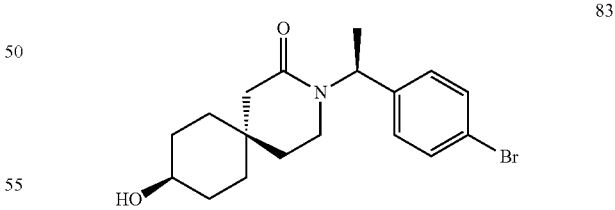

83

The title compounds are prepared from 3-[(S)-1-(4-bromo-phenyl)-ethyl]-3-aza-spiro[5.5]undecane-2,9-dione following a procedure analogous to that described in Example 22 and separated by HPLC on reversed phase (methanol/water).
3-[(S)-1-(4-Bromo-phenyl)-ethyl]-cis-9-hydroxy-3-aza-spiro[5.5]undecan-2-one (82): Yield: 22% of theory; Mass spectrum (ESI$^+$): m/z=366/368 (Br) [M+H]$^+$; $^1$H NMR (400 MHz, DMSO-d$_6$) δ 1.07-1.39 (m, 5H), 1.42 (d, J=7.2 Hz, 3H), 1.45-1.71 (m, 5H), 2.06 (d, J=17.0 Hz, 1H), 2.12 (d, J=17.0 Hz, 1H), 2.63-2.71 (m, 1H), 3.09-3.18 (m, 1H), 3.41 (m$_c$, 1H), 4.41 (d, J=4.1 Hz, 1H), 5.80 (q, J=7.2 Hz, 1H), 7.21 (dm, J=8.4 Hz, 2H), 7.53 (dm, J=8.4 Hz, 2H).

3-[(S)-1-(4-Bromo-phenyl)-ethyl]-trans-9-hydroxy-3-aza-spiro[5.5]undecan-2-one (83): Yield: 17% of theory; Mass spectrum (ESI+): m/z=366/368 (Br) [M+H]+; 1H NMR (400 MHz, DMSO-d6) δ 1.04-1.65 (m, 13H) superimposed by 1.42 (d, J=7.2 Hz, 3H), 2.17 (d, J=17.1 Hz, 1H), 2.23 (d, J=17.1 Hz, 1H), 2.62-2.70 (m, 1H), 3.09-3.18 (m, 1H), 3.41 (m$_c$, 1H), 4.40 (d, J=4.4 Hz, 1H), 5.80 (q, J=7.2 Hz, 1H), 7.21 (dm, J=8.4 Hz, 2H), 7.53 (dm, J=8.4 Hz, 2H).

Example 84

3-[(S)-1-(4-Methoxy-phenyl)-propyl]-1-oxa-3-aza-spiro[5.5]undecane-2,9-dione

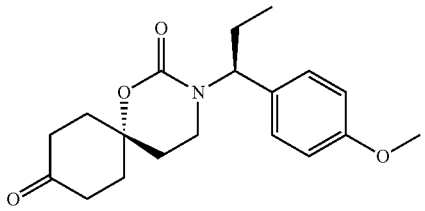

The title compound is prepared from 9-{2-[(S)-1-(4-methoxy-phenyl)-propylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(4-methoxy-phenyl)-propyl]-12,12-dimethyl-1,10,14-tri-oxa-3-aza-dispiro[5.2.5.2]hexadecan-2-one, obtained after that is treated as described in Step 10 of Intermediate 2 to convert the intermediate to the title compound as well. Yield: 62% of theory; LC (method 6): t$_R$=1.33 min; Mass spectrum (ESI+): m/z=332 [M+H]+.

Examples 85 and 86

3-[1-(4-Bromo-phenyl)-1-methyl-ethyl]-trans-9-hydroxy-1-oxa-3-aza-spiro[5.5]undecan-2-one (85) and 3-[1-(4-Bromo-phenyl)-1-methyl-ethyl]-cis-9-hydroxy-1-oxa-3-aza-spiro[5.5]undecan-2-one (86)

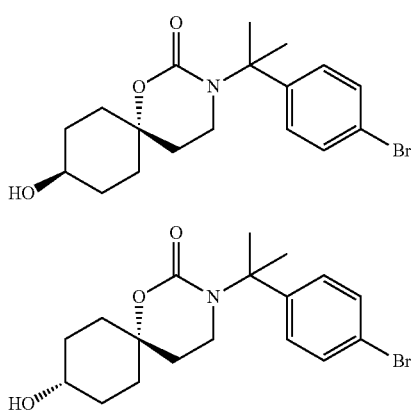

The title compounds are prepared from 3-[1-(4-bromo-phenyl)-1-methyl-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[1-(4-Bromo-phenyl)-1-methyl-ethyl]-trans-9-hydroxy-1-oxa-3-aza-spiro[5.5]undecan-2-one (85): Yield: 12% of theory; LC (method 6): t$_R$=1.30 min; Mass spectrum (ESI+): m/z=382/384 (Br) [M+H]+.

3-[1-(4-Bromo-phenyl)-1-methyl-ethyl]-cis-9-hydroxy-1-oxa-3-aza-spiro[5.5]undecan-2-one (86): Yield: 20% of theory; LC (method 6): t$_R$=1.33 min; Mass spectrum (ESI+): m/z=382/384 (Br) [M+H]+.

Example 87

3-[(S)-1-Phenyl-ethyl]-1-oxa-3-aza-spiro[5.5]undecane-2,9-dione

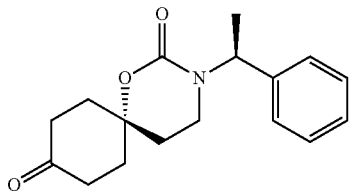

The title compound is prepared from 3,3-dimethyl-9-{2-[(S)-1-phenyl-ethylamino]-ethyl}-1,5-dioxa-spiro[5.5]undecan-9-ol and triphosgene following a procedure analogous to that described in Step 4 of Intermediate 2; the crude product, a mixture of the title compound and 12,12-dimethyl-3-[(S)-1-phenyl-ethyl]-1,10,14-trioxa-3-aza-dispiro[5.2.5.2] hexadecan-2-one, obtained thereafter is treated as described in Step 10 of Intermediate 2 to convert the intermediate to the title compound as well. Yield: 49% of theory; LC (method 6): t$_R$=1.06 min; Mass spectrum (ESI+): m/z=288 [M+H]+.

Example 88

3-[(S)-1-Naphthalen-2-yl-ethyl]-1-oxa-3-aza-spiro[5.5]undecane-2,9-dione

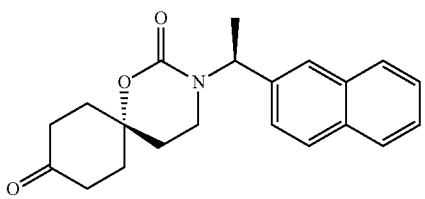

The title compound is prepared from 3,3-dimethyl-9-{2-[(S)-1-naphthalen-2-yl-ethylamino]-ethyl}-1,5-dioxa-spiro[5.5]undecan-9-ol and triphosgene following a procedure analogous to that described in Step 4 of Intermediate 2; the crude product, a mixture of the title compound and 12,12-dimethyl-3-[(S)-1-naphthalen-2-yl-ethyl]-1,10,14-trioxa-3-aza-dispiro[5.2.5.2]hexadecan-2-one, obtained thereafter is treated as described in Step 10 of Intermediate 2 to convert the

Example 89

3-[(S)-1-Naphthalen-1-yl-ethyl]-1-oxa-3-aza-spiro[5.5]undecane-2,9-dione

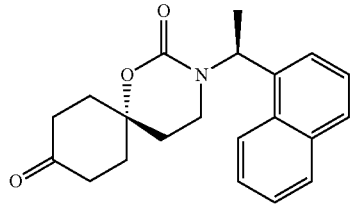

The title compound is prepared from 3,3-dimethyl-9-{2-[(S)-1-naphthalen-1-yl-ethylamino]-ethyl}-1,5-dioxa-spiro[5.5]undecan-9-ol and triphosgene following a procedure analogous to that described in Step 4 of Intermediate 2; the crude product, a mixture of the title compound and 12,12-dimethyl-3-[(S)-1-naphthalen-1-yl-ethyl]-1,10,14-trioxa-3-aza-dispiro[5.2.5.2]hexadecan-2-one, obtained thereafter is treated as described in Step 10 of Intermediate 2 to convert the intermediate to the title compound as well. Yield: 62% of theory; LC (method 6): $t_R$=1.33 min; Mass spectrum (ESI$^+$): m/z=338 [M+H]$^+$.

Example 90

3-[(S)-1-(3-Methoxy-phenyl)-ethyl]-1-oxa-3-aza-spiro[5.5]undecane-2,9-dione

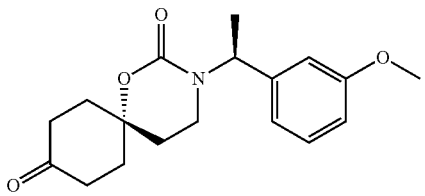

The title compound is prepared from 9-{2-[(S)-1-(3-methoxy-phenyl)-ethylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(3-methoxy-phenyl)-ethyl]-12,12-dimethyl-1,10,14-trioxa-3-aza-dispiro[5.2.5.2]hexadecan-2-one, obtained thereafter is treated as described in Step 10 of Intermediate 2 to convert the intermediate to the title compound as well. Yield: 41% of theory; LC (method 6): $t_R$=1.11 min; Mass spectrum (ESI$^+$): m/z=318 [M+H]$^+$.

Example 91

3-[(S)-Indan-1-yl]-1-oxa-3-aza-spiro[5.5]undecane-2,9-dione

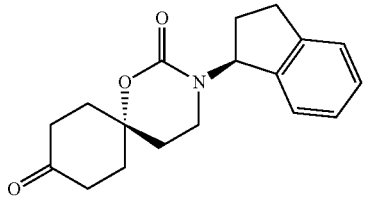

The title compound is prepared from 9-{2-[(S)-indan-1-ylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-indan-1-yl]-12,12-dimethyl-1,10,14-trioxa-3-aza-dispiro[5.2.5.2]hexadecan-2-one, obtained thereafter is treated as described in Step 10 of Intermediate 2 to convert the intermediate to the title compound as well. Yield: 44% of theory; LC (method 6): $t_R$=1.16 min; Mass spectrum (ESI$^+$): m/z=300 [M+H]$^+$.

Example 92

3-[(S)-1-b-Tolyl-propyl]-1-oxa-3-aza-spiro[5.5]undecane-2,9-dione

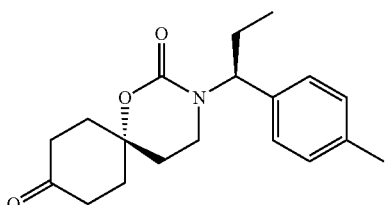

The title compound is prepared from 3,3-dimethyl-9-{2-[(S)-1-p-tolyl-propylamino]-ethyl}-1,5-dioxa-spiro[5.5]undecan-9-ol and triphosgene following a procedure analogous to that described in Step 4 of Intermediate 2; the crude product, a mixture of the title compound and 12,12-dimethyl-3-[(S)-1-p-tolyl-propyl]-1,10,14-trioxa-3-aza-dispiro[5.2.5.2] hexadecan-2-one, obtained thereafter is treated as described in Step 10 of Intermediate 2 to convert the intermediate to the title compound as well. Yield: 71% of theory; LC (method 7): $t_R$=1.37 min; Mass spectrum (ESI$^+$): m/z=316 [M+H]$^+$; $^1$H NMR (400 MHz, DMSO-d$_6$) δ 0.89 (t, J=7.2 Hz, 3H), 1.75-2.01 (m, 7H), 2.03-2.12 (m, 1H), 2.14-2.27 (m, 2H), 2.29 (s, 3H), 2.42-2.54 (m, 2H), 2.72-2.80 (m, 1H), 3.13-3.22 (m, 1H), 5.27 (dd, J=9.4, 6.8 Hz, 1H), 7.15-7.24 (m, 4H).

Example 93

3-[1-(4-Bromo-phenyl)-cyclopropyl]-1-oxa-3-aza-spiro[5.5]undecane-2,9-dione

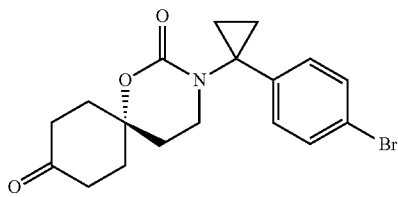

The title compound is prepared from 9-{2-[1-(4-bromo-phenyl)-cyclopropylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[1-(4-bromo-phenyl)-cyclopropyl]-12,12-dimethyl-1,10,14-tri-oxa-3-aza-dispiro[5.2.5.2]hexadecan-2-one, obtained thereafter is treated as described in Step 10 of Intermediate 2 to convert the intermediate to the title compound as well. Yield: 19% of theory; LC (method 7): $t_R$=1.37 min; Mass spectrum (ESI$^+$): m/z=378/380 (Br) [M+H]$^+$.

Examples 94 and 95 trans-9-Hydroxy-3-[(S)-1-naphthalen-2-yl-ethyl]-1-oxa-3-aza-spiro[5.5]undecan-2-one (94) and cis-9-Hydroxy-3-[(S)-1-naphthalen-2-yl-ethyl]-1-oxa-3-aza-spiro[5.5]undecan-2-one (95)

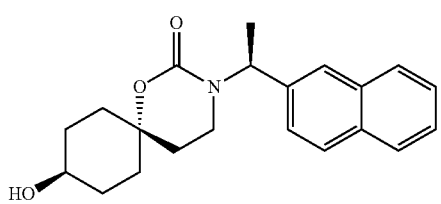

94

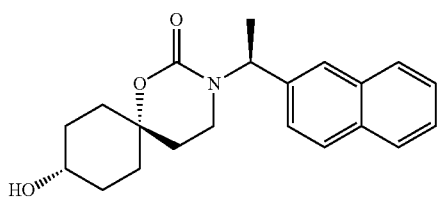

95

The title compounds are prepared from 3-[(S)-1-naphthalen-2-yl-ethyl]-1-oxa-3-aza-spiro[5.5]undecane-2,9-dione following a procedure analogous to that described in Example 22 and separated by HPLC on reversed phase (column: Stablebond C18; eluent: acetonitrile/water containing 1.36% trifluoroacetic acid).

trans-9-Hydroxy-3-[(S)-1-naphthalen-2-yl-ethyl]-1-oxa-3-aza-spiro[5.5]undecan-2-one (94): Yield: 18% of theory; LC (method 8): $t_R$=1.34 min; Mass spectrum (ESI$^+$): m/z=340 [M+H]$^+$.

cis-9-Hydroxy-3-[(S)-1-naphthalen-2-yl-ethyl]-1-oxa-3-aza-spiro[5.5]undecan-2-one (95): Yield: 35% of theory; LC (method 8): $t_R$=1.38 min; Mass spectrum (ESI$^+$): m/z=340 [M+H]$^+$.

Examples 96 and 97 trans-9-Hydroxy-(S)-3-indan-1-yl-1-oxa-3-aza-spiro[5.5]undecan-2-one (96) and cis-9-Hydroxy-(S)-3-indan-1-yl-1-oxa-3-aza-spiro[5.5]undecan-2-one (97)

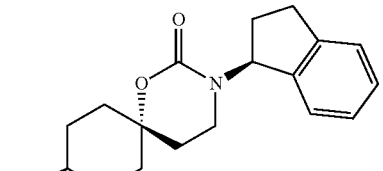

96

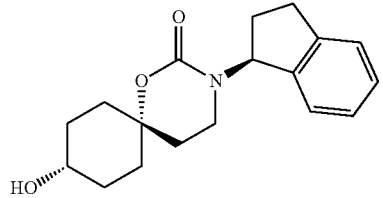

97

The title compounds are prepared from (S)-3-indan-1-yl-1-oxa-3-aza-spiro[5.5]undecane-2,9-dione following a procedure analogous to that described in Example 22 and separated by HPLC on reversed phase (column: Stablebond C18; eluent: acetonitrile/water containing 1.36% trifluoroacetic acid).

trans-9-Hydroxy-(S)-3-indan-1-yl-1-oxa-3-aza-spiro[5.5]undecan-2-one (96): Yield: 27% of theory; LC (method 8): $t_R$=1.17 min; Mass spectrum (ESI$^+$): m/z=302 [M+H]$^+$.

cis-9-Hydroxy-(S)-3-indan-1-yl-1-oxa-3-aza-spiro[5.5]undecan-2-one (97): Yield: 31% of theory; LC (method 8): $t_R$=1.22 min; Mass spectrum (ESI$^+$): m/z=302 [M+H]$^+$.

Examples 98 and 99 trans-9-Hydroxy-3-[(S)-1-phenyl-ethyl]-1-oxa-3-aza-spiro[5.5]undecan-2-one (98) and cis-9-Hydroxy-3-[(S)-1-phenyl-ethyl]-1-oxa-3-aza-spiro[5.5]undecan-2-one (99)

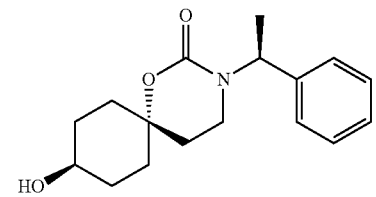

98

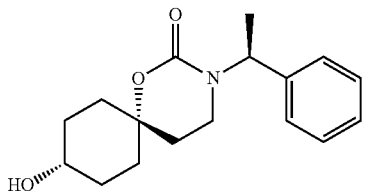

99

The title compounds are prepared from 3-[(S)-1-phenyl-ethyl]-1-oxa-3-aza-spiro[5.5]undecane-2,9-dione following a procedure analogous to that described in Example 22 and separated by HPLC on reversed phase (column: Stablebond C18; eluent: acetonitrile/water containing 1.36% trifluoroacetic acid).

trans-9-Hydroxy-3-(1-phenyl-ethyl)-1-oxa-3-aza-spiro[5.5]undecan-2-one (98): Yield: 18% of theory; LC (method 8): $t_R$=1.10 min; Mass spectrum (ESI$^+$): m/z=290 [M+H]$^+$.

cis-9-Hydroxy-3-(1-phenyl-ethyl)-1-oxa-3-aza-spiro[5.5]undecan-2-one (99): Yield: 25% of theory; LC (method 8): $t_R$=1.16 min; Mass spectrum (ESI$^+$): m/z=290 [M+H]$^+$.

Examples 100 and 101 trans-9-Hydroxy-3-[(S)-1-(3-methoxy-phenyl)-ethyl]-1-oxa-3-aza-spiro[5.5]undecan-2-one (100) and cis-9-Hydroxy-3-[(S)-1-(3-methoxy-phenyl)-ethyl]-1-oxa-3-aza-spiro[5.5]undecan-2-one (101)

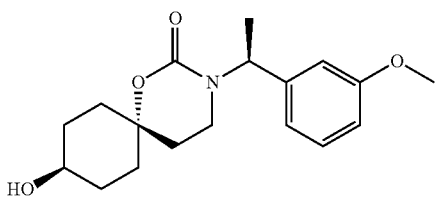

100

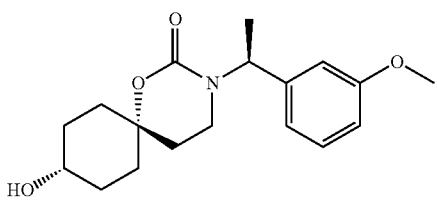

101

The title compounds are prepared from 3-[(S)-1-(3-methoxy-phenyl)-ethyl]-1-oxa-3-aza-spiro[5.5]undecane-2,9-dione following a procedure analogous to that described in Example 22 and separated by HPLC on reversed phase (column: Stablebond C18; eluent: acetonitrile/water containing 1.36% trifluoroacetic acid).

trans-9-Hydroxy-3-[(S)-1-(3-methoxy-phenyl)-ethyl]-1-oxa-3-aza-spiro[5.5]undecan-2-one (100): Yield: 23% of theory; LC (method 8): $t_R$=1.11 min; Mass spectrum (ESI$^+$): m/z=320 [m+H]$^+$.

cis-9-Hydroxy-3-[(S)-1-(3-methoxy-phenyl)-ethyl]-1-oxa-3-aza-spiro[5.5]undecan-2-one (101): Yield: 16% of theory; LC (method 8): $t_R$=1.16 min; Mass spectrum (ESI$^+$): m/z=320 [m+H]$^+$.

Examples 102 and 103 trans-9-Hydroxy-3-[(S)-1-naphthalen-1-yl-ethyl]-1-oxa-3-aza-spiro[5.5]undecan-2-one (102) and cis-9-Hydroxy-3-[(S)-1-naphthalen-1-yl-ethyl]-1-oxa-3-aza-spiro[5.5]undecan-2-one (103)

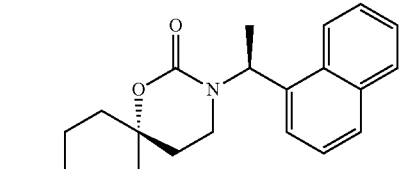

102

103

The title compounds are prepared from 3-[(S)-1-naphthalen-1-yl-ethyl]-1-oxa-3-aza-spiro[5.5]undecane-2,9-dione following a procedure analogous to that described in Example 22. Separation by HPLC on reversed phase (column: Stablebond C18; eluent: acetonitrile/water containing 1.36% trifluoroacetic acid) afforded a pure fraction of compound 102.

trans-9-Hydroxy-3-[(S)-1-naphthalen-1-yl-ethyl]-1-oxa-3-aza-spiro[5.5]undecan-2-one (102): Yield: 3% of theory; LC (method 8): $t_R$=1.32 min; Mass spectrum (ESI$^+$): m/z=340 [M+H]$^+$.

Example 104

3-[(S)-1-(4-Difluoromethyl-phenyl)-ethyl]-1-oxa-3-aza-spiro[5.5]undecane-2,9-dione

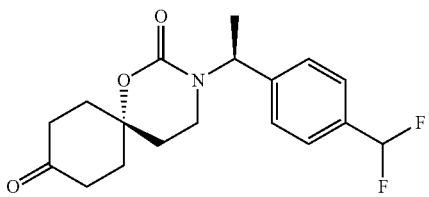

The title compound is prepared from 9-{2-[(S)-1-(4-difluoromethyl-phenyl)-ethylamino]-ethyl}-3,3-dimethyl-1,5-dioxa-spiro[5.5]undecan-9-ol and triphosgene following a procedure analogous to that described in Step 4 of Intermediate 2; the crude product, a mixture of the title compound and 3-[(S)-1-(4-difluoromethyl-phenyl)-ethyl]-12,12-dimethyl-1,10,14-trioxa-3-aza-dispiro[5.2.5.2]hexadecan-2-one, obtained thereafter is treated as described in Step 10 of Intermediate 2 to convert the intermediate to the title compound as well. Yield: 58% of theory; LC (method 8): $t_R$=1.10 min; Mass spectrum (ESI$^+$): m/z=338 [M+H]$^+$.

Examples 105 and 106

3-[(S)-1-(4-Difluoromethyl-phenyl)-ethyl]-trans-9-hydroxy-1-oxa-3-aza-spiro[5.5]undecan-2-one (105) and 3-[(S)-1-(4-Difluoromethyl-phenyl)-ethyl]-cis-9-hydroxy-1-oxa-3-aza-spiro[5.5]undecan-2-one (106)

105

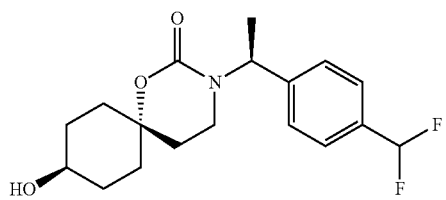

106

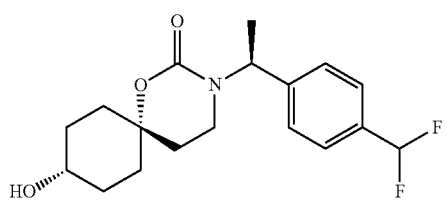

The title compounds are prepared from 3-[(S)-1-(4-difluoromethyl-phenyl)-ethyl]-1-oxa-3-aza-spiro[5.5]undecane-2,9-dione following a procedure analogous to that described in Example 22 and separated by HPLC on reversed phase (column: Stablebond C18; eluent: acetonitrile/water containing 1.36% trifluoroacetic acid).

3-[(S)-1-(4-Difluoromethyl-phenyl)-ethyl]-trans-9-hydroxy-1-oxa-3-aza-spiro[5.5]undecan-2-one (105): Yield: 45% of theory; LC (method 8): $t_R$=1.11 min; Mass spectrum (ESI$^+$): m/z=340 [M+H]$^+$.

3-[(S)-1-(4-Difluoromethyl-phenyl)-ethyl]-cis-9-hydroxy-1-oxa-3-aza-spiro[5.5]undecan-2-one (106): Yield: 9% of theory; LC (method 8): $t_R$=1.15 min; Mass spectrum (ESI$^+$): m/z=340 [M+H]$^+$.

Example 107

3-[(S)-1-(4-Bromo-phenyl)-ethyl]-cis-8-hydroxy-1-oxa-3-aza-spiro[5.5]undecan-2-one

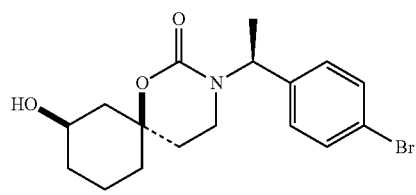

The title compound is prepared from 1-{2-[(S)-1-(4-bromo-phenyl)-ethylamino]-ethyl}-cis-3-(tert-butyl-dimethyl-silanyloxy)-cyclohexanol and triphosgene following a procedure analogous to that described in Step 4 of Intermediate 2. Yield: 14% of theory; LC (method 8): $t_R$=1.34 min; Mass spectrum (ESI$^+$): m/z=368/370 (Br) [M+H]$^+$.

Example 108

3-[(S)-1-(4-Bromo-phenyl)-ethyl]-trans-8-hydroxy-1-oxa-3-aza-spiro[5.5]undecan-2-one

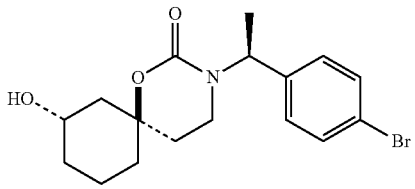

The title compound is prepared from 1-{2-[(S)-1-(4-bromo-phenyl)-ethylamino]-ethyl}-trans-3-(tert-butyl-dimethyl-silanyloxy)-cyclohexanol and triphosgene following a procedure analogous to that described in Step 4 of Intermediate 2. Yield: 17% of theory; LC (method 8): $t_R$=1.36 min; Mass spectrum (ESI$^+$): m/z=368/370 (Br) [M+H]$^+$.

Example 109

3-[1(S)-1-(2-Chloro-phenyl)-ethyl]-1-oxa-3-aza-spiro[5.5]undecane-2,9-dione

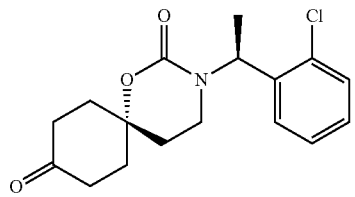

The title compound is prepared from 9-{2-[(S)-1-(2-chloro-phenyl)-ethylamino]-ethyl}-3,3-dimethyl-2,4-dioxa-spiro[5.5]undecan-9-ol and triphosgene following a procedure analogous to that described in Step 4 of Intermediate 2; the crude product, a mixture of the title compound and 3-[(S)-1-(2-chloro-phenyl)-ethyl]-12,12-dimethyl-1,10,14-trioxa-3-aza-dispiro[5.2.5.2]hexadecan-2-one, obtained thereafter is treated as described in Step 10 of Intermediate 2 to convert the intermediate to the title compound as well. Yield: 43% of theory; LC (method 8): $t_R$=1.15 min; Mass spectrum (ESI$^+$): m/z=322/324 (Cl) [M+H]$^+$.

Examples 110 and 111

3-[1-(4-Chloro-phenyl)-propyl]-trans-9-hydroxy-1-oxa-3-aza-spiro[5.5]undecan-2-one (110) and 3-[1-(4-Chloro-phenyl)-propyl]-cis-9-hydroxy-1-oxa-3-aza-spiro[5.5]undecan-2-one (111)

110

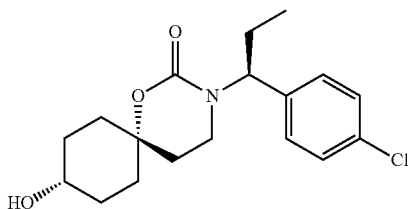

111

The title compounds are prepared from 3-[(S)-1-(4-chloro-phenyl)-propyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-1-(4-Chloro-phenyl)-propyl]-trans-9-hydroxy-1-oxa-3-aza-spiro[5.5]undecan-2-one (110): Yield: 31% of theory; LC (method 8): $t_R$=1.33 min; Mass spectrum (ESI$^+$): m/z=338/340 (Cl) [M+H]$^+$.

3-[(S)-1-(4-Chloro-phenyl)-propyl]-cis-9-hydroxy-1-oxa-3-aza-spiro[5.5]undecan-2-one (111): Yield: 29% of theory; LC (method 8): $t_R$=1.37 min; Mass spectrum (ESI$^+$): m/z=338/340 (Cl) [M+H]$^+$.

Example 112

3-[(S)-1-Phenyl-propyl]-1-oxa-3-aza-spiro[5.5]undecane-2,9-dione

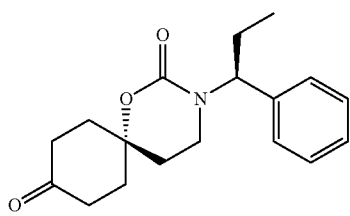

The title compound is prepared from 3,3-dimethyl-9-{2-[(S)-1-phenyl-propylamino]-ethyl}-2,4-dioxa-spiro[5.5]undecan-9-ol and triphosgene following a procedure analogous to that described in Step 4 of Intermediate 2; the crude product, a mixture of the title compound and 12,12-dimethyl-3-[(S)-1-phenyl-propyl]-1,11,13-trioxa-3-aza-dispiro[5.2.5.2]hexadecan-2-one, obtained thereafter is treated as described in Step 10 of Intermediate 2 to convert the intermediate to the title compound as well. Yield: 56% of theory; LC (method 8): $t_R$=1.20 min; Mass spectrum (ESI$^+$): m/z=302 [M+H]$^+$.

Examples 113 and 114

3-[(S)-1-(4-tert-Butyl-phenyl)-ethyl]-trans-9-hydroxy-1-oxa-3-aza-spiro[5.5]undecan-2-one (113) and 3-[(S)-1-(4-tert-Butyl-phenyl)-ethyl]-cis-9-hydroxy-1-oxa-3-aza-spiro[5.5]undecan-2-one (114)

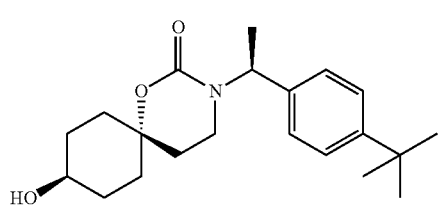

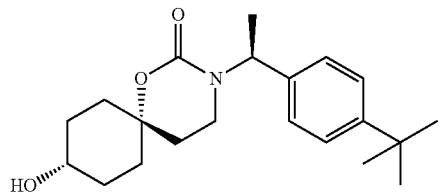

The title compounds are prepared from 3-[(S)-1-(4-tert-Butyl-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[(S)-1-(4-tert-Butyl-phenyl)-ethyl]-trans-9-hydroxy-1-oxa-3-aza-spiro[5.5]undecan-2-one (113): Yield: 38% of theory; LC (method 8): $t_R$=1.50 min; Mass spectrum (ESI$^+$): m/z=346 [m+H]$^+$.

3-[(S)-1-(4-tert-Butyl-phenyl)-ethyl]-cis-9-hydroxy-1-oxa-3-aza-spiro[5.5]undecan-2-one (114): Yield: 28% of theory; LC (method 8): $t_R$=1.53 min; Mass spectrum (ESI$^+$): m/z=346 [m+H]$^+$.

Examples 115 and 116 trans-9-Hydroxy-3-[(S)-1-(4-trifluoromethoxy-phenyl)-ethyl]-1-oxa-3-aza-spiro[5.5]undecan-2-one (115) and cis-9-Hydroxy-3-[(S)-1-(4-trifluoromethoxy-phenyl)-ethyl]-1-oxa-3-aza-spiro[5.5]undecan-2-one (116)

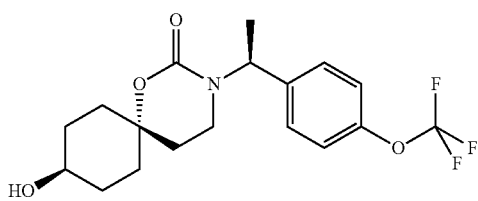

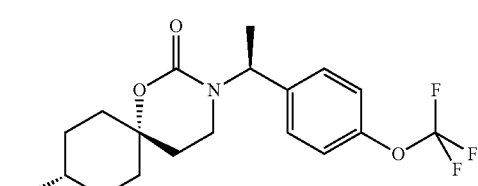

The title compounds are prepared from 3-[(S)-1-(4-trifluoromethoxy-phenyl)-ethyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

trans-9-Hydroxy-3-[(S)-1-(4-trifluoromethoxy-phenyl)-ethyl]-1-oxa-3-aza-spiro[5.5]undecan-2-one (115): Yield: 42% of theory; LC (method 8): $t_R$=1.34 min; Mass spectrum (ESI$^+$): m/z=374 [M+H]$^+$.

cis-9-Hydroxy-3-[(S)-1-(4-trifluoromethoxy-phenyl)-ethyl]-1-oxa-3-aza-spiro[5.5]undecan-2-one (116): Yield: 44% of theory; LC (method 8): $t_R$=1.37 min; Mass spectrum (ESI$^+$): m/z=374 [M+H]$^+$.

Example 117

3-[(S)-1-o-Tolyl-ethyl]-1-oxa-3-aza-spiro[5.5]undecane-2,9-dione

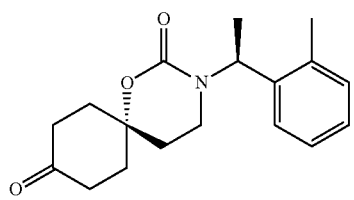

The title compound is prepared from 3,3-dimethyl-9-{2-[(S)-1-o-tolyl-ethylamino]-ethyl}-1,5-dioxa-spiro[5.5]undecan-9-ol and triphosgene following a procedure analogous to that described in Step 4 of Intermediate 2; the crude product, a mixture of the title compound and 12,12-di methyl-3-[(S)-1-o-tolyl-ethyl]-1,10,14-trioxa-3-aza-dispiro[5.2.5.2]hexadecan-2-one, obtained thereafter is treated as described in Step 10 of Intermediate 2 to convert the intermediate to the title compound as well. Yield: 17% of theory; LC (method 8): $t_R$=1.23 min; Mass spectrum (ESI$^+$): m/z=302 [M+H]$^+$.

Examples 118 and 119

3-[(S)-1-(2-Chloro-phenyl)-ethyl]-trans-9-hydroxy-1-oxa-3-aza-spiro[5.5]undecan-2-one (118) and 3-[(S)-1-(2-Chloro-phenyl)-ethyl]-cis-9-hydroxy-1-oxa-3-aza-spiro[5.5]undecan-2-one (119)

118
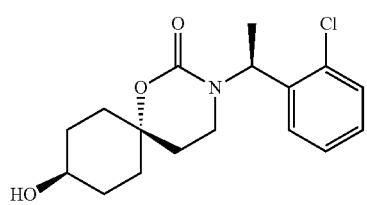

119
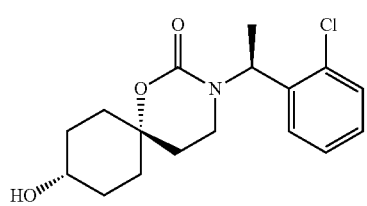

The title compounds are prepared from 3-[(S)-1-(2-chloro-phenyl)-ethyl]-1-oxa-3-aza-spiro[5.5]undecane-2,9-dione following a procedure analogous to that described in Example 22 and separated by HPLC on reversed phase (column: Stablebond C18; eluent: acetonitrile/water containing 1.36% trifluoroacetic acid).

3-[(S)-1-(2-Chloro-phenyl)-ethyl]-trans-9-hydroxy-1-oxa-3-aza-spiro[5.5]undecan-2-one (118): Yield: 26% of theory; LC (method 8): $t_R$=1.15 min; Mass spectrum (ESI$^+$): m/z=324 [m+H]$^+$.

3-[(S)-1-(2-Chloro-phenyl)-ethyl]-cis-9-hydroxy-1-oxa-3-aza-spiro[5.5]undecan-2-one (119): Yield: 24% of theory; LC (method 8): $t_R$=1.19 min; Mass spectrum (ESI$^+$): m/z=324 [M+H]$^+$.

Examples 120 and 121 trans-9-Hydroxy-3-[(S)-1-(4-methoxy-phenyl)-propyl]-1-oxa-3-aza-spiro[5.5]undecan-2-one (120) and cis-9-Hydroxy-3-[(S)-1-(4-methoxy-phenyl)-propyl]-1-oxa-3-aza-spiro[5.5]undecan-2-one (121)

120
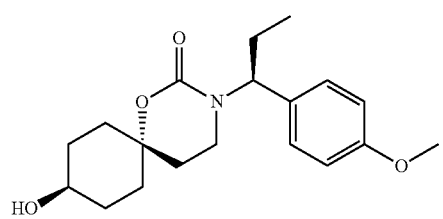

121
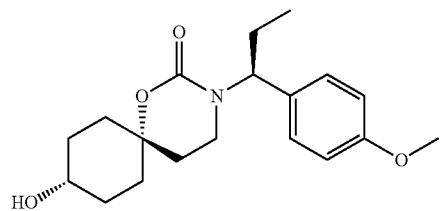

The title compounds are prepared from 3-[(S)-1-(4-methoxy-phenyl)-propyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

trans-9-Hydroxy-3-[(S)-1-(4-methoxy-phenyl)-propyl]-1-oxa-3-aza-spiro[5.5]undecan-2-one (120): Yield: 34% of theory; LC (method 7): $t_R$=1.26 min; Mass spectrum (ESI$^+$): m/z=334 [M+H]$^+$.

cis-9-Hydroxy-3-[(S)-1-(4-methoxy-phenyl)-propyl]-1-oxa-3-aza-spiro[5.5]undecan-2-one (121): Yield: 35% of theory; LC (method 7): $t_R$=1.31 min; Mass spectrum (ESI$^+$): m/z=334 [m+H]$^+$.

Examples 122 and 123 trans-9-Hydroxy-3-[(S)-1-p-tolyl-propyl]-1-oxa-3-aza-spiro[5.5]undecan-2-one (122) and cis-9-Hydroxy-3-[(S)-1-p-tolyl-propyl]-1-oxa-3-aza-spiro[5.5]undecan-2-one (123)

122
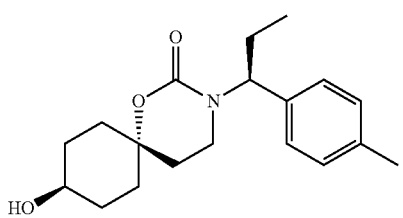

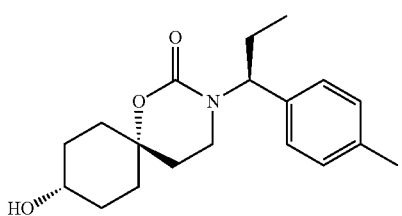

The title compounds are prepared from 3-[(S)-1-p-tolyl-propyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

trans-9-Hydroxy-3-[(S)-1-p-tolyl-propyl]-1-oxa-3-aza-spiro[5.5]undecan-2-one (122): LC (method 8): $t_R$=1.31 min; Mass spectrum (ESI$^+$): m/z=318 [M+H]$^+$.

cis-9-Hydroxy-3-[(S)-1-p-tolyl-propyl]-1-oxa-3-aza-spiro[5.5]undecan-2-one (123): LC (method 8): $t_R$=1.35 min; Mass spectrum (ESI$^+$): m/z=318 [M+H]$^+$.

Examples 124 and 125

3-[1-(4-Bromo-phenyl)-cyclopropyl]-trans-9-hydroxy-1-oxa-3-aza-spiro[5.5]undecan-2-one (124) and 3-[1-(4-Bromo-phenyl)-cyclopropyl]-cis-9-hydroxy-1-oxa-3-aza-spiro[5.5]undecan-2-one (125)

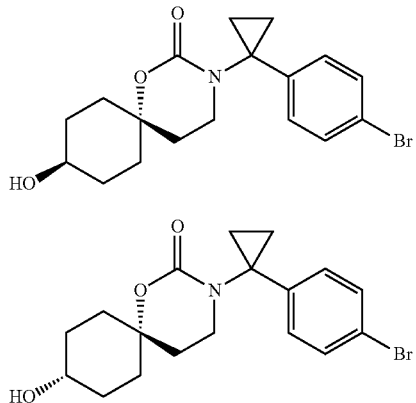

The title compounds are prepared from 3-[1-(4-bromophenyl)-cyclopropyl]-1-oxa-3-aza-spiro[5.5]undecane-2,9-dione following a procedure analogous to that described in Example 22 and separated by SFC on chiral phase (column: Daicel IC, 250×4.6 mm, 5 μm; eluent: methanol containing 0.2% diethylamine/sc carbon dioxide 30:70; flow: 4 mL/min).

3-[1-(4-Bromo-phenyl)-cyclopropyl]-trans-9-hydroxy-1-oxa-3-aza-spiro[5.5]undecan-2-one (124): Yield: 30% of theory; LC (column: Daicel IC, 250×4.6 mm, 5 μm; eluent: methanol containing 0.2% diethylamine/sc carbon dioxide 30:70; flow: 4 mL/min): $t_R$=3.14 min; Mass spectrum (ESI$^+$): m/z=380/382 (Br) [M+H]$^+$.

3-[1-(4-Bromo-phenyl)-cyclopropyl]-cis-9-hydroxy-1-oxa-3-aza-spiro[5.5]undecan-2-one (125): Yield: 29% of theory; LC (column: Daicel IC, 250×4.6 mm, 5 μm; eluent: methanol containing 0.2% diethylamine/sc carbon dioxide 30:70; flow: 4 mL/min): $t_R$=8.20 min; Mass spectrum (ESI$^+$): m/z=380/382 (Br) [M+H]$^+$.

Examples 126 and 127 trans-9-Hydroxy-3-[(S)-1-phenyl-propyl]-1-oxa-3-aza-spiro[5.5]undecan-2-one (126) and cis-9-Hydroxy-3-[(S)-1-phenyl-propyl]-1-oxa-3-aza-spiro[5.5]undecan-2-one (127)

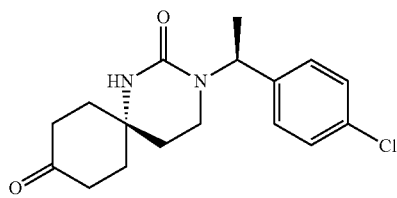

The title compounds are prepared from 3-[(S)-1-phenyl-propyl]-1-oxa-3-aza-spiro[5.5]undecane-2,9-dione following a procedure analogous to that described in Example 22 and separated by HPLC on reversed phase (column: Stablebond C18; eluent: acetonitrile/water containing 1.36% trifluoroacetic acid).

trans-9-Hydroxy-3-[(S)-1-phenyl-propyl]-1-oxa-3-aza-spiro[5.5]undecan-2-one (126): Yield: 10% of theory; LC (method 8): $t_R$=1.21 min; Mass spectrum (ESI$^+$): m/z=304 [M+H]$^+$.

cis-9-Hydroxy-3-[(S)-1-phenyl-propyl]-1-oxa-3-aza-spiro[5.5]undecan-2-one (127): Yield: 15% of theory; LC (method 8): $t_R$=1.25 min; Mass spectrum (ESI$^+$): m/z=304 [M+H]$^+$.

Example 128

3-[(S)-1-(4-Chloro-phenyl)-ethyl]-1,3-diaza-spiro[5.5]undecane-2,9-dione

The title compound is prepared from 11-[(S)-1-(4-chloro-phenyl)-ethyl]-1,4-dioxa-9,11-diaza-dispiro[4.2.5.2]pentadecan-10-one following a procedure analogous to that described in Step 10 of Intermediate 2. Yield: 23% of theory; LC (method 8): $t_R$=1.29 min; Mass spectrum (ESI$^+$): m/z=321 [M+H]$^+$.

Examples 129 and 130 trans-3-[(S)-1-(4-Chloro-phenyl)-ethyl]-9-hydroxy-1,3-diaza-spiro[5.5]undecan-2-one (129) and cis-3-[(S)-1-(4-Chloro-phenyl)-ethyl]-9-hydroxy-1,3-diaza-spiro[5.5]undecan-2-one (130)

129

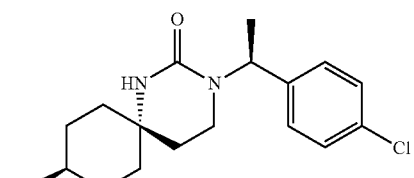

130

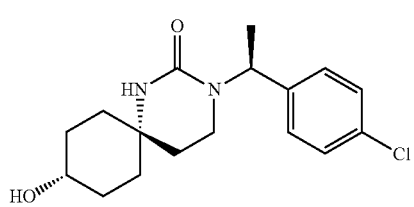

The title compounds are prepared from 3-[(S)-1-(4-chloro-phenyl)-ethyl]-1,3-diaza-spiro[5.5]undecane-2,9-dione following a procedure analogous to that described in Example 22 and separated by HPLC on reversed phase (column: Xbridge; eluent: methanol/water containing 0.125% ammonia); spatial orientation of the hydroxy group, cis or trans, is arbitrarily assigned.

trans-3-[(S)-1-(4-Chloro-phenyl)-ethyl]-9-hydroxy-1,3-diaza-spiro[5.5]undecan-2-one (129): Yield: 16% of theory; LC (method 8): $t_R$=1.27 min; Mass spectrum (ESI$^+$): m/z=323 [M+H]$^+$.

cis-3-[(S)-1-(4-Chloro-phenyl)-ethyl]-9-hydroxy-1,3-diaza-spiro[5.5]undecan-2-one (130): Yield: 16% of theory; LC (method 8): $t_R$=1.38 min; Mass spectrum (ESI$^+$): m/z=323 [M+H]$^+$.

Some examples of formulations will now be described in which the term "active substance" denotes one or more compounds according to the invention, including the salts thereof. In the case of one of the combinations with one or additional active substances as described previously, the term "active substance" also includes the additional active substances.

Example A

Tablets Containing 100 mg of Active Substance

Composition:
1 tablet contains:

| active substance | 100.0 mg |
|---|---|
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

Example B

Tablets Containing 150 mg of Active Substance

Composition:
1 tablet contains:

| active substance | 150.0 mg |
|---|---|
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

Example C

Hard Gelatine Capsules Containing 150 mg of Active Substance

Composition:
1 capsule contains:

| active substance | 150.0 mg |
|---|---|
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

Example D

Suppositories Containing 150 mg of Active Substance

Composition:
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules containing 10 MC1 active substance

Composition:

| | |
|---|---|
| active substance | 10.0 mg |
| 0.01N hydrochloric acid | q.s. |
| double-distilled water | ad 2.0 mL |

Preparation:

The active substance is dissolved in the necessary amount of 0.01 N HCl, made isotonic with common salt, filtered sterile and transferred into 2 mL ampoules.

Example F

Ampoules Containing 50 mg of Active Substance

Composition:

| | |
|---|---|
| active substance | 50.0 mg |
| 0.01N hydrochloric acid | q.s. |
| double-distilled water | ad 10.0 mL |

Preparation:

The active substance is dissolved in the necessary amount of 0.01 N HCl, made isotonic with common salt, filtered sterile and transferred into 10 mL ampoules.

What is claimed is:

1. A compound of formula I

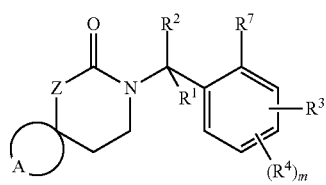

wherein $R^1$ is selected from the group consisting of
$C_{1-4}$-alkyl-, $HF_2C$—, $F_3C$— and $C_{3-4}$-cycloalkyl-, $R^2$ is selected from the group consisting of
H and $C_{1-4}$-alkyl-,
wherein above mentioned $C_{1-4}$-alkyl-group may optionally be substituted with one to three F, or, $R^1$ and $R^2$ form together a $C_{2-5}$-alkylene bridge,
wherein, in case the before mentioned alkylene group contains more than 2-$CH_2$— groups, one —$CH_2$— group may optionally be replaced by —O—;

$R^3$ is selected from the group $R^{3a}$ consisting of

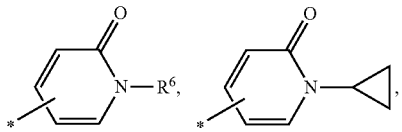

H, F, phenyl, naphthyl, pyrrolyl, furanyl, thienyl, tetrazolyl, pyridyl, indolyl, benzofuranyl, benzothiophenyl, quinolinyl, isoquinolinyl,
wherein in the pyrrolyl, furanyl, thienyl, and pyridyl group 1 or 2 CH groups optionally may be replaced by N, and wherein in the indolyl, benzofuranyl, benzothiophenyl, quinolinyl, and isoquinolinyl group 1 to 3 CH groups optionally may be replaced by N, and
wherein all above-mentioned groups may optionally be substituted with one or two $R^{10}$ which may be identical or different, $R^4$ is selected independently of each other from the group $R^{4a}$ consisting of
H, halogen, $C_{1-6}$-alkyl-, $C_{3-6}$-cycloalkyl-, HO—, $C_{1-4}$-alkyl-O—, HO—$C_{2-4}$-alkyl-O—, $H_3CO$—$C_{2-4}$-alkyl-O—, NC—$C_{1-4}$-alkyl-O—, $C_{3-6}$-cycloalkyl-O—, tetrahydrofuranyl, tetrahydrofuranyl-O—, tetrahydropyranyl-, tetrahydropyranyl-O—, NC—, HOOC—, $C_{1-4}$-alkyl-OC(O)—, $(R^6)_2N$—C(O)—, $C_{1-4}$-alkyl-S—, $C_{1-4}$-alkyl-S(O)— and $C_{1-4}$-alkyl-S(O)$_2$—,
wherein above mentioned $C_{1-6}$-alkyl-, $C_{1-4}$-alkyl-O— and $C_{3-6}$-cycloalkyl-groups may optionally be substituted with one to three F, and
wherein above mentioned $C_{1-6}$-alkyl- and $C_{3-6}$-cycloalkyl-groups may optionally be monosubstituted with HO—, $H_3CO$—, NC—, HOOC—, $C_{1-4}$-alkyl-OC(O)—, $(R^6)_2N$—C(O)—, $C_{1-4}$-alkyl-S—, $C_{1-4}$-alkyl-S(O)— or $C_{1-4}$-alkyl-S(O)$_2$—,
and
wherein two of the aforementioned groups $R^{4a}$, provided that they are attached to adjacent carbon atoms of the phenyl ring in formula I may form together a $C_{3-5}$-alkylene bridge,
wherein one or two —$CH_2$-groups of the aforementioned $C_{3-5}$-alkylene bridge may optionally be replaced by any of the groups selected form —N($R^N$)—, —O—, and —C(O)—, and
which may optionally be substituted with one or two groups independently selected from F and $H_3C$—,
and
wherein two of the aforementioned groups $R^{4a}$, provided that they are attached to adjacent carbon atoms of the phenyl ring in formula I may form together with the carbon atoms to which they are attached a benzo, pyrido, pyrimido, pyrazino, pyridazino, pyrazolo, imidazo, triazolo, oxazolo, thiazolo, isoxazolo, or isothiazolo ring,
wherein each of the aforementioned benzo, pyrido, pyrimido, pyrazino, pyridazino, pyrazolo, imidazo, triazolo, oxazolo, thiazolo, isoxazolo, or isothiazolo rings may optionally be substituted with one or two substituents independently from each other selected from halogen, $C_{1-4}$-alkyl-, $FH_2C$—, $F_2HC$—, $F_3C$—, $H_2N$—, $(C_{1-4}$-alkyl)$_2$ NH—, HO—, C$_{1-4}$-alkyl-O—, FH$_2$CO—, F$_2$HCO—, F$_3$CO— and NC—, A is —(CH$_2$)$_5$—(CH$_2$)$_{4-6}$—, wherein the above mentioned group may optionally be substituted with one or two R$^5$, R$^5$ is selected independently from each other from the group R$^{5a}$ consisting of halogen, NC—, (R$^6$)$_2$N—, HO—, O=, C$_{1-6}$-alkyl-, C$_{3-6}$-cycloalkyl-, C$_{2-6}$-alkenyl-, C$_{2-6}$-alkynyl-, HOOC—, C$_{1-4}$-alkyl-OC(O)—, (R$^6$)$_2$N—C(O)—, C$_{1-4}$-alkyl-S—, C$_{1-4}$-alkyl-S(O)— and C$_{1-4}$-alkyl-S(O)$_2$—, wherein the C$_{1-6}$-alkyl- and C$_{3-6}$-cycloalkyl-, C$_{2-6}$-alkenyl and C$_{2-6}$-alkynyl-groups may optionally be substituted independently from each other by one to three F and/or one substituent selected from the group consisting of F, Cl, NC—, (R$^6$)$_2$N—, HO—, O=, C$_{1-4}$-alkyl-, HOOC—, C$_{1-4}$-alkyl-OC(O)—, (R$^6$)$_2$N—C(O)—, C$_{1-4}$-alkyl-S—, C$_{1-4}$-alkyl-S(O)— and C$_{1-4}$-alkyl-S(O)$_2$—, and wherein two of the aforementioned groups R$^{5a}$ may form together a —(CH$_2$)$_{4-6}$-alkylene bridge, wherein the aforementioned —(CH$_2$)$_{4-6}$-alkylene bridge may optionally be substituted with one or two groups selected independently from each other from the group consisting of F, H$_3$C—, HO—, and H$_3$C—O—, and wherein one or two —CH$_2$— groups of said (CH$_2$)$_{4-6}$-alkylene bridge may optionally be replaced by —O—, R$^6$ is selected independently of each other from the group R$^{6a}$ consisting of H and C$_{1-4}$-alkyl-, R$^7$ is selected from the group R$^{7a}$ consisting of H, halogen, C$_{1-4}$-alkyl-, F$_3$C—, HO—, C$_{1-4}$-alkyl-O—, and NC—, or the aforementioned group R$^{7a}$ may form together with R$^1$ a —(CH$_2$)$_{2-4}$-alkylene bridge, wherein the aforementioned —(CH$_2$)$_{2-4}$-alkylene bridge may optionally be substituted with one or two groups selected independently from each other from the group consisting of F, H$_3$C—, HO—, and H$_3$C—O—, and wherein one —CH$_2$— group may optionally be replaced by —O—, R$^{10}$ is selected independently of each other from the group R$^{10a}$ consisting of halogen, C$_{1-4}$-alkyl-, C$_{3-6}$-cycloalkyl-, FH$_2$C, F$_2$HC—, F$_3$C—, NC—, H$_2$N—C(O)—, C$_{1-4}$-alkyl-NH—C(O)—, (C$_{1-4}$-alkyl)$_2$N—C(O)—, HO$_2$C—, C$_{1-4}$-alkyl-O—C(O)—, O$_2$N—, H$_2$N—, C$_{1-4}$-alkyl-NH—, (C$_{1-4}$-alkyl)$_2$N—, H$_3$CC(O)NH—, H$_3$C—S(O)$_2$—NH—, HO—, C$_{1-4}$-alkyl-O—, FH$_2$CO—, F$_2$HC—O—, F$_3$C—O—, H$_3$C—S—, H$_3$C—S(O)—, H$_3$C—S(O)$_2$—, wherein aforementioned C$_{1-4}$-alkyl- and C$_{3-6}$-cycloalkyl-groups may optionally be substituted with 1 or 2 groups selected independently from each other from the group consisting of F, H$_3$C—, H$_3$C—O—, NC—, H$_2$N—C(O)—, C$_{1-4}$-alkyl-NH—C(O)—, (C$_{1-4}$-alkyl)$_2$N—C(O)— and HO—, Z is —O—, R$^N$ is selected independently of each other from the group R$^{Na}$ consisting of H, C$_{1-6}$-alkyl-, C$_{3-6}$-cycloalkyl-, C$_{3-6}$-alkenyl-, C$_{3-6}$-alkynyl-, C$_{1-4}$-alkyl-C(O)—, C$_{3-6}$-cycloalkyl-C(O)—, H$_2$N—C(O)—, C$_{1-4}$-alkyl-NH—C(O)—, (C$_{1-4}$-alkyl)$_2$N—C(O)—, C$_{1-4}$-alkyl-O—C(O)—, C$_{1-4}$-alkyl-S(O)$_2$—, and C$_{3-6}$-cycloalkyl-S(O)$_2$—, wherein the above mentioned C$_{1-6}$-alkyl-, C$_{3-6}$-alkenyl- and C$_{3-6}$-alkynyl-groups may optionally be mono- di- or trisubstituted with fluorine, m denotes 0, 1, 2 or 3;

or a salt thereof.

2. The compound according to claim 1, wherein

R$^2$ is selected from the group R$^{2b}$ consisting of

H and H$_3$C—.

3. The compound according to claim 1, wherein

R$^3$ is selected from the group R$^{3b}$ consisting of

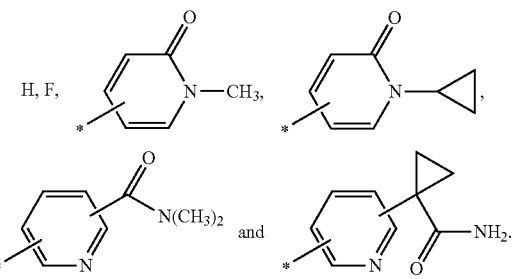

4. The compound according to claim 1, wherein

R$^4$ is selected independently of each other from the group R$^{4b}$ consisting of H, F, Cl, Br, C$_{1-4}$-alkyl-, C$_{3-5}$-cycloalkyl-, HO—, C$_{1-4}$-alkyl-O—, HO—C$_{2-4}$-alkyl-O—, H$_3$CO—C$_{2-4}$-alkyl-O—, NC—C$_{1-4}$-alkyl-O—, C$_{3-5}$-cycloalkyl-O—, tetrahydrofuranyl-O—, tetrahydropyranyl-O—, NC—, HOOC—, C$_{1-4}$-alkyl-OC(O)—, (R$^6$)$_2$N—C(O)—, C$_{1-3}$-alkyl-S—, C$_{1-3}$-alkyl-S(O)— and C$_{1-3}$-alkyl-S(O)$_2$—, wherein above mentioned C$_{1-4}$alkyl- and C$_{1-4}$-alkyl-O-groups may optionally be substituted with one to three F, and wherein above mentioned C$_{1-4}$-alkyl- and C$_{3-5}$-cycloalkyl-groups may optionally be monosubstituted with HO—, H$_3$CO—, NC—, (R$^6$)$_2$N—C(O)—, or C$_{1-3}$-alkyl-S(O)$_2$—, and wherein two of the aforementioned groups R$^{4b}$ provided that they are attached to adjacent carbon atoms of the phenyl ring in formula I may form together a C$_{3-5}$-alkylene bridge, wherein one or two —CH$_2$-groups of the aforementioned C$_{3-5}$-alkylene bridge may optionally be replaced by —O—, and which may optionally be substituted with one or two F, and wherein two of the aforementioned groups R$^{4b}$, provided that they are attached to adjacent carbon atoms of the phenyl ring in formula I may form together with the carbon atoms to which they are attached a benzo, pyrido, pyrimido, pyrazino, pyridazino, pyrazolo, imidazo, triazolo, oxazolo, thiazolo, isoxazolo or isothiazolo ring, wherein each of the aforementioned benzo, pyrido, pyrimido, pyrazino, pyridazino, pyrazolo, imidazo, triazolo, oxazolo, thiazolo, isoxazolo or isothiazolo rings may optionally be substituted with one or two substituents independently from each other selected from F, Cl, Br, $C_{1-4}$-alkyl-, $FH_2C-$, $F_2HC-$, $F_3C-$, HO—, and $C_{1-4}$-alkyl-O—, $FH_2CO-$, $F_2HCO-$, $F_3CO-$ and NC—.

5. The compound according to claim 1, wherein $R^5$ is selected independently from each other from the group $R^{5b}$ consisting of F, NC—, $(R^6)_2N-$, HO—, O=, $C_{1-6}$-alkyl-, HOOC—, $C_{1-4}$-alkyl-OC(O)—, $(R^6)_2N-C(O)-$, $C_{1-3}$-alkyl-S—, $C_{1-3}$-alkyl-S(O)— and $C_{1-3}$-alkyl-S(O)$_2-$, wherein above mentioned $C_{1-6}$-alkyl-group may optionally be substituted independently from each other by one or two substituents selected independently from each other from the group consisting of F, NC—, $(R^6)_2N-$, HO—, O=, $C_{1-4}$-alkyl-, HOOC—, $C_{1-4}$-alkyl-OC(O)—, $(R^6)_2N-C(O)-$, $C_{1-3}$-alkyl-S—, $C_{1-3}$-alkyl-S(O)— and $C_{1-3}$-alkyl-S(O)$_2-$, and in case wherein two of the aforementioned groups $R^{5b}$ are connected to the same carbon atom, they may form together a $(CH_2)_{4-6}$-alkylene bridge, wherein said $(CH_2)_{4-6}$-alkylene bridge may optionally be substituted with one or two groups selected independently from each other from the group consisting of $H_3C-$, HO—, and $H_3C-O-$, and wherein one or two —$CH_2-$ groups of said $(CH_2)_{4-6}$-alkylene bridge may optionally be replaced by —O—.

6. The compound according to claim 1, wherein $R^6$ is selected independently of each other from the group $R^{6b}$ consisting of
$H_3C-$ and H.

7. The compound according to claim 1, wherein $R^7$ is selected from the group $R^{7b}$ consisting of H, F, Cl, Br, $C_{1-3}$-alkyl-, $F_3C-$, HO—, $C_{1-3}$-alkyl-O— and NC—, or the aforementioned group $R^{7b}$ may form together with $R^1$ a —$(CH_2)_{2-3}$-alkylene bridge.

8. The compound according to claim 1, wherein $R^{10}$ is selected independently of each other from the group $R^{10b}$ consisting of F, Cl, $C_{1-3}$-alkyl-, cyclopropyl-, $F_2HC-$, $F_3C-$, NC—, $H_2N-C(O)-$, $C_{1-3}$-alkyl-NH—C(O)—, $(C_{1-3}$-alkyl)$_2$N—C(O)—, HO—, $C_{1-3}$-alkyl-O—, $F_2HC-O-$, and $F_3C-O-$.

9. The compound according to claim 1, wherein $R^N$ is selected independently of each other from the group $R^{Nb}$ consisting of H, $C_{1-4}$-alkyl-, $C_{3-5}$-cycloalkyl-, $C_{1-4}$-alkyl-C(O)—, $C_{3-6}$-cycloalkyl-C(O)—, $C_{1-4}$-alkyl-S(O)$_2-$, and $C_{3-5}$-cycloalkyl-S(O)$_2-$.

10. A pharmaceutical compositions comprising at least one compound according to claim 1, or a pharmaceutically acceptable salt, thereof, together with one or more pharmaceutically acceptable carrier.

11. A method of using a compound according to claim 1, or a pharmaceutically acceptable salt thereof, for the treatment of a disease or condition selected from the group consisting of metabolic syndrome, type 1 or type 2 diabetes, obesity, and dyslipidemia.

* * * * *